(12) United States Patent
Valdez et al.

(10) Patent No.: US 12,163,955 B2
(45) Date of Patent: Dec. 10, 2024

(54) ANTIBODIES TO METHOTREXATE AND USES THEREOF

(71) Applicant: Ark Diagnostics, Inc., Fremont, CA (US)

(72) Inventors: Johnny Valdez, Los Altos Hills, CA (US); Byung Sook Moon, Los Altos Hills, CA (US); Rajendra Singh, San Jose, CA (US); Jacqueline Nguyen-Choi, Castro Valley, CA (US)

(73) Assignee: ARK Diagnostics, Inc., Fremont, CA (US)

( * ) Notice: Subject to any disclaimer, the term of this patent is extended or adjusted under 35 U.S.C. 154(b) by 0 days.

(21) Appl. No.: 18/186,899

(22) Filed: Mar. 20, 2023

(65) Prior Publication Data
US 2024/0319176 A1    Sep. 26, 2024

(51) Int. Cl.
*G01N 33/58* (2006.01)
*C07K 16/44* (2006.01)
*G01N 33/53* (2006.01)

(52) U.S. Cl.
CPC ......... *G01N 33/5308* (2013.01); *C07K 16/44* (2013.01); *G01N 33/581* (2013.01); *C07K 2317/33* (2013.01); *C07K 2317/622* (2013.01)

(58) Field of Classification Search
CPC .. G01N 33/5308; G01N 33/581; C07K 16/04; C07K 2317/33; C07K 2317/622
See application file for complete search history.

(56) References Cited

U.S. PATENT DOCUMENTS

| | | | |
|---|---|---|---|
| 8,168,756 B2 | 5/2012 | Valdez et al. | |
| 8,828,665 B2 | 9/2014 | Valdez et al. | |
| 8,841,136 B2 | 9/2014 | Valdez et al. | |
| 9,522,880 B2 | 12/2016 | Valdez et al. | |
| 9,920,136 B2 | 3/2018 | Valdez et al. | |
| 9,958,464 B2 | 5/2018 | Valdez et al. | |
| 9,970,929 B2 | 5/2018 | Valdez et al. | |
| 10,203,345 B2 | 2/2019 | Valdez et al. | |
| 10,690,687 B2 | 6/2020 | Valdez et al. | |
| 10,717,787 B1 | 7/2020 | Valdez et al. | |
| 10,745,492 B1 | 8/2020 | Valdez et al. | |
| 10,919,982 B2 | 2/2021 | Valdez et al. | |
| 11,136,412 B2 | 10/2021 | Valdez et al. | |
| 11,149,093 B2 | 10/2021 | Valdez et al. | |
| 11,231,424 B2 | 1/2022 | Valdez et al. | |
| 11,384,158 B2 | 7/2022 | Valdez et al. | |
| 11,402,395 B2 | 8/2022 | Valdez et al. | |
| 11,459,403 B2 | 10/2022 | Valdez et al. | |
| 11,525,835 B2 | 12/2022 | Valdez et al. | |
| 2010/0173427 A1* | 7/2010 | Valdez | C07D 207/26 435/207 |
| 2012/0283219 A1* | 11/2012 | Coish | A61P 31/04 514/249 |
| 2018/0328952 A1* | 11/2018 | von Borstel | G01N 33/9493 |
| 2020/0216453 A1 | 7/2020 | Cooper et al. | |
| 2020/0341016 A1 | 10/2020 | Valdez et al. | |
| 2020/0400696 A1 | 12/2020 | Valdez et al. | |

FOREIGN PATENT DOCUMENTS

CN 104569373 B    8/2016

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Xue et al., "Bioluminescent Antibodies for Point-of-Care Diagnostics," Angew. Chem. Int. Ed. Engl., 2017, vol. 56, No. 25, pp. 7112-7116.*
Supporting Information, pp. 1-34, of Xue et al., "Bioluminescent Antibodies for Point-of-Care Diagnostics," Angew. Chem. Int. Ed. Engl., 2017, vol. 56, No. 25, pp. 7112-7116.*
Pubchem, SID 237051752, Modify Date: Feb. 13, 2015 [retrieved on May 14, 2024]., Retrieved from the Internet <URL: https://pubchem.ncbi.nlm.nih.gov/substance/237051752>.

* cited by examiner

*Primary Examiner* — Galina M. Yakovleva
(74) *Attorney, Agent, or Firm* — Rudy J. Ng; Mandar A. Joshi; Bozicevic, Field & Francis LLP

(57) ABSTRACT

Disclosed herein are antibodies that specifically bind to a methotrexate analyte. Such antibodies can be used to detect a methotrexate analyte in a sample, such as in a homogeneous enzyme immunoassay method. Hapten structures to elicit such antibodies and conjugates useful in immunoassays are also described.

9 Claims, 10 Drawing Sheets
Specification includes a Sequence Listing.

(2S)-2-[[4-[[(2,4-diaminopteridin-6-yl)methyl-methylamino]benzoyl]amino]pentanedioic acid

[N-[4[[(2,4-diamino-6-pteridinyl) methyl] methylamino]benzoyl]-L-glutamic acid

7-Hydroxy Methotrexate (7-OH MTX)

4-(((2,4-Diaminopteridin-6-yl)methyl)(methyl)amino)benzoic acid
DAMPA

A. Inhibition

B. Modulation

```
                              SEQUENCE LISTING

Sequence total quantity: 30
SEQ ID NO: 1            moltype = AA   length = 473
FEATURE                 Location/Qualifiers
source                  1..473
                        mol_type = protein
                        organism = synthetic construct
SEQUENCE: 1
METGPRWLLL VAVLKGVQCQ SLEESGGDLV KPGASLALTC KASGLDFSRS DHWICWVRQA   60
PGKGLESIGC IYIGSGTFVR SGTTYYASWA KGRFTISKTS STTVTLQMTS LTGADTATYF  120
CARGFYATDG YGGPSYLNLW GQGTLVTVSS GQPKAPSVFP LAPCCGDTPS STVTLGCLVK  180
GYLPEPVTVT WNSGTLTNGV RTPPSVRQSS GLYSLSSVVS VTSSSQPVTC NVAHPATNTK  240
VDKTVAPSTC SKPTCPPPEL LGGPSVFIFP PKPKDTLMIS RTPEVTCVVV DVSQDDPEVQ  300
FTWYINNEQV RTARPPLREQ QFNSTIRVVS TLPITHQDWL RGKEFKCKVH NKALPAPIEK  360
TISKARGQPL EPKVYTMGPP REELSSRSVS LTCMINGFYP SDISVEWEKN GKAEDNYKTT  420
PAVLDSDGSY FLYNKLSVPT SEWQRGDVFT CSVMHEALHN HYTQKSISRS PGK         473

SEQ ID NO: 2            moltype = AA   length = 7
FEATURE                 Location/Qualifiers
source                  1..7
                        mol_type = protein
                        organism = synthetic construct
SEQUENCE: 2
RSDHWIC                                                              7

SEQ ID NO: 3            moltype = AA   length = 23
FEATURE                 Location/Qualifiers
source                  1..23
                        mol_type = protein
                        organism = synthetic construct
SEQUENCE: 3
CIYIGSGTFV RSGTTYYASW AKG                                           23

SEQ ID NO: 4            moltype = AA   length = 16
FEATURE                 Location/Qualifiers
source                  1..16
                        mol_type = protein
                        organism = synthetic construct
SEQUENCE: 4
GFYATDGYGG PSYLNL                                                   16

SEQ ID NO: 5            moltype = AA   length = 239
FEATURE                 Location/Qualifiers
source                  1..239
                        mol_type = protein
                        organism = synthetic construct
SEQUENCE: 5
MDTRAPTQLL GLLLLWLPGA RCADIVMTQT PASVEAAVGG TVTIKCQASE SISSYCSWFQ   60
QKPGQPPKLL IYRASTLESG VPSRFKGSGS GTQFTLTISD LECADAATYY CQSYAYSSPD  120
SYGSTFGGGT EVVVKGDPVA PTVLIFPPAA DQVATGTVTI VCVANKYFPD VTVTWEVDGT  180
TQTTGIENSK TPQNSADCTY NLSSTLTLTS TQYNSHKEYT CKVTQGTTSV VQSFNRGDC   239

SEQ ID NO: 6            moltype = AA   length = 11
FEATURE                 Location/Qualifiers
source                  1..11
                        mol_type = protein
                        organism = synthetic construct
SEQUENCE: 6
QASESISSYC S                                                        11

SEQ ID NO: 7            moltype = AA   length = 7
FEATURE                 Location/Qualifiers
source                  1..7
                        mol_type = protein
                        organism = synthetic construct
SEQUENCE: 7
RASTLES                                                              7

SEQ ID NO: 8            moltype = AA   length = 14
FEATURE                 Location/Qualifiers
source                  1..14
```

```
                            mol_type = protein
                            organism = synthetic construct
SEQUENCE: 8
QSYAYSSPDS YGST                                                          14

SEQ ID NO: 9                moltype = AA   length = 473
FEATURE                     Location/Qualifiers
source                      1..473
                            mol_type = protein
                            organism = synthetic construct
SEQUENCE: 9
METGLRWLLL VAVLKGVQCQ SLEESGGDLV KPGASLTLTC TASGLSFSSS DHWICWVRQA         60
PGKGLESVGC IYIGSGTFVS SGTTYFASWA KGRSIISKTS STTVTLQMTS LTAADTATYF        120
CARGFYYTDG SGGPSYLNLW GQGTLVTVSS GQPKAPSVFP LAPCCGDTPS STVTLGCLVK        180
GYLPEPVTVT WNSGTLTNGV RTFPSVRQSS GLYSLSSVVS VTSSSQPVTC NVAHPATNTK        240
VDKTVAPSTC SKPTCPPPEL LGGPSVFIFP PKPKDTLMIS RTPEVTCVVV DVSQDDPEVQ        300
FTWYINNEQV RTARPPLREQ QFNSTIRVVS TLPITHQDWL RGKEFKCKVH NKALPAPIEK        360
TISKARGQPL EPKVYTMGPP REELSSRSVS LTCMINGFYP SDISVEWEKN GKAEDNYKTT        420
PAVLDSDGSY FLYNKLSVPT SEWQRGDVFT CSVMHEALHN HYTQKSISRS PGK               473

SEQ ID NO: 10               moltype = AA   length = 7
FEATURE                     Location/Qualifiers
source                      1..7
                            mol_type = protein
                            organism = synthetic construct
SEQUENCE: 10
SSDHWIC                                                                   7

SEQ ID NO: 11               moltype = AA   length = 23
FEATURE                     Location/Qualifiers
source                      1..23
                            mol_type = protein
                            organism = synthetic construct
SEQUENCE: 11
CIYIGSGTFV SSGTTYFASW AKG                                                23

SEQ ID NO: 12               moltype = AA   length = 16
FEATURE                     Location/Qualifiers
source                      1..16
                            mol_type = protein
                            organism = synthetic construct
SEQUENCE: 12
GFYYTDGSGG PSYLNL                                                        16

SEQ ID NO: 13               moltype = AA   length = 239
FEATURE                     Location/Qualifiers
source                      1..239
                            mol_type = protein
                            organism = synthetic construct
SEQUENCE: 13
MDTRAPTQLL GLLLLWLPGA RCADIVMTQT PASVEAAVGG TVTIKCQASQ TIYSYLSWFQ         60
QKPGQPPKLL IYSASTLASG VSSRFKGSRS GTESTLTISD LECADAATYY CQSYMYSSSS        120
SFGSTFGGGT EVVVKGDPVA PTVLIFPPAA DQVATGTVTI VCVANKYFPD VTVTWEVDGT        180
TQTTGIENSK TPQNSADCTY NLSSTLTLTS TQYNSHKEYT CKVTQGTTSV VQSFNRGDC        239

SEQ ID NO: 14               moltype = AA   length = 11
FEATURE                     Location/Qualifiers
source                      1..11
                            mol_type = protein
                            organism = synthetic construct
SEQUENCE: 14
QASQTIYSYL S                                                             11

SEQ ID NO: 15               moltype = AA   length = 7
FEATURE                     Location/Qualifiers
source                      1..7
                            mol_type = protein
                            organism = synthetic construct
SEQUENCE: 15
SASTLAS                                                                   7

SEQ ID NO: 16               moltype = AA   length = 14
FEATURE                     Location/Qualifiers
source                      1..14
                            mol_type = protein
                            organism = synthetic construct
SEQUENCE: 16
QSYMYSSSSS FGST                                                          14
```

```
SEQ ID NO: 17           moltype = AA  length = 460
FEATURE                 Location/Qualifiers
source                  1..460
                        mol_type = protein
                        organism = synthetic construct
SEQUENCE: 17
METGLRWLLL VAVLKGVQCQ SLEESGGRLV TPGTPMTLTC TASGFSLVKY YMTWVRQAPG   60
KGLEYIGVIW SGGMTYYASW AKGRFTISRT STTVDLKIIS PTTEDTATYF CARERDYFDG  120
YIGNDIWGQG TLVTVSSGQP KAPSVFPLAP CCGDTPSSTV TLGCLVKGYL PEPVTVTWNS  180
GTLTNGVRTF PSVRQSSGLY SLSSVVSVTS SSQPVTCNVA HPATNTKVDK TVAPSTCSKP  240
TCPPPELLGG PSVFIFPPKP KDTLMISRTP EVTCVVVDVS QDDPEVQFTW YINNEQVRTA  300
RPPLREQQFN STIRVVSTLP ITHQDWLRGK EFKCKVHNKA LPAPIEKTIS KARGQPLEPK  360
VYTMGPPREE LSSRSVSLTC MINGFYPSDI SVEWEKNGKA EDNYKTTPAV LDSDGSYFLY  420
NKLSVPTSEW QRGDVFTCSV MHEALHNHYT QKSISRSPGK                        460

SEQ ID NO: 18           moltype = AA  length = 5
FEATURE                 Location/Qualifiers
source                  1..5
                        mol_type = protein
                        organism = synthetic construct
SEQUENCE: 18
KYYMT                                                                5

SEQ ID NO: 19           moltype = AA  length = 16
FEATURE                 Location/Qualifiers
source                  1..16
                        mol_type = protein
                        organism = synthetic construct
SEQUENCE: 19
VIWSGGMTYY ASWAKG                                                   16

SEQ ID NO: 20           moltype = AA  length = 13
FEATURE                 Location/Qualifiers
source                  1..13
                        mol_type = protein
                        organism = synthetic construct
SEQUENCE: 20
ERDYFDGYIG NDI                                                      13

SEQ ID NO: 21           moltype = AA  length = 238
FEATURE                 Location/Qualifiers
source                  1..238
                        mol_type = protein
                        organism = synthetic construct
SEQUENCE: 21
MDTRAPTQLL GLLLLWLPGA TFAQVLTQTP SSVSAAVGGT VTINCQSSQS VWSRHLSWFQ   60
QKPGQPPKLL IYKASTLASG VPSRFSGSGS GTQFTLTISD VQCDDAATYY CLGGYTCIRD  120
DCRAFGGGTE VVVKGDPVAP TVLIFPPAAD QVATGTVTIV CVANKYFPDV TVTWEVDGTT  180
QTTGIENSKT PQNSADCTYN LSSTLTLTST QYNSHKEYTC KVTQGTTSVV QSFNRGDC    238

SEQ ID NO: 22           moltype = AA  length = 12
FEATURE                 Location/Qualifiers
source                  1..12
                        mol_type = protein
                        organism = synthetic construct
SEQUENCE: 22
QSSQSVWSRH LS                                                       12

SEQ ID NO: 23           moltype = AA  length = 7
FEATURE                 Location/Qualifiers
source                  1..7
                        mol_type = protein
                        organism = synthetic construct
SEQUENCE: 23
KASTLAS                                                              7

SEQ ID NO: 24           moltype = AA  length = 13
FEATURE                 Location/Qualifiers
source                  1..13
                        mol_type = protein
                        organism = synthetic construct
SEQUENCE: 24
LGGYTCIRDD CRA                                                      13

SEQ ID NO: 25           moltype = DNA  length = 1422
FEATURE                 Location/Qualifiers
source                  1..1422
                        mol_type = other DNA
                        organism = synthetic construct
```

```
SEQUENCE: 25
atggagaccg gccccaggtg gctgctgctg gtggccgtgc tgaagggcgt gcagtgccag    60
agcctggagg agagcggcgg cgacctggtg aagcccggcg ccagcctggc cctgacctgc   120
aaggccagcg gcctggactt cagcaggagc gaccactgga tctgctgggt gaggcaggcc   180
cccggcaagg gcctggagag catccggctg catctacatcg gcagcggcac cttcgtgagg   240
agcggcacca cctactacgc cagctgggcc aagggcaggt tcaccatcag caagaccagc   300
agcaccaccg tgaccctgca gatgaccagc ctgaccggcg ccgacaccgc cacctacttc   360
tgcgccaggg gcttctacgc caccgacggc tacggcggcc ccagctacct gaacctgtgg   420
ggccagggca cctggtgac cgtgagcagc ggccagccca aggcccccag cgtgttcccc   480
ctggccccct gctgcggcga caccccagc agcaccggca ccctgggctg cctggtgaag   540
ggctacctgc ccgagcccgt gaccgtgacc tggaacagcg gcaccctgac caacggcgtg   600
aggaccttcc ccagcgtgag gcagagcagc ggcctgtaca gcctgagcag cgtggtgagc   660
gtgaccagca gcagccagcc cgtgacctgc aacgtggccc accccgccac caacaccaag   720
gtggacaaga ccgtggcccc cagcacctgc agcaagccca cctgccccc cccgagctg   780
ctgggcggcc ccagcgtgtt catcttcccc cccaagccca aggacaccct gatgatcagc   840
aggaccccg aggtgacctg cgtggtggtg gacgtgagcc aggacgaccc cgaggtgcag   900
ttcacctggt acatcaacaa cgagcaggtg aggaccgcca ggccccccct gagggagcag   960
cagttcaaca gcaccatcag ggtggtgagc accctgccca tcacccacca ggactggctg  1020
aggggcaagg agttcaagtg caaggtgcac aacaaggccc tgcccgcccc catcgagaag  1080
accatcagca aggccagggg ccagcccctg gagcccaagg tgtacaccat gggccccccc  1140
agggaggagc tgagcagcag gagcgtgagc ctgacctgca tgatcaacgg cttctacccc  1200
agcgacatca gcgtggagtg ggagaagaac ggcaaggccg aggacaacta caagaccacc  1260
cccgccgtgc tggacagcga cggcagctac ttcctgtaca acaagctgag cgtgcccacc  1320
agcgagtggc agaggggcga cgtgttcacc tgcagcgtga tgcacgaggc cctgcacaac  1380
cactacaccc agaagagcat cagcaggagc cccggcaagt ga                     1422

SEQ ID NO: 26          moltype = DNA  length = 717
FEATURE                Location/Qualifiers
source                 1..717
                       mol_type = other DNA
                       organism = synthetic construct SEQUENCE: 26
atggacacca gggcccccac ccagctgctg ggcctgctgc tgctgtggct gcccggcgcc    60
aggtgcgccg acatcgtgat gacccagacc cccgccagcg tggaggccgc cgtgggcggc   120
accgtgacca tcaagtgcca ggccagcgag agcatcagca gctactgcag ctggttccag   180
cagaagcccg gccagccccc caagctgctg atctacaggg ccagcaccct ggagagcggc   240
gtgcccagca ggttcaaggg cagcggcagc ggcacccagt tcaccctgac catcagcgac   300
ctggagtgcg ccgacgccgc cacctactac tgccagagct acgcctacag cagccccgac   360
agctacggca gcaccttcgg cggcggcacc gaggtggtgg tgaagggcca ccccgtggcc   420
cccaccgtgc tgatcttccc ccccgccgcc gaccaggtgg ccaccggcac cgtgaccatc   480
gtgtgcgtgg ccaacaagta cttccccgac gtgacccgtga cctgggaagt ggacggcacc   540
acccagacca ccggcatcga gaacagcaag acccccagg acagcgccga ctgcacctac   600
aacctgagca gcaccctgac cctgaccagc acccagtaca acagccacaa ggagtacacc   660
tgcaaggtga cccagggcac caccagcgtg gtgcagagct tcaacagggg cgactgc      717

SEQ ID NO: 27          moltype = DNA  length = 1422
FEATURE                Location/Qualifiers
source                 1..1422
                       mol_type = other DNA
                       organism = synthetic construct SEQUENCE: 27
atggagaccg gcctgaggtg gctgctgctg gtggccgtgc tgaagggcgt gcagtgccag    60
agcctggagg agagcggcgg cgacctggtg aagcccggcg ccagcctgac cctgacctgc   120
accgccagcg gcctgagctt cagcagcagc gaccactgga tctgctgggt gaggcaggcc   180
cccggcaagg gcctggagag cgtgggctgc atctacatcg gcagcggcac cttcgtgagc   240
agcggcacca cctacttcgc cagctgggcc aagggcagga gcatcatcag caagaccagc   300
agcaccaccg tgaccctgca gatgaccagc ctgaccggcg ccgacaccgc cacctacttc   360
tgcgccaggg gcttctacta caccgacggc agcggcggcc ccagctacct gaacctgtgg   420
ggccagggca cctggtgac cgtgagcagc ggccagccca aggcccccag cgtgttcccc   480
ctggccccct gctgcggcga caccccagc agcaccggca ccctgggctg cctggtgaag   540
ggctacctgc ccgagcccgt gaccgtgacc tggaacagcg gcaccctgac caacggcgtg   600
aggaccttcc ccagcgtgag gcagagcagc ggcctgtaca gcctgagcag cgtggtgagc   660
gtgaccagca gcagccagcc cgtgacctgc aacgtggccc accccgccac caacaccaag   720
gtggacaaga ccgtggcccc cagcacctgc agcaagccca cctgccccc cccgagctg   780
ctgggcggcc ccagcgtgtt catcttcccc cccaagccca aggacaccct gatgatcagc   840
aggaccccg aggtgacctg cgtggtggtg gacgtgagcc aggacgaccc cgaggtgcag   900
ttcacctggt acatcaacaa cgagcaggtg aggaccgcca ggccccccct gagggagcag   960
cagttcaaca gcaccatcag ggtggtgagc accctgccca tcacccacca ggactggctg  1020
aggggcaagg agttcaagtg caaggtgcac aacaaggccc tgcccgcccc catcgagaag  1080
accatcagca aggccagggg ccagcccctg gagcccaagg tgtacaccat gggccccccc  1140
agggaggagc tgagcagcag gagcgtgagc ctgacctgca tgatcaacgg cttctacccc  1200
agcgacatca gcgtggagtg ggagaagaac ggcaaggccg aggacaacta caagaccacc  1260
cccgccgtgc tggacagcga cggcagctac ttcctgtaca acaagctgag cgtgcccacc  1320
agcgagtggc agaggggcga cgtgttcacc tgcagcgtga tgcacgaggc cctgcacaac  1380
cactacaccc agaagagcat cagcaggagc cccggcaagt ga                     1422

SEQ ID NO: 28          moltype = DNA  length = 717
FEATURE                Location/Qualifiers
source                 1..717
```

```
                        mol_type = other DNA
                        organism = synthetic construct
SEQUENCE: 28
atggacacca gggcccccac ccagctgctg ggcctgctgc tgctgtggct gcccggcgcc    60
aggtgcgccg acatcgtgat gacccagacc cccgccagcg tggaggccgc cgtgggcggc   120
accgtgacca tcaagtgcca ggccagccag accatctaca gctacctgag ctggttccag   180
cagaagcccg gccagccccc caagctgctg atctacagcg ccagcaccct ggccagcggc   240
gtgagcagca ggttcaaggg cagcaggagc ggcaccgaga gcccctgac catcagcgac   300
ctggagtgcg ccgacgccgc cacctactac tgccagagct acatgtacag cagcagcagc   360
agcttcggca gcaccttcgg cggcggcacc gaggtggtgg tgaagggcga ccccgtggcc   420
cccaccgtgc tgatcttccc ccccgccgcc gaccaggtgg ccaccggcac cgtgaccatc   480
gtgtgcgtgg ccaacaagta cttccccgac gtgaccgtga cctgggaggt ggacggcacc   540
acccagacca ccggcatcga gaacaagaag accccccaga gcagcgccga ctgcacctac   600
aacctgagca gcaccctgac cctgaccagc accagtaca cagccacaa ggagtacacc   660
tgcaaggtga cccagggcac caccagcgtg gtgcagagct caacaggggg cgactgc      717

SEQ ID NO: 29            moltype = DNA   length = 1383
FEATURE                  Location/Qualifiers
source                   1..1383
                         mol_type = other DNA
                         organism = synthetic construct
SEQUENCE: 29
atggagaccg gcctgaggtg gctgctgctg gtggccgtgc tgaagggcgt gcagtgccag    60
agcctggagg agagcggcgg caggctggtg accccccggca cccccatgac cctgacctgc   120
accgccagcg gcttcagcct ggtgaagtac tacatgacct gggtgaggca ggccccccggc  180
aagggcctgg agtacatcgg cgtgatctgg agcggcggca tgacctacta cgccagctgg   240
gccaagggca ggttcaccat cagcaggacc agcaccaccg tggacctgaa gatcatcagc   300
cccaccaccg aggacaccgc cacctacttc tgcgccaggg agagggacta cttcgacggc   360
tacatcggca cgacatctg gggccagggc accctggtga ccgtgagcag cggccagccc   420
aaggcccccca gcgtgttccc cctggccccc tgctgcggcg acaccccag cagcaccgtg   480
accctgggct gcctggtgaa gggctacctg cccgagcccg tgaccgtgac ctggaacagc   540
ggcacccctga ccaacggcgt gaggaccttc cccagcgtga ggcagagcag cggcctgtac  600
agcctgagca gcgtggtgag cgtgaccagc agcagcagc ccgtgacctg caacgtggcc   660
caccccgcca ccaacaccaa ggtggacaag accgtgcccg cagcacctg cagcaagccc   720
acctgccccc ccccccgagct gctgggcggc cccagcgtgt tcatcttccc ccccaagccc   780
aaggacaccc tgatgatcag caggaccccc gaggtgacct gcgtggtggt ggacgtgagc   840
caggacgacc ccgaggtgca gttcacctgg tacatcaaca cgagcaggt gaggaccgcc   900
aggccccccc tgagggagca gcagttcaac agcaccatca gggtggtgag caccctgccc   960
atcccccacc aggactggct gaggggcaag gagttcaagt gcaaggtgca acaagggcc  1020
ctgcccgccc ccatcgagaa gaccatcagc aaggccaggg gccagccct ggagcccaag  1080
gtgtacacca tgggcccccc cagggaggag ctgagcagca ggagcgtgag cctgacctgc  1140
atgatcaacg gcttctaccc cagcgacatc agcgtggagt gggagaagaa cggcaaggcc  1200
gaggacaact acaagaccac ccccgccgtg ctggacagcg acggcagcta cttcctgtac  1260
aacaagctga cgtgcccac cagcgagtgg cagaggggac acgtgttcac ctgcagcgtg  1320
atgcacgagg ccctgcacaa ccactacacc cagaagagca tcagcaggag ccccggcaag  1380
tga                                                               1383

SEQ ID NO: 30            moltype = DNA   length = 714
FEATURE                  Location/Qualifiers
source                   1..714
                         mol_type = other DNA
                         organism = synthetic construct
SEQUENCE: 30
atggacacca gggcccccac ccagctgctg ggcctgctgc tgctgtggct gcccggcgcc    60
accttcgccc aggtgctgac ccagacccc agcagcgtga gcgccgccgt gggcggcacc   120
gtgaccatca actgccagag cagccagagc gtgtggagca gcaacctgag ctggttccag   180
cagaagcccg gccagccccc caagctgctg atctacaagg ccagcaccct ggccagcggc   240
gtgcccagca ggttcagcgg cagcggcagc ggcacccagt tcaccctgac catcagcgac   300
gtgcagtgcg acgacgccgc cacctactac tgcctgggcg gctacacctg catcagggac   360
gactgcaggg ccttcggcgg cggcaccgag gtggtggtga agggcgaccc cgtggccccc   420
accgtgctga tcttccccc cgccgccgac caggtggcca ccggcaccgt gaccatcgtg   480
tgcgtggcca acaagtactt ccccgacgtg accgtgacct gggaggtgga cggcaccacc   540
cagaccaccg gcatcgagaa cagcaagacc cccagaaca gcgccgactg cacctacaac   600
ctgagcagca ccctgaccct gaccagcacc cagtacaaca gccacaagga gtacacctgc   660
aaggtgaccc agggcaccac cagcgtggtg cagagcttca cagggcgcga ctgc         714
```

ANTIBODIES TO METHOTREXATE AND USES THEREOF

FIELD OF THE INVENTION

The present invention relates to methods and systems for the detection of methotrexate (MTX) using immunoassays. In particular, the invention relates to antibodies and haptens used in immunoassays for the detection and quantification of MTX in biological samples.

INCORPORATION BY REFERENCE OF SEQUENCE LISTING

A Sequence Listing is provided herewith as a Sequence Listing XML, "ARKD-009_SEQ_LIST.xml" created on Mar. 20, 2023 and having a size of 35,274 bytes. The contents of the Sequence Listing XML are incorporated herein by reference in their entirety.

INTRODUCTION

MTX [N-[4[[(2,4-diamino-6-pteridinyl) methyl] methylamino]benzoyl]-L-glutamic acid, abbreviated MTX], formerly Amethopterin, is an antimetabolite used in the treatment of certain neoplastic diseases, severe psoriasis, and adult rheumatoid arthritis.

MTX has a distinct mechanism of action regarding its use in chemotherapy and immunosuppression in autoimmune diseases. In cancer, MTX acts as an antifolate antimetabolite. MTX is taken up into the cell by carriers called the human reduced folate carriers, and it forms MTX-polyglutamate. Both MTX and the MTX-polyglutamate inhibit the enzyme dihydrofolate reductase, which catalyzes the conversion of dihydrofolate into tetrahydrofolate, the active form of folic acid. Tetrahydrofolate is necessary for the synthesis of the nucleotides of both DNA and RNA. MTX-polyglutamate further inhibits the de novo purine synthesis of both purine and thymidylate synthase, thereby inhibiting DNA synthesis. This mechanism is utilized in the treatment of cancer because of its cytotoxic effect.

In autoimmune diseases, different mechanisms are involved in choosing MTX as a drug of choice. It inhibits enzyme a transformylase, leading to hindrance in adenosine and guanine metabolism, Adenosine accumulation translates to anti-inflammatory action of adenosine, manifesting in repression of T-cell activation, down-regulation of B-cells, increasing activated CD-95 T cells sensitivity; and repression of methyltransferase activity, inhibition of the binding of beta-1 interleukin to its cell surface receptor.

MTX has the potential for serious toxicity. Patients undergoing MTX therapy need to be closely monitored so that toxic effects are detected promptly. Intermediate to high doses of MTX (approximately 35 mg/m$^2$-12 g/m$^2$) with leucovorin (citrovorum-factor) rescue have been used with favorable results in the treatment of osteogenic sarcoma, leukemia, non-Hodgkin's lymphoma, lung and breast cancer.

High-dose MTX (HDMTX) is the term for doses higher than 500 mg/ml. Patients experience nausea, mucosal ulceration, alopecia, fatigue, fever, increased risk of infection, leukopenia, GI bleeding, pancreatitis, cirrhosis, aplastic anemia, malignancy (lymphoproliferative disorders), infections, interstitial pneumonitis, renal impairment, and teratogenesis. Accurate monitoring of MTX concentrations in the blood is critical for ensuring safe and effective treatment, as well as for avoiding toxicity due to over-exposure.

The three antidotes used for MTX toxicity are leucovorin, thymidine, and glucarpidase. Leucovorin is the reduced active form of folic acid. It rescues normal cells from the toxic effects caused by MTX's inhibition of reduced folates. Leucovorin is particularly effective in preventing myelosuppression, gastrointestinal toxicity, and neurotoxicity during MTX treatment. Thymidine rescues cells from the cytotoxic effects of MTX; however, its use is still under investigation and is always given together with the other drugs. Glucarpidase converts MTX into 4-(((2,4-diaminopteridin-6-yl) methyl)(methyl)amino)benzoic acid (DAMPA) and glutamate, two nontoxic metabolites, thus rapidly removing MTX in patients with renal dysfunction. Glucarpidase, in combination with leucovorin, is a common therapy for MTX toxicity. A single dose of glucarpidase reduces plasma MTX concentrations by 97% or more within 15 minutes. Hydration and urine alkalination are recommended for renal impairment.

MTX serum levels depend on indication for use, dosage, mode of administration, treatment regimen, individual pharmacokinetics, metabolism and other clinical factors. While the serum level may typically reach approximately 10 to 100 μmol/L in treatment of breast cancer (for example), concentrations may exceed 1000 μmol/L with high dose therapy for osteosarcoma, and up to 3100 μmol/L MTX was reached following a 4-hour infusion in pediatric patients with osteosarcoma. For treatment of osteosarcoma, the MTX decay curve has wide variability: 24 hours, 30 to 300 μmol/L; 48 hours, 3 to 30 μmol/L; and 72 hours, less than 0.3 μmol/L. A dose of 10 mg of leucovorin is usually administered intravenously 24 hours after initiation of the MTX infusion. Subsequent doses are adjusted and administered according to the MTX levels obtained at 24, 48, and 72 hours. MTX levels in excess of 50 μmol/L at 24 hours, 10 μmol/L at 48 hours, and 0.5 μmol/L at 72 hours portend potential toxicity and are usually treated with an increase in the dose of leucovorin in accordance with algorithms until the MTX level is <0.1 μmol/L. Guidelines for MTX therapy with leucovorin rescue usually recommend continuance of leucovorin until the MTX level falls below 0.05 μmol/L. Thus, there is a need for an analytical method to determine the concentration of MTX in patient samples, particularly plasma and serum with high sensitivity and specificity.

Several analytical methods are used to determine the concentration of MTX in serum or plasma.

The following analytical methods have been used to determine MTX concentrations with varying degrees of sensitivity and specificity. They are fluorescence polarization immunoassay (FPIA), enzyme linked immunoassay (ELISA), radioimmunoassay (RIA), High pressure liquid chromatography (HPLC), HPLC coupled to tandem mass spectrometry (LC-MS/MS) and enzyme multiplied immunoassay technique (EMIT).

Homogeneous Immunoassays have been used for over the last 40 years for monitoring serum or plasma levels of therapeutic drugs in the clinical laboratory and hospital. Some advantages of immunoassays are that such assays are accurate, sensitive, and in many commercial assay formats, easy to use. Immunoassays to measure MTX have been commercialized and their availability has enabled the routine measurement of drug levels in patient samples. Such assays have some limitations with respect to sensitivity and specificity. Immunoassays depend on the antibody reagent selection to provide specificity which is challenging as it is usually difficult or impossible to construct a drug analog suitable for conjugation to a large molecule (such as a protein) to develop an immunogen that induces an antibody that reacts with the drug. Often, the derivatization necessary to create an immunogen sufficiently alters the drug such that the resulting antibodies recognize the analog, but not the drug. Therefore, preparation of analogs that are suitable for conjugation to a protein and induce antibodies that recognize both the analog and the drug is required to develop an immunoassay. The IUPAC nomenclature of MTX (MTX) is (2S)-2-[[4-[(2,4-diaminopteridin-6-yl)methyl-methyl-amino]benzoyl]amino]pentanedioic acid, which is also named N-[4[[(2,4-diamino-6-pteridinyl) methyl] methyl-amino]benzoyl]-L-glutamic acid (CAS number is 59-05-2).

The structure of MTX and the IUPAC names are also provided in FIG. 1.

Abbott commercialized a FPIA based assay for MTX on the TDx/FLx however the optical configuration to capture the signal is cumbersome and difficult to integrate with other assays limiting throughput. The principle of the FPIA involves competitive binding of antibody with a small molecule (free antigen) and fluorescein-conjugated antigen. As the amount of antigen increases, the amount of conjugate bound to antibody decreases leading to a detection response that is inversely proportional to antigen concentration. The assay signal is polarized light and it decreases with increasing concentration and is not a kinetic readout. Such embodiments of the present invention utilize a kinetic readout where the signal is directly proportional to the analyte concentration.

Siemens Syva® EMIT® technology employs a competitive enzyme immunoassay principle based on competition between drug in the specimen and MTX labeled with the enzyme glucose-6-phosphate dehydrogenase (G6PDH) for binding to the antibody reagent. As the latter binds antibody, enzyme activity decreases. In the presence of drug from the specimen, enzyme activity increases and is directly proportional to the drug concentration. Active enzyme converts the coenzyme nicotinamide adenine dinucleotide (NAD$^+$) to NADH that is measured spectrophotometrically as a rate of change in absorbance. Endogenous serum G6PDH does not interfere with the results because the coenzyme NAD$^+$ functions only with the bacterial enzyme used in the assay. However the assay has limited sensitivity with the product insert claiming 0.3 mmol/L. (Mendu, D. R. et.al. 2007. *Ther Drug Monit* 29:632-637). There is therefore a need for an assay with higher sensitivity.

In order for immunoassays to be specific for MTX and not cross react with the major metabolite 7-OH MTX, antibodies are directed toward the pteridine ring portion of the molecule.

Compounds and methods for the detection of MTX, U.S. Pat. No. 11,054,430, describes compounds and methods for detecting MTX in biological samples using antibodies specific for MTX that have minimal cross reactivity to 7-OH MTX and DAMPA. The assay does have a high cross reactivity to 7-OH MTX and the dynamic range is limited. There is a need for superior specificity and higher dynamic range.

SUMMARY

The present disclosure provides methods for immunoassay of a MTX analyte. In some embodiments, the present disclosure relates to the use of derivatives of MTX haptens, tracers and conjugates in a signal producing immunoassay system. The present disclosure also relates to the use of immunogens of MTX analogs used for producing antibodies for capture of such analytes.

In some embodiments, the present disclosure provides MTX derivatives acylated and/or alkylated on the phenyl group of MTX (FIG. 1). In certain embodiments, such derivatives are used to produce conjugates useful in the immunoassays described herein.

In some embodiments, the present disclosure provides a polyclonal or monoclonal antibody that specifically binds to MTX, with less than 0.1% cross reactivity to 7 hydroxy MTX metabolite in the presence of the parent molecule.

In some embodiments, the present disclosure provides a polyclonal or monoclonal antibody that specifically binds to MTX, In some embodiments, the antibody may specifically bind to one or more of MTX, Pralatrexate or Phototrexate.

In some embodiments, the present disclosure provides a polyclonal or monoclonal antibody that specifically binds to free MTX and has less than 0.1% cross reactivity to triamterene and trimethoprim.

In some embodiments, the present disclosure provides methods for the syntheses of haptens, immunogens and conjugates starting from 2,4 diamino pteridine. In some embodiments, the synthesis includes coupling through phenyl group of the 2,4 diamino-6-pteridinyl methylaminomethyl (DAM) with a linking group to a protein or a label (e.g., a label enzyme).

This disclosure relates to novel haptens from the phenyl moiety of the diamino pteridinyl benzoic acid. In some aspects, these haptens are conjugated to proteins through various linkers, and thus provide monoclonal antibodies and enzyme conjugates that further reduce the cross reactivity.

Further, this disclosure provides antibodies having binding specificity to MTX. In some cases, MTX antibodies comprise a variable heavy chain and a variable light chain, wherein the variable heavy chain amino acid sequence comprises SEQ ID NO: 1 and wherein the variable light chain amino acid sequence comprises SEQ ID NO: 5.

The present disclosure also describes antibodies having binding specificity to MTX and have a variable heavy chain and a variable light chain, wherein the variable heavy chain amino acid sequence comprises SEQ ID NO: 9 and wherein the variable light chain amino acid sequence comprises SEQ ID NO: 13.

The present disclosure relates generally to antibodies having binding specificity to MTX and a variable heavy chain and a variable light chain, wherein the variable heavy chain nucleotide sequence comprises SEQ ID NO: 17 and wherein the variable light chain nucleotide sequence comprises SEQ ID NO: 21.

The present disclosure further describes methods of detecting MTX (MTX) in a sample, comprising the steps of combining in a solution the sample with a capture molecule and a labeled MTX, wherein the capture molecule is capable of binding the labeled MTX, and wherein MTX when present in the sample competes with the labeled MTX for binding to the capture molecule. The methods comprise detecting an amount of labeled MTX bound to the capture molecule through signal produced by a label on the bound labeled MTX, wherein the signal is inversely proportional to the amount of MTX present in the sample.

Further, the present disclosure provides kits for detecting MTX in a sample, the kit comprising a capture molecule; a labeled MTX, wherein the capture molecule is capable of binding the labeled MTX and wherein MTX competitively inhibits binding of the labeled MTX to the capture molecule. The kits may also comprise instructions for performing the detection assay, including combining in a solution the sample with a capture molecule and a labeled MTX, wherein the capture molecule is capable of binding the labeled MTX, and wherein MTX when present in the sample competes with the labeled MTX for binding to the capture molecule; and detecting an amount of labeled MTX bound to the capture molecule through signal produced by a label on the bound labeled MTX, wherein the signal is inversely proportional to the amount of MTX present in the sample.

BRIEF DESCRIPTION OF THE DRAWINGS

The present disclosure will be more fully understood from the following detailed description thereof taken in connection with the accompanying drawings which form a part of this application and in which.

BRIEF DESCRIPTION OF THE SEQUENCES

Figure 1:
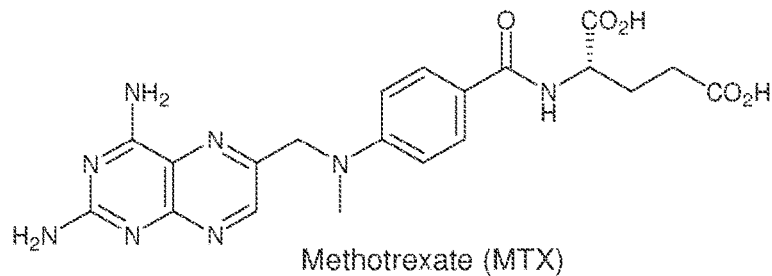
FIG. 1 shows the chemical structures for MTX (MTX) and the numbering system (IUPAC) with an alternative nomenclature.
Figure 1:
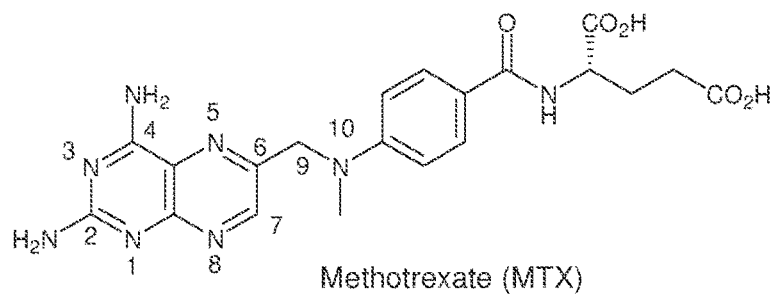

SEQ ID NO: 1 is the amino acid sequence of the variable heavy chain of an antibody Clone 28 of the present disclosure.

SEQ ID NO: 2 is the amino acid sequence of the first complementarity determining region (CDR1) of the variable heavy chain of SEQ ID NO: 1.

SEQ ID NO: 3 is the amino acid sequence of the second complementarity determining region (CDR2) of the variable heavy chain of SEQ ID NO: 1.

SEQ ID NO: 4 is the amino acid sequence of the third complementarity determining region (CDR3) of the variable heavy chain of SEQ ID NO: 1.

SEQ ID NO: 5 is the amino acid sequence of the variable light chain of an antibody Clone 28 of the present disclosure.

SEQ ID NO: 6 is the amino acid sequence of the CDR1 of the variable light chain of SEQ ID NO: 5.

SEQ ID NO: 7 is the amino acid sequence of the CDR2 of the variable light chain of SEQ ID NO: 5.

SEQ ID NO: 8 is the amino acid sequence of the CDR3 of the variable light chain of SEQ ID NO: 5.

SEQ ID NO: 9 is an amino acid sequence of the variable heavy chain of an antibody Clone 32 of the present disclosure.

SEQ ID NO: 10 is the amino acid sequence of the CDR1 of the variable heavy chain of SEQ ID NO: 9.

SEQ ID NO: 11 is the amino acid sequence of the CDR2 of the variable heavy chain of SEQ ID NO: 9.

SEQ ID NO: 12 is the amino acid sequence of the CDR3 of the variable heavy chain of SEQ ID NO: 9.

SEQ ID NO: 13 is an amino acid sequence of the variable light chain of an antibody Clone 32 of the present disclosure.

SEQ ID NO: 14 is the amino acid sequence of the CDR1 of the variable light chain of SEQ ID NO: 13.

SEQ ID NO: 15 is the amino acid sequence of the CDR2 of the variable light chain of SEQ ID NO: 13 SEQ ID NO: 16 is the amino acid sequence of the CDR3 of the variable light chain of SEQ ID NO: 13.

SEQ ID NO: 17 is an amino acid sequence of the variable heavy chain of an antibody Clone 64 of the present disclosure.

SEQ ID NO: 18 is the amino acid sequence of the CDR1 of the variable heavy chain of SEQ ID NO: 17.

SEQ ID NO: 19 is the amino acid sequence of the CDR2 of the variable heavy chain of SEQ ID NO: 17.

SEQ ID NO: 20 is the amino acid sequence of the CDR3 of the variable heavy chain of SEQ ID NO: 17. SEQ ID NO: 21 is an amino acid sequence of the variable light chain of an antibody Clone 64 of the present disclosure.

SEQ ID NO: 22 is the amino acid sequence of the CDR1 of the variable light chain of SEQ ID NO: 21.

SEQ ID NO: 23 is the amino acid sequence of the CDR2 of the variable light chain of SEQ ID NO: 21.

SEQ ID NO: 24 is the amino acid sequence of the CDR3 of the variable light chain of SEQ ID NO: 21.

SEQ ID NO: 25 is a nucleotide sequence of an exemplary nucleic acid encoding the variable heavy chain of SEQ ID NO: 1.

SEQ ID NO: 26 is a nucleotide sequence of an exemplary nucleic acid encoding the variable light chain of SEQ ID NO: 5.

SEQ ID NO: 27 is a nucleotide sequence of an exemplary nucleic acid encoding the variable heavy chain of SEQ ID NO: 9.

SEQ ID NO: 28 is a nucleotide sequence of an exemplary nucleic acid encoding the variable light chain of SEQ ID NO: 13.

SEQ ID NO: 29 is a nucleotide sequence of an exemplary nucleic acid encoding the variable heavy chain of SEQ ID NO: 17.

SEQ ID NO: 30 is a nucleotide sequence of an exemplary nucleic acid encoding the variable light chain of SEQ ID NO: 21.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. It should also be understood that the precise numerical values used in the specification and claims form additional embodiments of the invention, and are intended to include any ranges which can be narrowed to any two end points within the example ranges and values provided. Efforts have been made to ensure the accuracy of the numerical values disclosed herein. Any measured numerical value, however, can inherently contain certain errors resulting from the standard deviation found in its respective measuring technique.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. Also incorporated by reference is any supplemental information that was published along with any of the aforementioned publications, patents and patent applications. For example, some journal articles are published with supplemental information that is typically available online.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications, patents and patents applications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Before proceeding further with the description of the specific embodiments of the present disclosure, a number of terms will be defined.

Analyte

A compound or composition to be measured, the material of interest. The analyte is a member of a specific binding pair (sbp) and may be a ligand, which is mono- or polyvalent, usually antigenic or haptenic, and is a single compound or plurality of compounds which share at least one common epitopic or determinant site.

MTX Analyte

As used herein, the term "MTX analyte" refers to analytes having an antibody binding epitope which is common to MTX. Analytes included in the term "MTX analyte" include methotrexate (MTX), with low cross reactivity to 7-hydroxy MTX (7-OH MTX) and similar pteridinyl containing analogs.

Sample Suspected of Containing Analyte

Any sample which is reasonably suspected of containing analyte can be analyzed by the methods of the present disclosure. Such samples can include human, animal or man-made samples. The sample can be prepared in any convenient medium which does not interfere with the assay. Typically, the sample is an aqueous solution or a natural fluid, such as, but not limited to, urine, whole blood, serum, plasma, cerebral-spinal fluid, or saliva. In some instances, the sample is serum.

Measuring the Amount of Analyte

Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the present disclosure.

Synonyms for the phrase "measuring the amount of analyte" which are contemplated within the scope of the present disclosure include, but are not limited to, detecting, measuring, or determining analyte; detecting, measuring, or determining the presence of analyte; detecting, or determining the amount of analyte; and detecting, measuring or determining the concentration of analyte.

Member of a Specific Binding Pair

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. These will usually be members of an immunological pair such as antigen-antibody.

Ligand

Any organic compound for which a receptor naturally exists or can be prepared. For example, in one context of the present disclosure, the analyte is a ligand and the present disclosure provides methods for determining the amount or concentration of the analyte which is a ligand.

Receptor

A receptor is any compound or composition capable of recognizing a particular spatial and polar organization of a molecule. These organized areas of a molecule are referred to as epitopic or determinant sites. Illustrative naturally occurring receptors include antibodies and enzymes.

Epitope

"Epitope" is a molecular region on the surface of an antigen capable of eliciting an immune response and of combining with the specific antibody produced by such a response, also called determinant, antigenic determinant. In reference to a hapten (such as MTX) an antibody can be generated against the non-antigenic hapten molecule by conjugating the hapten to an immunogenic carrier. An antibody is then generated which recognizes an "epitope" defined by the hapten.

Linking Group

A linking group is a portion of a structure which connects two or more substructures. A linking group has at least one uninterrupted chain of atoms extending between the substructures. The atoms of a linking group are themselves connected by chemical bonds. The number of atoms in a linking group is determined by counting the atoms other than hydrogen.

Conjugate

A conjugate is a molecule comprised of two or more substructures bound together through a linking group to form a single structure. The binding can be made by connecting the subunits through a linking group. Within the context of the present disclosure, a conjugate can include a glucose-6-phosphate dehydrogenase (G6PDH) enzyme attached to a hapten, sbp member or analyte analog, such as a conjugate where a G6PDH mutant enzyme is used (e.g., recombinant G6PDH as described in U.S. Pat. Nos. 6,455,288, 6,090,567, and 6,033,890). Within the context of the present disclosure, G6PDH may also be referred to as an enzyme, such as a G6PDH enzyme, or a label, such as a G6PDH label. In some cases, a conjugate can include a label (e.g., a label protein) including, but not limited to, G6PDH, alkaline phosphatase, β-galactosidase, and horse radish peroxidase, or a chemical label such as a fluorescent, luminescent or colorimetric molecule attached to a hapten, sbp member or analyte analog.

Conjugation

Conjugation is any process where two subunits are linked together to form a conjugate. The conjugation process can be comprised of any number of steps, for example as described herein.

Hapten

Haptens are capable of binding specifically to corresponding antibodies, but usually do not themselves function as immunogens for preparation of the antibodies. Antibodies which recognize a hapten can be prepared against compounds comprised of the hapten linked to an immunogenic carrier.

Derivative

The term "derivative" refers to a chemical compound or molecule made from a parent compound by one or more chemical reactions.

Analog

The term "analog" is a compound having a structure similar to that of another compound, but differing from it in respect to a certain component. It can differ in one or more atoms, functional groups, or substructures, which are replaced with other atoms, groups, or substructures.

Label

A "label," "detector molecule," "reporter" or "detectable marker" is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. A label can be attached directly or indirectly by a linking group. Non-limiting examples of labels include radioactive isotopes (e.g., $^{125}$I), enzymes (e.g. β-galactosidase, peroxidase), G6PDH (e.g., mutant G6PDH, such as recombinant G6PDH as described in U.S. Pat. Nos. 6,455,288, 6,090,567, and 6,033,890), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

Immunogen

The term "immunogen" refers to a substance capable of eliciting, producing, or generating an immune response in an organism.

Immunogenic Carrier

An "immunogenic carrier," as used herein, is an immunogenic substance, commonly a protein, which can join at one or more positions with haptens, thereby enabling the production of antibodies that can specifically bind with these haptens. Examples of immunogenic carrier substances include, but are not limited to, proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Protein

The terms "protein", "polypeptide" and "peptide" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, polypeptides having modified peptide backbones, and fusion proteins.

Signal Producing System

The "signal producing system" is utilized in assays for analytes and may have one or more components, at least one component being a detectable label (e.g., G6PDH, such as a mutant G6PDH). The signal producing system generates a signal that relates to the presence or amount of analyte in a sample. The signal producing system includes all of the reagents required to produce a measurable signal. For purposes of the present disclosure, typically, the G6PDH or a label protein (e.g., alkaline phosphatase, β-galactosidase or horse radish peroxidase) is conjugated to a sbp member analogous to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, such as by measurement of electromagnetic radiation, e.g., by visual examination. In some instances, the signal producing system includes a chromophoric substrate and an enzyme label (e.g., mutant G6PDH enzyme), where chromophoric substrates are enzymatically converted to dyes which absorb light in the ultraviolet or visible region.

Isolated

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

Interference

"Interference" arises when a substance or process falsely impacts an assay result. Interference may be endogenous or exogenous. Endogenous interference could be substances present in a patient's sample. Exogenous interferences could be substances introduced into the patient's sample. Interference could be caused by haemolysis, icterus, and lipaemia.

Drug interference may be due to the parent drug, metabolite(s), or additives in the drug preparation.

Preanalytical interference could be from collection tube components, transportation and storage that affect determination of analytes.

Carryover interference typically occurs when analyte from a high concentration sample (or reagent) is incompletely removed by the analytical system's washing process, whether probe, mixer or cuvette washing.

$$\% \text{ Error (Interference)} = 100 \times \frac{\text{mean value TEST} - \text{mean value CONTROL}}{\text{mean value CONTROL}}$$

Cross-Reactivity

"Cross-reactivity" refers to the reaction of an antibody with an antigen that was not used to induce that antibody. "Cross-reactivity" may be determined in a quantitative immunoassay by establishing a standard curve using known dilutions of the target analyte. The standard curve is then used to calculate the apparent concentration of the interfering substance present in various known amounts in samples assayed under similar condition. The cross-reactivity is the apparent concentration divided by the actual concentration multiplied by 100.

$$\% \text{ Cross-reactivity} = 100 \times \frac{\text{mean value TEST} - \text{mean value CONTROL}}{\text{concentration of CROSS-REACTANT}}$$

Calibration and Control Material

The phrase "calibration and control material" refers to any standard or reference material containing a known amount of an analyte. A sample suspected of containing an analyte and the corresponding calibration material are assayed under similar conditions. The concentration of analyte is calculated by comparing the results obtained for the unknown specimen or sample containing known concentration of analyte with the results obtained for the standard. This is commonly done by constructing or generating a calibration curve.

Sensitivity

Is used in the sense of detection limit, i.e., the smallest amount of an analyte giving a signal that is distinguishable from the signal obtained in the absence of analyte.

Spike-Recovery

"Spike-recovery" refers to an assay measuring the amount of analyte (recovery) in a sample mixture compared to a known amount of the analyte added (spiked) to the sample mixture. The measuring the amount of analyte may be expressed in terms of concentration (ng/mL) or a percentage (%).

Substantial Change in Enzyme Activity

A change in activity of an enzyme sufficient to allow detection of an analyte when the enzyme is used as a label in an assay for the analyte. Typically, the enzyme's activity is reduced 10 to 100%, such as 20 to 99%, or 30 to 95%.

Inhibitory Antibody

An antibody capable of inhibiting the activity of an enzyme or an enzyme-ligand conjugate upon binding an epitope present on the enzyme. Such antibodies are distinguished from anti-ligand antibodies capable of inhibiting the enzyme activity of enzyme-ligand conjugates upon binding to the ligand.

Modulation

Figure 10:
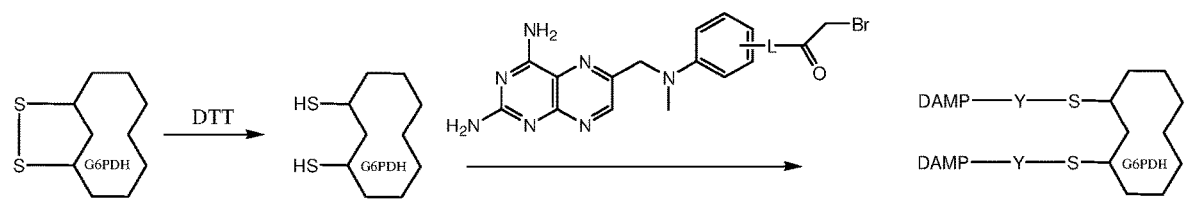
FIG. 10 shows the synthesis scheme for DAMP-Y-S-G6PDH, according to embodiments of the present disclosure.

In an assay experiment "modulation" refers to hapten or analyte attached to a label such as an enzyme and an analyte in a sample suspected of containing the analyte competing for analyte-antibody binding sites, thus modulating the amount of enzymatic product formed (see FIG. 10).

Maximum Inhibition

"Maximum inhibition" refers to an antibody capable of inhibiting the activity of an enzyme or an enzyme-ligand conjugate upon binding an epitope present on the enzyme when excess antibody is added to the assay and the signal obtained in the absence of analyte.

Ancillary Materials

Various ancillary materials will frequently be employed in an assay in accordance with the present disclosure. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

In certain aspects, the disclosure provides anti-MTX antibodies induced using an immunogen of this invention. Such antibodies could be used in detecting MTX in an immunoassay.

A MTX immunoassay of the disclosure is based on competition between MTX in the sample and a tracer, which is a labeled MTX analogue of the disclosure, for anti-MTX antibodies. In one embodiment, the immunoassay is a homogeneous enzyme immunoassay. Immunoassay kits are also provided.

A MTX analog of this invention is MTX derivatized to include a chemical moiety that facilitates attachment of a carrier or a label to the phenyl group of MTX that usually has the glutamic residue appended to aminomethylamino benzoyl moiety attached to the 2,4 diamino pteridine moiety. The MTX analogs of this invention are derivatized at the phenyl group through linkers substituted at ortho, meta or para positions to the N-10Me. The structure of MTX, showing the carbon numbering and the location of the benzoyl substituents, can be found hereinafter in, for example, FIG. 1.

Derivatizing the phenyl ring of the benzoyl moiety rather than the N-10Me group as described in U.S. Pat. No. 11,054,430 is advantageous, because the portion of the MTX analog available for antibody induction and recognition is distant from the MTX metabolite 7-hydroxy-MTX (7-OH MTX shown in FIG. 2). Thus, conjugation of a carrier through a linking group via the phenyl or benzoyl moiety of MTX produces an immunogen that elicits antibodies with minimal cross reactivity with 7-hydroxy-MTX.

Derivatization of MTX at the phenyl moiety preserving the diamino pteridine nucleus yield derivatives and haptens that are sufficiently immunologically similar to MTX so that antibodies induced by the analog react with both the analog and with MTX. Therefore, the MTX analogs of this invention that include a carrier are capable of inducing anti-MTX antibodies. In addition, the MTX analogs can be labeled for use as a tracer in an immunoassay, as described more fully hereinafter.

As is well known, drugs or other haptens can be derivatized to include a linking group with a chemical moiety that facilitates attachment of the hapten to a carrier or a label. Linking groups for preparing haptens are described in, Bioconjugation ed. Mohammed Aslam and Alastair Dent (McMillan References, London 1998).

Briefly, the bromoacetamides can be prepared as follows: an appropriately substituted phenyl group carrying a protected amine or carboxyl is appended to the 2,4-diamino-6-methyl-pteridinyl (DAMP) moiety to yield protected amine derivatives with varying linkers. Deprotection followed by acylation with an activated bromo acetic derivative yields the bromoacetamides of the current invention.

The linking group could be a maleimide, a vinyl sulfone that function as Michael acceptors to the thiol group acting as a nucleophile. The MTX analog (DAMP-Y) linking group can include a leaving group or a group that reacts with a nucleophile to yield an adduct. The leaving group is a chemical moiety that is active in conjugating the MTX analog to a label or a carrier. As part of the conjugation process, one or more atoms of the leaving group are given up. Furthermore, conjugation of a label or a carrier generally results in modifying the leaving group so that the linking group in the conjugate includes the residue following such modifications. For convenience herein, the term "linking group" refers to the linking group attached to DAMP to form a MTX analog and to the residue of the linking group following conjugation to a label or a carrier.

In several embodiments exemplified herein, DAMP-Y, MTX analogs are derivatized with a linking group (Y—Z) that includes a carboxyl group that is used to attach the analogs to a label or a carrier. In an exemplary conjugation process, the carboxyl group on the MTX analog is reacted with N-hydroxysuccinimide (NHS) to form an active ester. This active ester reacts with amino groups to form MTX analog conjugates. The amino groups can be present in small molecules such as fluorescein or biotin derivatives or in macromolecules such as proteins, for example, bovine serum albumin, keyhole limpet cyanin or peroxidase. In some cases, MTX conjugates containing a carrier or a label can be used as an immunogen or as a tracer, respectively.

In certain aspects, the present disclosure provides antibodies or antigen-binding fragments thereof that bind MTX and/or MTX analogs, such as the DAMP derivatives conjugated to another molecule. In some embodiments, the antibodies have a variable heavy chain amino acid sequence of SEQ ID NO: 1, or an amino acid sequence having at least 80%, such as at least 85%, at least 90%, at least 95%, or at least 99% sequence identity to the sequence of SEQ ID NO: 1. In some embodiments, the antibodies have a variable light chain amino acid sequence of SEQ ID NO: 5, or an amino acid sequence having at least 80%, such as at least 85%, at least 90%, at least 95%, or at least 99% sequence identity to the sequence of SEQ ID NO: 5. In some embodiments, the antibodies have a variable heavy chain amino acid sequence of SEQ ID NO: 9, or an amino acid sequence having at least 80%, such as at least 85%, at least 90%, at least 95%, or at least 99% sequence identity to the sequence of SEQ ID NO: 9. In some embodiments, the antibodies have a variable light chain amino acid sequence of SEQ ID NO: 13, or an amino acid sequence having at least 80%, such as at least 85%, at least 90%, at least 95%, or at least 99% sequence identity to the sequence of SEQ ID NO: 13. In some embodiments, the antibodies have a variable heavy chain amino acid sequence of SEQ ID NO: 17, or an amino acid sequence having at least 80%, such as at least 85%, at least 90%, at least 95%, or at least 99% sequence identity to the sequence of SEQ ID NO: 17. In some embodiments, the antibodies have a variable light chain amino acid sequence of SEQ ID NO: 21, or an amino acid sequence having at least 80%, such as at least 85%, at least 90%, at least 95%, or at least 99% sequence identity to the sequence of SEQ ID NO: 21.

In still other embodiments, an antibody or fragment thereof may be a monoclonal or polyclonal antibody. Depending on the methods of preparation, in certain embodiments, the antibodies of the present disclosure can be in a lyophilized state.

The antibodies used in the present disclosure can include immunoglobulin molecules and portions of immunoglobulin molecules capable of binding the desired binding site. The immunoglobulin molecules of the present disclosure can be essentially of any class or isotype (e.g., IgG, IgE, IgM, IgD, IgA and IgY) or subclass (e.g., IgG1, IgG2, IgG3, IgG4, IgA1 and IgA2) of an immunoglobulin molecule. Additionally, structures known as nanobodies and domain antibodies can be used, including polypeptides comprising a single or multiple CDRs of an antibody known to bind the cognate binding site, provided an effective amount of the binding ability is retained.

In certain aspects, an immunogen of the disclosure is a MTX analog that includes a carrier. The term "carrier" as used herein refers to a substance that is immunogenic in a selected host animal. Preparation of immunogens by linking a hapten to a carrier is well known. Selection of the carrier and administration route to induce an immune response varies depending on the host animal.

Carriers are generally large molecules, for example, polymers. In some cases, carriers are large proteins from a species other than that of the host animal. Bovine serum albumin (BSA) and keyhole limpet hemocyanin (KLH) are frequently used as carriers for inducing antibodies in mice, rats, goats, rabbits, chickens, and sheep. Additional carriers, such as proteins that are used to conjugate immunogens are well-known in the art and such embodiments are within the purview of the disclosure.

Exemplary preparations of immunogenic MTX analogs for inducing anti-MTX antibodies are described in the examples. In certain such exemplary immunogen preparations, R—Y is $(CH_2)_n$, CO—NH-(carrier), where n is from 1 to 12 and has one or more hetero atoms such as O, N, S. In some cases, n is 1 to 8, and the carrier is BSA.

The term "tracer" as used herein refers to a labeled analyte analog that can be used in a competitive immunoassay format. A tracer of disclosed herein is a MTX analog that includes a label which is attached to MTX through a linking group.

The term "label" is used to refer to substances that can be detected directly or indirectly. Labels that can be detected directly include, for example, a radionuclide or a fluorochrome. Labels can also be detected indirectly through one or more reactions. Such labels include enzymes that are detected by production of a signal, such as a colored product, chemiluminescence, fluorescence, or a radioactive product. Such enzyme labels and their signal development systems are well known. Other such labels include use of a member of a specific binding pair such as biotin/avidin. additional labels suitable for use in immunoassay procedures are well known and include, for example, enzymes, radionuclides, fluorochromes, dioxetanes, acridinium esters, lanthanides and metal chelates, biotin, and the like. In some cases, the label is a fluorochrome, acridinium ester, biotin or an enzyme such as HRP and G6PDH.

Suitable fluorochromes include dyes from the xanthene family e.g., fluoresceins and rhodamines (e.g., tetramethyl-rhodamine isothiocyanate-TRITC), phycoerythrin (PE), allophycocyanin (APC), Texas Red® (Thermo Fisher, Waltham), and preferably fluorescein. Although allophycocyanin and phycoerythrin are suitable fluorochromes, they cannot be used for fluorescence polarization immunoassays, because they are too large. Suitable fluoresceins include fluorescein isothiocyanate (FITC), (2-aminoethyl)-thioureido-fluorescein (FTED), fluorescein-thiosemicarbazide (FTSC), (2-aminoethyl)-ureido-fluorescein (FAMCO-E), erythrocin (tetra-iodo-fluorescein), fluoresceinamine (FAM) and their derivatives such as Oregon Green® and Tokyo Green®.

In certain embodiments, tracers having a fluorescein residue attached to the linking group through the 5-position of the fluorescein moiety are designated isomer I. Tracers having a fluorescein residue attached to the linking group through the 6-position of fluorescein are designated isomer II. For fluorescein and rhodamine-labeled tracers, little or none of the lactone form exists during fluorescence measurements and the carboxylated forms exist primarily as salts. The fluorochrome can be a homogeneous composition or a mixture of isomers. In addition, the fluorochrome can be used in its lactone form or as a biologically acceptable salt (e.g., Na, K, ammonium and similar salts) so that the fluorochrome can exist in its ionized state in the immunoassay.

Alternatively, carboxylic acids can be condensed with amines using other methods known in the art. Synthetic methods for formation of the amides of carboxylic acids are well known and are described in, The practice of peptide synthesis by M. Bodansky and A. Bodansky, ($2^{nd}$ ed. Springer-Verlag, New York 1995). Methods of making immunogenic conjugates are also described in Methods in Immunology and Immunochemistry (Cutris Williams, Academic Press 1977). Those references are incorporated by reference herein in their entireties. In addition, exemplary methods to produce MTX analogs useful as tracers or as immunogens are described in detail in the Examples section below. Certain exemplary MTX analogs useful as immunogens, tracers and specifically as enzyme conjugates are listed below in Table 3.

Broadly they are label free methods such as mass spectrometry or label based ones that are immunoassays using an antibody directed towards the analyte. Mass spectrometry method when coupled with chromatography, such as GCMS or LC-MS/MS provide high specificity. However, the GCMS or LC-MS/MS methods are time consuming, require specialized equipment, highly trained analysts, and extensive sample preparation, and are expensive. The methods also require sample volumes that are too large to be used in pediatric testing unless MTX concentrations are abnormally high. Briefly, mass spectrometry methods are not routinely used for MTX therapeutic drug monitoring in a typical clinical chemistry or hospital lab. Immunoassays have been developed for MTX based on heterogeneous requiring multiple wash steps or homogeneous formats that require a simple mix and read.

More recently, a competitive immunoassay (U.S. Pat. No. 11,054,430) has been developed for free MTX using antibodies that detect MTX but do not cross-react with DAMPA but still have cross reactivity to isolated 7-OH MTX. These antibodies were used in the competitive immunoassay and were developed against a particular immunogen linked through the N-10 (see FIG. 1 of U.S. Pat. No. 11,054,430). Haptens were used that are derivatives involving the chemical modification of the N-10 linked derivative of MTX. Antibodies were used to detect MTX and some selected with minimal cross reactivity to DAMPA, however there is still cross reactivity to 7-OH MTX and the method is heterogeneous requiring a wash and sensitivity is limited as the precision is compromised at the lower limit of quantitation. Other cross reactivities to folic, folinic, dihydrofolic, tetrahydrofolic and trimethoprim are higher than 0.1%.

An embodiment of the present disclosure provides a compound of Formula 1 shown below:

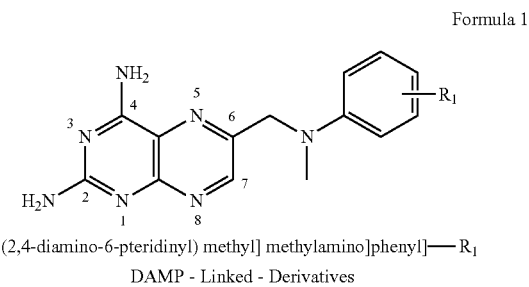

Formula 1

(2,4-diamino-6-pteridinyl) methyl] methylamino]phenyl]—$R_1$

DAMP - Linked - Derivatives wherein:
    $R^1$ is —Y—Z; and
    Y is a linking group and Z is selected from hydrogen, OH, SH, S-acyl, O-alkyl, halogen, $NH_2$, epoxy, maleimidyl, haloacetamide, carboxyl, activated carboxyl, an alkyne, an azide, an immunogenic carrier, a protein, and a label.

Aspects of the present disclosure include antibodies. In some embodiments, an antibody of the present disclosure specifically binds to any of the compounds of the present disclosure, including any of the compounds of Formula 1 described elsewhere herein.

Nucleic acids that encode any of the antibodies of the present disclosure are also provided, as are expression vectors comprising such nucleic acids, and cells comprising such nucleic acids and expression vectors.

The antibodies and enzymes disclosed herein may be used in various assays and methods that measure, quantify, and/or detect the presence of MTX in a sample. In some embodiments, a competitive assay format is used. In certain such formats, antibodies or enzymes may be attached to a solid support and are used to capture labeled and unlabeled MTX (when present in the sample).

In the absence of MTX in the sample, the labeled MTX would bind to the antibody/enzyme on the solid support, generating a signal. Free MTX in the sample would compete with the labeled MTX for the antibody/enzyme binding site, resulting in a decrease in signal. The signal is inversely proportional to the binding of the unlabeled MTX from the sample.

The antibodies and enzymes described herein can be combined with a sample to perform the assays. The sample may be a biological sample, such as tissue extracts, tissues used in immunohistochemistry, or fluids. The fluid samples may be derived from blood, plasma, serum, or buffer.

The antibodies and enzymes described herein may be linked or bound to various components or moieties in order to perform assay functions. For example, in some embodiments, the antibodies and enzymes discussed herein may be bound directly through covalent or non-covalent attachment, or indirectly to a solid support or carrier to form a capture molecule. When bound indirectly, intermediate linkers may be used to bind the components. Suitable intermediate linkers include, but are not limited to, an amino group or a carboxylate group or a thiol, biotin, ligands, or other chemical bonds. Suitable solid supports or carriers include, but are not limited to, glass surfaces (e.g., a glass slide or bead), plastic surfaces, metal surfaces, polystyrene surfaces (e.g., a bead or a plate), nitrocellulose surfaces, microparticles, nano-particle surfaces, plates, wells, and paramagnetic or magnetic beads that may be coated with avidin or streptavidin or have other surface functionalities to promote binding affinity.

In some embodiments, labeled MTX is used in the competitive assay format. In certain embodiments, some of the MTX may be linked or bound, directly through covalent or non-covalent attachment, or indirectly, to a label to form a labeled MTX. When bound indirectly, intermediate linkers may be used as discussed herein.

As stated, in some embodiments, an antibody or fragment thereof or an aptamer may be bound to a solid support to form a capture molecule during an assay or method of the present disclosure. This binding can be performed before or after contacting the sample with the antibody or fragment thereof or aptamer. The antibody or fragment thereof or aptamer can be bound to a solid support directly (e.g., covalently) or indirectly (e.g., using binding partners).

Similarly, in some embodiments, MTX molecule may be bound to a label to form a labeled MTX during an assay or method of the present disclosure. This binding can be performed before or after contacting MTX with the sample. MTX can be bound to a label directly (e.g., covalently) or indirectly (e.g., using binding partners).

Examples of suitable binding partners include, but are not limited to, biotin/streptavidin; antibody/antigen; antibody/Fc receptor; an antibody of a first species and an antibody of a second species against first species antibodies; Fc/Fc receptor; 6-His/$Ni^{2+}$; 6-His/cobalt; and 6-His/divalent cation resin.

In other embodiments, binding pairs can be streptavidin and biotin or two antibodies that bind each other such as an antibody that binds an Fc portion of another antibody. In other embodiments, the binding may occur through the interaction between numerous binding pairs. It is contemplated that essentially any method can be used that results in the binding of the antibody to the solid support or binding MTX to a label, e.g., directly or indirectly. In some embodiments, an antibody comprises biotin and a solid support comprises streptavidin or vice versa.

In some embodiments, the label may be any label that corresponds to a suitable detection method. Suitable detection modes include, but are not limited to, absorbance, fluorescence or luminescence using labels or compounds, chemiluminescent compounds, enzyme labels, fluorophores, chromogenic compounds, radiolabels, catalysts, colorimetric compounds or labels, labeled antibodies, latex particle, a magnetic particle, a radioactive element, fluorescent dyes, phosphorescent dyes, lanthanides, gold particles, silver colloidal particles, selenium colloidal particles, metal chelates, ferrocenes, coenzymes, electro active groups, oligonucleotides or stable radicals. The metal chelate may be a ruthenium for electrochemiluminescence, an osmium metal chelate or a lanthanide such as europium, samarium or terbium chelate for time resolved fluorescence. The detection method may include any known detection method including, but not limited to, chromogenic, radioisotopic, fluorescence, immunofluorescence, luminescence, bioluminescence, electrochemiluminescence (ECL), amperometric measurements involving current or impedance, Surface Enhanced Raman Scatter (SERS) and surface plasmon resonance (SPR).

In some embodiments, the detection method may be absorbance that is read in an endpoint or kinetic mode. A colorimetric compound may serve as the label that may be detected or quantified within a cuvette, reaction chamber, such as in a flow cell, or on a disposable container or a lateral flow strip. The solid support may serve to hold the antibody bound to the label near an electrode in the electrochemical readout reaction chamber during detection. The solid support could be a lateral flow device or a surface plasmon generating surface.

In some embodiments, the solid support and/or the label may be from a lyophilized composition that is rehydrated with the sample for use in an assay. The lyophilized composition may contain standard and/or other necessary assay specific components of an assay, such as buffers, reagents, detergents, preservatives, salts, proteins, antibodies, etc. It is contemplated that the solid support and the label may be lyophilized in separate compositions, and then rehydrated with the sample. It is also contemplated that the solid support and the label may be lyophilized in the same composition, and then rehydrated with the sample.

The antibodies and enzymes of the present disclosure may be used in various assay formats, including, for example, heterogeneous immunoassays such as enzyme-linked immunosorbent assays (ELISA) or ECL assays for detecting the presence of MTX or homogeneous immunoassays such as EMIT, CEDIA, LOCI or turbidimetric formats such as QMS (Thermo Fisher), PETIA (Abbott) or KIMs (Roche) that require no wash steps to separate bound and free moieties. In one aspect of the present disclosure, the assay method steps for detecting and/or quantifying MTX in a sample may include combining in a solution the sample with a capture molecule and a labeled MTX, wherein the capture molecule is capable of binding the labeled MTX, and wherein MTX, when present in the sample, competes with the labeled MTX for binding to the capture molecule; and detecting an amount of labeled MTX bound to the capture molecule through signal produced by a label on the bound labeled MTX, wherein the signal is inversely proportional to the amount of MTX present in the sample.

In some embodiments, the capture molecule comprises an antibody or fragment thereof attached to a solid support. In some embodiments, a capture molecule can be an antibody or fragment thereof attached to a solid support, where the antibody or fragment thereof binds MTX and/or MTX conjugated to another molecule(s). For example, the antibody may selectively bind to a molecule conjugated to MTX as compared to the same molecule without conjugation to MTX. When an antibody is described as binding to MTX it is understood that this also includes an antibody that selectively binds a molecule conjugated to MTX as compared to the same molecule without conjugation to MTX.

In some embodiments, the labeled MTX comprises a MTX molecule, or MTX conjugated to another molecule, covalently linked to a label. In some embodiments, the labeled MTX comprises a MTX conjugate covalently linked to a label.

In some embodiments, the conjugate of the MTX analog DAMP is a DAMP derivative modified at the phenyl ring of Formula 1. Modifications of the phenyl ring could be through an alkyl, carbonyl, heteroatom such as O, N and S. In some embodiments, the conjugate of the MTX analog DAMP is a MTX derivative modified at the gamma (γ)-position of the carboxyl group of MTX either chemically or naturally.

It is contemplated that the steps of the methods of the present disclosure do not have to be completed in the order provided herein, and may be performed in different orders. Additionally, the sample may be incubated for a period of time before a washing step and removal of any unbound or excess materials. It is further contemplated that additional washing steps to remove materials during the assay may be performed at additional times during the method, such as after the addition of each assay component and/or before the detecting step.

In other embodiments, a capture molecule and sample are combined prior to the addition of a labeled MTX. For example, a solution comprising a sample and a capture molecule may be incubated for a period of time prior to the addition of a labeled MTX.

Components/reagents used in embodiments of the assays disclosed herein can be lyophilized using standard lyophilization methods. For example, the components and reagents can be lyophilized by creating a solution containing the desired component(s), such as a labeled MTX or capture molecule. Then the solution can be used to form drops that are allowed to fall into a freezing medium (e.g., liquid nitrogen), typically forming frozen spheres, and then lyophilizing the frozen spheres or pellets.

In some embodiments of the assays, a lyophilized composition containing a capture molecule or a labeled MTX or both is rehydrated with the sample. This embodiment may be advantageous in that the sample is essentially undiluted during the assay, which may result in higher levels of sensitivity because more MTX is present in an undiluted sample as compared to a diluted sample of the same volume. In some embodiments, a sample is diluted prior to combining with the other reagents. In some embodiments, a sample is not diluted prior to combining with the other reagents.

Also provided are methods of making the antibodies of the present disclosure. The methods include culturing a cell of the present disclosure under conditions suitable for the cell to express the antibody, wherein the antibody is produced.

Aspects of the present disclosure further include compositions. A composition of the present disclosure may include any of the antibodies, nucleic acids, expression vectors, and/or cells of the present disclosure.

Also provided are methods for determining an amount of at least one MTX analyte in a medium. In certain embodiments, such methods include combining in a medium a sample suspected of containing at least one MTX analyte, and an antibody of the present disclosure. Such methods further include determining the presence or absence of a complex comprising the MTX analyte and the antibody, wherein the presence of the complex indicates the presence of the MTX analyte in the sample.

Aspects of the present disclosure further include kits. According to some embodiments, the kits find use in determining an amount of at least one MTX analyte in a sample. In certain embodiments, a kit of the present disclosure includes any of the antibodies of the present disclosure, and instructions for using the antibody to determine an amount of at least one MTX analyte in a sample. Such kits may further include any of the compounds of Formula 1 of the present disclosure. According to some embodiments, a kit of the present disclosure includes any of the compounds of Formula 1 of the present disclosure, and instructions for using the compound to determine an amount of at least one MTX analyte in a sample. Such kits may further include any of the antibodies of the present disclosure.

Compounds, Conjugates and Syntheses Thereof

Homogeneous enzyme immunoassays depend on the availability of enzyme-sbp member conjugates whose enzyme activity can be strongly modulated on binding of the sbp partner. The present disclosure provides enzyme-sbp member conjugates and antibodies for conducting assays that are useful in homogeneous immunoassays.

In certain embodiments, protein immunogens are synthesized and used to prepare antibodies specific for compounds, such as MTX analyte. The antibodies may be used in methods for detecting MTX analyte in a sample suspected of containing the analyte. Label conjugates are prepared and may be employed in the above methods. Effective quantitation of samples for the presence of MTX analyte as referred to above may be realized.

The immunogens and label conjugates may involve an analog of MTX linked through the phenyl group to a protein or a label. In some instances, the conjugate may be referred to herein as a protein conjugate or a label conjugate, respectively.

Compounds of the present disclosure include compounds useful for producing antibodies according to the present disclosure. In addition, compounds of the present disclosure include conjugates useful for the immunoassays described herein. In certain embodiments, the compounds include a compound of Formula 1:

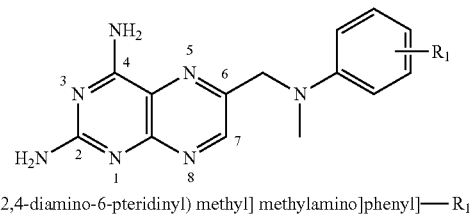

(2,4-diamino-6-pteridinyl) methyl] methylamino]phenyl]—R₁

DAMP - Linked - Derivatives wherein:

R¹ is —Y—Z;

Y is a linking group; and

Z is selected from the group consisting of hydrogen, OH, SH, S-acyl, O-alkyl, O-sulfonate, halogen, NH₂, epoxy, maleimidyl, haloacetamide, carboxyl, activated carboxyl, azide, alkene, an immunogenic carrier, a protein, and a label, and salts thereof.

In some embodiments, Z is a protein. For example, the protein can be an immunogenic carrier. The immunogenic carrier can be conjugated to a MTX hapten, thereby enabling the production of antibodies that can specifically bind with the hapten. For example, the immunogenic carrier can be selected from a hemocyanin, a globulin, an albumin, and a polysaccharide. In some instances, the immunogenic carrier is bovine serum albumin (BSA). In some instances, the immunogenic carrier is keyhole limpet hemocyanin (KLH). In certain embodiments, the immunogenic carrier may be modified to include one or more functional groups. The functional group on the modified immunogenic carrier can be a reactive functional group that facilitates attachment of the immunogenic carrier to the linking group in the compound of Formula 1.

In some embodiments, a 2,4-diamino-6-aminomethyl-pteridinyl phenyl (DAMP) hapten is linked through an alkyl, ether, thioether, azo, keto or alkene functionality. As such, in some cases, the linking group comprises an alkyl or substituted alkyl group attached to the phenyl group of the pteridinyl methylamino moiety.

In certain embodiments, such haptens are used to produce antibodies specific for MTX.

In certain embodiments, Z is a label. The label is a molecule which produces, or can be induced to produce, a detectable signal. For example, the label can be an enzyme, such as an enzyme selected from an alkaline phosphatase, a β-galactosidase and a horse radish peroxidase. In some embodiments, the label is an enzyme, where the enzyme is glucose-6-phosphate dehydrogenase (G6PDH). In some instances, the G6PDH is a mutant G6PDH, which includes one or more amino acid residue substitutions relative to the wild-type form. For example, the mutant G6PDH can include a cysteine substitution, e.g., a cysteine substitution in each subunit of the G6PDH enzyme. In some cases, the linking group can be attached to the G6PDH enzyme at the cysteine residue. In certain embodiments, the label may be modified to include one or more functional groups. The functional group on the modified label can be a reactive functional group that facilitates attachment of the label to the linking group in the compound of Formula 1.

Figure 2:
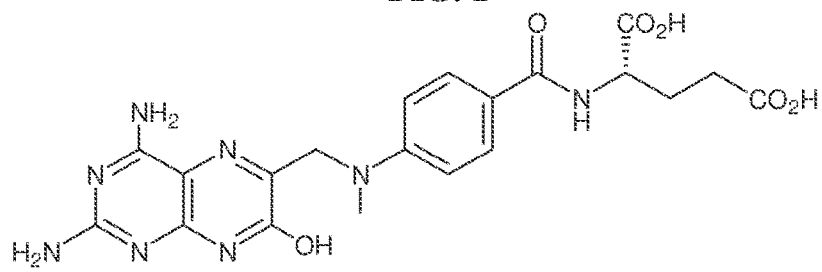
FIG. 2 shows the chemical structures of the metabolites DAMPA and 7-OH MTX.
Figure 2:
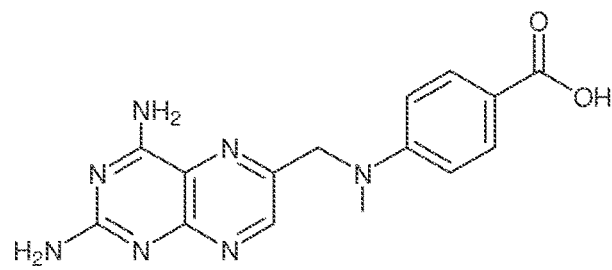

In some embodiments, a MTX analog is derived from the acylated phenyl ring ortho, meta or para to the MTX (FIG. 2). As such, in some cases, the linking group comprises an acyl or substituted acyl group attached to the phenyl ring of the 2,4-diamino-6-aminomethyl-pteridinyl phenyl (DAMP) portion (i.e., attached to the $R^1$-phenyl ring). In certain embodiments, such derivatives are used to produce conjugates useful in the immunoassays described herein.

In certain embodiments, Z is a protein. The protein can be any suitable protein, which includes amino acid residues, such as a dipeptide, tripeptide, and the like, in any number of such amino acid residues, such as 2 or more, 3 or more, 4 or more, 5 or more, 6 or more, 7 or more, 8 or more, 9 or more, 10 or more, etc. In certain embodiments, the protein may be modified to include one or more functional groups. The functional group on the modified protein can be a reactive functional group that facilitates attachment of the protein to the linking group in the compound of Formula 2. In some instances, the protein is acylated. In some instances, the protein is alkylated.

The linking group may include about 1 to 25 atoms (excluding hydrogen atoms) and may include a chain of from 2 to 15 atoms (excluding hydrogen atoms), each independently selected from carbon, oxygen, sulfur, nitrogen, halogen and phosphorous. In some embodiments, the linking group includes 1 to 15 carbon atoms and/or 0 to 6 heteroatoms. Examples of linking groups include, but are not limited to, $-(CH_2)_nC(O)-$, $-C(O)(CH_2)_n-$, $-C(O)(CH_2)_nNHC(O)-$, $-C(O)(CH_2)_nNHC(O)(CH_2)_n-$, $-(CH_2)_nSCH_2C(O)-$, $-(CH_2)_nC(O)NH(CH_2)_n-$, $-(CH_2)_nNHC(O)-$, $-(CH_2)_nNHC(O)(CH_2)_n-$, $-(CH_2)_nNHC(O)(CH_2)_nO(CH_2)_nNHC(O)(CH_2)_n-$, $-(CH_2)_nNHC(O)(CH_2)_nNHC(O)(CH_2)_n-$, $-NH(CH_2)C(O)-$, $-(CH_2)_n-$, $-C(O)NH(CH_2CH_2O)_m(CH_2)_nNHC(O)(CH_2)_n-$, and $-(CH_2)_n(heterocyclyl)S(CH_2)_nC(O)-$, each m is independently an integer from 1 to 10, and each n is independently an integer from 1 to 10, and including salts thereof. In certain embodiments, the linking group is $-C(O)NH(CH_2CH_2O)_2(CH_2)_2NHC(O)CH_2-$. In certain embodiments, the linking group is $-CH_2NHC(O)(CH_2)_7NHC(O)CH_2-$. In certain embodiments, the linking group is $-CH_2NHC(O)(CH_2)_2O(CH_2)_4NHC(O)CH_2-$. In certain embodiments, the linking group is $-CH_2NHC(O)(CH_2)_2NHC(O)CH_2-$. In certain embodiments, the linking group is $-CH_2NHC(O)CH_2-$. In certain embodiments, the linking group is $-C(O)(CH_2)_nNHC(O)(CH_2)_n-$, such as $-C(O)(CH_2CH_2)NHC(O)(CH_2)-$. In certain embodiments, the linking group is $-(CH_2)_n(heterocyclyl)S(CH_2)_nC(O)-$, such as $-(CH_2CH_2CH_2CH_2)(2,5-dioxopyrrolidin-1-yl)S(CH_2)C(O)-$.

The number of heteroatoms in the linking group may range from 0 to 6, such as from about 1 to 5, or from 2 to 5, or from 3 to 5. The linking agents may be aliphatic or aromatic. When heteroatoms are present, oxygen may be present as oxo or oxy, bonded to carbon, sulfur, nitrogen or phosphorous; nitrogen may be present as nitro, nitroso or amino, bonded to carbon, oxygen, sulfur or phosphorous; sulfur can be analogous to oxygen; phosphorous can be bonded to carbon, sulfur, oxygen or nitrogen, such as phosphonate and phosphate mono or di-ester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

In certain embodiments, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities can be linked to amine groups, carboxyl groups, active olefins, alkylating agents, e.g., bromoacetyl. Where an amine and carboxylic acid or its nitrogen derivative or phosphoric acid is linked, amides, amidines and phosphoramides can be formed. Where mercaptan and activated olefin are linked, thioethers can be formed. Where a mercaptan and an alkylating agent are linked, thioethers can be formed. Where aldehyde and an amine are linked under reducing conditions, an alkylamine can be formed. Where a carboxylic acid or phosphoric acid and an alcohol are linked, esters can be formed. Various linking groups are described, see, for example, Cautrecasas, *J. Biol. Chem.* (1970) 245:3059.

To develop an assay for MTX, the chemical structure of MTX that conserves the 2,4 diamino pteridinyl methylaminomethyl phenyl (DAMP) moiety is used. For example, MTX has several nitrogen atoms as part of the pteridine nuclei as well as aminomethyl group (N-10 used in U.S. Pat. No. 10,054,430). (see Formula 1 for numbering). The alkyl and acyl linked derivatives from the phenyl moiety preserve the core diamino pteridinyl methyl aminomethyl (DAMP)

structure. The specific linkage through the phenyl group generates chemical structures that retain significant MTX complementarity to prepare immunogens and raise antibodies accordingly.

The present disclosure provides for the design of MTX haptens and immunogens by modification of the glutamate portion of MTX. Haptens derived from the MTX analog s DAMP 1, 2, 3, 4, 5 and –6 of the present disclosure and their synthesis are shown in FIG. 4-15. Placement of a linking group at the phenyl ring provides for antibodies that may specifically react with MTX analyte because the analytes share the pteridinyl amino methylamino phenyl group. The present disclosure thus provides MTX analogs and immunogens useful with the various types of immunoassays described herein.

Compounds useful for producing antibodies and conjugates according to the present disclosure can be synthesized in accordance with the general synthetic methods described below. Compounds of Formula 1 can be prepared by standard methods. The following reaction schemes are only meant to represent examples of the methods and are in no way meant to limit the present disclosure.

A) Haptens

Addition and removal of protecting group, such as tert-butoxy carbonyl (Boc) is usually performed to protect an amino group for subsequent acylation with an activated haloacetic derivative. Suitable protecting groups are described in detail in patents and articles in the technical literature. See, for example, "Principles of Peptide Synthesis" (M. Bodanszky, Springer Verlag, Berlin, Heidelberg, New York, Tokyo (1984)). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentylethoxycarbonyl, bromobenzyloxy, carbamyl, formyl, and the like. The particular protecting group chosen may depend on the nature of the reaction to be performed and the conditions of such reaction such as temperature, pH, and so forth.

b) Immunogen

Functionalized haptens (e.g. DAMP 1-6, MTX, DAMPA) may be conjugated to proteins. Haptens containing a carboxyl group can be directly coupled to the epsilon amino groups of lysine in proteins. The haloacetamides can be coupled to thiols usually by a two step procedure. Activation of protein lysine residues by acylation of the epsilon-nitrogen with N-succinimidyl S-acetylthioacetate (SATA), followed by subsequent hydrolysis of the S-acetyl group with hydroxylamine produces a nucleophilic sulfhydryl group. Conjugation of the sulfhydryl activated protein with the bromoacetamide derivatized hapten proceeds via nucleophilic displacement of the bromide to create a thioether linked conjugate. Suitable proteins (immunogenic carriers) include, but are not limited to, keyhole limpet hemocyanin, bovine thyroglobulin, and ovalbumin.

The MTX analogs includes the bromoacetamide functionality for thiol modification of thiol containing proteins. The synthesis of MTX immunogen DAMP-L-S-KLH with a linking group (L) on the phenyl ring of the MTX analog DAMP begins with the synthesis of DAMP-Y as shown in FIGS. 4-10, the preparation of which is described in Examples 1-6. Reaction of amines from keyhole limpet hemocyanin (KLH) with N-succinimidyl S-acetylthioacetate can produce protected sulfhydryls that can be subsequently deprotected by hydroxylamine for reaction with DAMP-bromoacetamides of the current invention. Reaction of thiol modified KLH-SH with DAMP-bromoacetamides in sodium phosphate (0.1 M, pH 8.0) buffer solution can produce the desired immunogen DAMP-Y-S-KLH as show in FIG. 11. The immunogen DAMP-Y-S-KLH can be purified by chromatography, such as on a Sephadex G-25 column with buffer solution. The concentration of immunogen DAMP-Y-S-KLH can be measured using a protein assay, such as, but not limited to a Pierce™ Rapid Gold BCA protein assay kit. The immunogen DAMP-Y-S-KLH can be used for the immunization of rabbits for antibody production.

c) Enzyme Conjugate

Haptens DAMP-L of the present invention with bromoacetamide functionality can be used for reaction with proteins containing a thiol group. Conjugation of DAMP-Y bromoacetamides to cysteine containing G6PDH is shown in FIG. 10, the preparation of which is described in Example 15

Haptens derived from DAMP-Y can be used to prepare immunogen. Hapten DAMP-Y (1-6) can be used to prepare a G6PDH conjugate. The immunogen DAMP-L-S-KLH can be used for elicitation of antibodies. In certain embodiments, in an enzyme-based assay format, antibodies produced can show good modulation with a MTX analyte. In some embodiments, the immunogen DAMP-Y-S-KLH can be used to successfully raise antibodies, which may provide an indication that such antibodies have potential use in an enzyme-based MTX immunoassay as described hereinafter.

Antibodies and Preparation Thereof

Aspects of the present disclosure include antibodies, which specifically bind to MTX. In some embodiments, an antibody of the present disclosure specifically binds to any of the compounds of the present disclosure, including any of the compounds of Formula 1 described elsewhere herein.

The term "antibody" (also used interchangeably with "immunoglobulin") encompasses polyclonal (e.g., rabbit polyclonal) and monoclonal antibody preparations where the antibody may be an antibody or immunoglobulin of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies (e.g., scFv); fragments of antibodies (e.g., fragments of whole or single chain antibodies) which retain specific binding to the compound, including, but not limited to single chain Fv (scFv), Fab, (Fab')$_2$, (scFv')$_2$, and diabodies; chimeric antibodies; monoclonal antibodies, human antibodies; and fusion proteins comprising an antigen-binding portion of an antibody and a non-antibody protein. In some embodiments, the antibody is selected from an IgG, Fv, single chain antibody, scFv, Fab, F(ab')$_2$, or Fab'. The antibodies may be further conjugated to other moieties, such as members of specific binding pairs, e.g., biotin (member of biotin-avidin specific binding pair), and the like.

Immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (usually of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 150 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, (1991 and Lefranc et al. IMGT, the international ImMunoGeneTics information System®. Nucl. Acids Res., 2005, 33, D593-D597)). A detailed discussion of the IMGT system, including how the IMGT system was formulated and how it compares to other systems, is provided on the World Wide Web at imgt.cines.fr/textes/IMGT ScientificChart/Numbering/IMGTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to IMGT, supra, unless otherwise indicated.

An "antibody" thus encompasses a protein having one or more polypeptides that can be genetically encodable, e.g., by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies encompass intact immunoglobulins as well as a number of well characterized fragments which may be genetically encoded or produced by digestion with various peptidases. Thus, for example, pepsin digests an antibody below the disulfide linkages in the hinge region to produce F(ab)'$_2$, a dimer of Fab which itself is a light chain joined to VH-CHI by a disulfide bond. The F(ab)'$_2$ may be reduced under mild conditions to break the disulfide linkage in the hinge region thereby converting the (Fab')$_2$ dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, scFv, dAb, nanobodies, unibodies, and diabodies. In certain embodiments, an antibody of the present disclosure is selected from an IgG, Fv, single chain antibody, scFv, Fab, F(ab')$_2$, and Fab'.

The phrases "specifically binds," "specific for," "immunoreactive," "immunoreactivity," and "antigen binding specificity," when referring to an antibody, refer to a binding reaction with an antigen which is highly preferential to the antigen or a fragment thereof, so as to be determinative of the presence of the antigen in the presence of a heterogeneous population of antigens. Thus, under designated immunoassay conditions, the specified antibodies bind to a particular antigen and do not bind in a significant amount to other antigens present in the sample. Specific binding to an antigen under such conditions may require an antibody that is selected for its specificity for a particular antigen. For example, the antibodies may specifically bind to the compound, and do not exhibit comparable binding to other molecules present in a sample.

In some embodiments, an antibody of the present disclosure "specifically binds" to the compound if it binds to or associates with the compound with an affinity or $K_a$ (that is, an equilibrium association constant of a particular binding interaction with units of 1/M) of, for example, greater than or equal to about 105 $M^{-1}$. In certain embodiments, the antibody binds to the compound with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, 101 $M^{-1}$, $10^{12}$ $M^{-1}$, or $10^{13}$ $M^{-1}$. "High affinity" binding refers to binding with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater. Alternatively, affinity may be defined as an equilibrium dissociation constant ($K_D$) of a particular binding interaction with units of M (e.g., $10^{-5}$ M to $10^{-13}$ M, or less). In some embodiments, specific binding means the antibody binds to the compound with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. The binding affinity of the antibody for the compound can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by Bioluminescence Interferometry (BLI, ForteBio), by radioimmunoassay; or the like.

Whether a first antibody "competes with" a second antibody for binding to the compound may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is then added. One of the two antibodies is labelled. If the labeled antibody and the unlabeled antibody bind to separate and discrete sites on the compound, the labeled antibody will bind to the same level whether or not the suspected competing antibody is present. However, if the sites of interaction are identical or overlapping, the unlabeled antibody will compete, and the amount of labeled antibody bound to the compound will be lowered. If the unlabeled antibody is present in excess, very little, if any, labeled antibody will bind.

For purposes of the present disclosure, competing antibodies are those that decrease the binding of an antibody to the compound by about 50% or more, about 60% or more, about 70% or more, about 80% or more, about 85% or more, about 90% or more, about 95% or more, or about 99% or more. Details of procedures for carrying out such competition assays are well known in the art and can be found, for example, in Harlow and Lane, Antibodies, A Laboratory Manual, Cold Spring Harbor Laboratory Press, Cold Spring Harbor, New York, 1988, 567-569, 1988, ISBN 0-87969-314-2. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the plate may be titrated. The results may be plotted, and the concentrations necessary to achieve the desired degree of binding inhibition may be compared.

According to some embodiments, an antibody of the present disclosure competes for binding to the compound of Formula 1 with an antibody comprising:
A variable heavy chain ($V_H$) polypeptide comprising:
  a $V_H$ CDR1 comprising the amino acid sequence RSDHWIC (SEQ ID NO: 2),
  a $V_H$ CDR2 comprising the amino acid sequence CIYIGSGTFVRSGTTYYASWAKG (SEQ ID NO: 3), and
  a $V_H$ CDR3 comprising the amino acid sequence GFYATDGYGGPSYLNL (SEQ ID NO: 4); and
a variable light chain ($V_L$) polypeptide comprising:
  a $V_L$ CDR1 comprising the amino acid sequence QASESISSYCS (SEQ ID NO: 6),
  a $V_L$ CDR2 comprising the amino acid sequence RASTLES (SEQ ID NO: 7), and
  a $V_L$ CDR3 comprising the amino acid sequence QSYAYSSPDSYGST (SEQ ID NO: 8).

In certain embodiments, such an antibody comprises the six CDRs set forth in SEQ ID NO: 2, SEQ ID NO: 3, SEQ ID NO: 4, SEQ ID NO: 6, SEQ ID NO: 7, and SEQ ID NO: 8. According to some embodiments, the antibody comprises: a variable heavy chain ($V_H$) polypeptide comprising an amino acid sequence having 70% or greater, 75% or greater, 80% or greater, 85% or greater, 90% or greater, or 95% or greater identity to the amino acid sequence set forth in SEQ ID NO: 1; and a variable light chain ($V_L$) polypeptide comprising an amino acid sequence having 70% or greater, 75% or greater, 80% or greater, 85% or greater, 90% or greater, or 95% or greater identity to the amino acid sequence set forth in SEQ ID NO: 5.

In some cases, antibodies comprise the three heavy chain CDRs as set forth in SEQ ID NOs: 2 to 4 and have amino acid substitutions in the sequence of SEQ ID NO: 1 outside the CDRs such that the resulting $V_H$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 1. Similarly, in some cases, antibodies comprise the three heavy chain CDRs as set forth in SEQ ID NOs: 6 to 8 and have amino acid substitutions in the sequence of SEQ ID NO: 5 outside the CDRs such that the resulting $V_L$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 5. According to some embodiments, an antibody of the present disclosure competes for binding to the compound of Formula 1 with an antibody comprising:
a variable heavy chain ($V_H$) polypeptide comprising:
  a $V_H$ CDR1 comprising the amino acid sequence SSDHWIC (SEQ ID NO: 10),
  a $V_H$ CDR2 comprising the amino acid sequence CIYIGSGTFVSSGTTYFASWAKG (SEQ ID NO: 11), and
  a $V_H$ CDR3 comprising the amino acid sequence GFYYTDGSGGPSYLNL (SEQ ID NO: 12); and
a variable light chain ($V_L$) polypeptide comprising:
  a $V_L$ CDR1 comprising the amino acid sequence QASQTIYSYLS (SEQ ID NO: 14),
  a $V_L$ CDR2 comprising the amino acid sequence SASTLAS (SEQ ID NO: 15), and
  a $V_L$ CDR3 comprising the amino acid sequence QSYMYSSSSFGST (SEQ ID NO: 16).

In certain embodiments, such an antibody comprises the six CDRs set forth in SEQ ID NO: 10, SEQ ID NO: 11, SEQ ID NO: 12, SEQ ID NO: 14, SEQ ID NO: 15, and SEQ ID NO: 16. According to some embodiments, the antibody comprises: a variable heavy chain ($V_H$) polypeptide comprising an amino acid sequence having 70% or greater, 75% or greater, 80% or greater, 85% or greater, 90% or greater, or 95% or greater identity to the amino acid sequence set forth in SEQ ID NO: 9; and a variable light chain ($V_L$) polypeptide comprising an amino acid sequence having 70% or greater, 75% or greater, 80% or greater, 85% or greater, 90% or greater, or 95% or greater identity to the amino acid sequence set forth in SEQ ID NO: 13.

In some cases, antibodies comprise the three heavy chain CDRs as set forth in SEQ ID NOs: 10 to 12 and have amino acid substitutions in the sequence of SEQ ID NO: 9 outside the CDRs such that the resulting $V_H$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 9. Similarly, in some cases, antibodies comprise the three heavy chain CDRs as set forth in SEQ ID NOs: 14 to 16 and have amino acid substitutions in the sequence of SEQ ID NO: 13 outside the CDRs such that the resulting $V_L$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 13.

According to some embodiments, an antibody of the present disclosure competes for binding to the compound of Formula 1 with an antibody comprising:
a variable heavy chain ($V_H$) polypeptide comprising:
  a $V_H$ CDR1 comprising the amino acid sequence KYYMT (SEQ ID NO: 18),
  a $V_H$ CDR2 comprising the amino acid sequence VTWSGGMTYYASWAKG (SEQ ID NO: 19), and
  a $V_H$ CDR3 comprising the amino acid sequence ERDYFDGYIGNDI (SEQ ID NO: 20); and
a variable light chain ($V_L$) polypeptide comprising:
  a $V_L$ CDR1 comprising the amino acid sequence QSSQSVWSRHLS (SEQ ID NO: 22),
  a $V_L$ CDR2 comprising the amino acid sequence KASTLAS (SEQ ID NO: 23), and
  a $V_L$ CDR3 comprising the amino acid sequence LGGYTCIRDDCRA (SEQ ID NO: 24).

In certain embodiments, such an antibody comprises the six CDRs set forth in SEQ ID NO: 18, SEQ ID NO: 19, SEQ ID NO: 20, SEQ ID NO: 22, SEQ ID NO: 23, and SEQ ID NO: 24. According to some embodiments, the antibody comprises: a variable heavy chain ($V_H$) polypeptide comprising an amino acid sequence having 70% or greater, 75% or greater, 80% or greater, 85% or greater, 90% or greater, or 95% or greater identity to the amino acid sequence set forth in SEQ ID NO: 17; and a variable light chain ($V_L$) polypeptide comprising an amino acid sequence having 70% or greater, 75% or greater, 80% or greater, 85% or greater, 90% or greater, or 95% or greater identity to the amino acid sequence set forth in SEQ ID NO: 21.

In some cases, antibodies comprise the three heavy chain CDRs as set forth in SEQ ID NOs: 18 to 20 and have amino acid substitutions in the sequence of SEQ ID NO: 17 outside the CDRs such that the resulting $V_H$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 17. Similarly, in some cases, antibodies comprise the three heavy chain CDRs as set forth in SEQ ID NOs: 22 to 24 and have amino acid substitutions in the sequence of SEQ ID NO: 21 outside the CDRs such that the resulting $V_L$ polypeptide comprises an amino acid sequence having 70% or greater, 75% or greater, 80% or greater, 85% or greater, 90% or greater, 95% or greater, or 99% or greater sequence identity to the amino acid sequence set forth in SEQ ID NO: 21.

The amino acid sequences of the above-referenced variable heavy chain ($V_H$) polypeptides, variable light chain ($V_L$) polypeptides, and CDRs are provided in Table 1 below.

TABLE 1

| | $V_H$, $V_L$, and CDR Amino Acid Sequences |
|---|---|
| 28H3-28K1 $V_H$ (SEQ ID NO: 1) | METGPRWLLLVAVLKGVQCQSLEESGGDLVKPGASLALTCKASGL DFSRSDHWICWVRQAPGKGLESIGCIYIGSGTFVRSGTTYYASWA KGRFTISKTSSTTVTLQMTSLTGADTATYFCARGFYATDGYGGPSYL NLWGQGTLVTVSSGQPKAPSVFPLAPCCGDTPSSTVTLGCLVKGYL PEPVTVTWNSGTLTNGVRTFPSVRQSSGLYSLSSVVSVTSSSQPVTC NVAHPATNTKVDKTVAPSTCSKPTCPPPELLGGPSVFIFPPKPKDTL MISRTPEVTCVVVDVSQDDPEVQFTWYINNEQVRTARPPLREQQFN STIRVVSTLPITHQDWLRGKEFKCKVHNKALPAPIEKTISKARGQPLE PKVYTMGPPREELSSRSVSLTCMINGFYPSDISVEWEKNGKAEDNY KTTPAVLDSDGSYFLYNKLSVPTSEWQRGDVFTCSVMHEALHNHY TQKSISRSPGK* |
| 28H3-28K1 $V_H$ CDR1 (SEQ ID NO: 2) | RSDHWIC |
| 28H3-28K1 $V_H$ CDR2 (SEQ ID NO: 3) | CIYIGSGTFVRSGTTYYASWAKG |
| 28H3-28K1 $V_H$ CDR3 (SEQ ID NO: 4) | GFYATDGYGGPSYLNL |
| 28H3-28K1 $V_L$ (SEQ ID NO: 5) | MDTRAPTQLLGLLLLWLPGARCADIVMTQTPASVEAAVGGTVTIKC QASESISSYCSWFQQKPGQPPKLLIYRASTLESGVPSRFKGSGSGTQF TLTISDLECADAATYYCQSYAYSSPDSYGSTFGGGTEVVVKGDPVA PTVLIFPPAADQVATGTVTIVCVANKYFPDVTVTWEVDGTTQTTGIE NSKTPQNSADCTYNLSSTLTLTSTQYNSHKEYTCKVTQGTTSVVQSF NRGDC* |
| 28H3-28K1 $V_L$ CDR1 (SEQ ID NO: 6) | QASESISSYCS |
| 28H3-28K1 $V_L$ CDR2 (SEQ ID NO: 7) | RASTLES |
| 28H3-28K1 $V_L$ CDR3 (SEQ ID NO: 8) | QSYAYSSPDSYGST |
| 32H1-32K2 $V_H$ (SEQ ID NO: 9) | METGLRWLLLVAVLKGVQCQSLEESGGDLVKPGASLTLTCTASGLS FSSSDHWICWVRQAPGKGLESVGCIYIGSGTFVSSGTTYFASWAKGR SIISKTSSTTVTLQMTSLTAADTATYFCARGFYYTDGSGGPSYLNLW GQGTLVTVSSGQPKAPSVFPLAPCCGDTPSSTVTLGCLVKGYLPEPV TVTWNSGTLTNGVRTFPSVRQSSGLYSLSSVVSVTSSSQPVTCNVAH PATNTKVDKTVAPSTCSKPTCPPPELLGGPSVFIFPPKPKDTLMISRTP EVTCVVVDVSQDDPEVQFTWYINNEQVRTARPPLREQQFNSTIRVV STLPITHQDWLRGKEFKCKVHNKALPAPIEKTISKARGQPLEPKVYT MGPPREELSSRSVSLTCMINGFYPSDISVEWEKNGKAEDNYKTTPAV LDSDGSYFLYNKLSVPTSEWQRGDVFTCSVMHEALHNHYTQKSISR SPGK* |
| 32H1-32K2 $V_H$ CDR1 (SEQ ID NO: 10) | SSDHWIC |
| 32H1-32K2 $V_H$ CDR2 (SEQ ID NO: 11) | CIYIGSGTFVSSGTTYFASWAKG |

TABLE 1-continued

V_H, V_L, and CDR Amino Acid Sequences

| | |
|---|---|
| 32H1-32K2 V_H CDR3 (SEQ ID NO: 12) | GFYYTDGSGGPSYLNL |
| 32H1-32K2 V_L (SEQ ID NO: 13) | MDTRAPTQLLGLLLLWLPGARCADIVMTQTPASVEAAVGGTVTIKC QASQTIYSYLSWFQQKPGQPPKLLIYSASTLASGVSSRFKGSRSGTE STLTISDLECADAATYYCQSYMYSSSSSFGSTFGGGTEVVVKGDPVA PTVLIFPPAADQVATGTVTIVCVANKYFPDVTVTWEVDGTTQTTGIE NSKTPQNSADCTYNLSSTLTLTSTQYNSHKEYTCKVTQGTTSVVQSF NRGDC* |
| 32H1-32K2 V_L V_L CDR1 (SEQ ID NO: 14) | QASQTIYSYLS |
| 32H1-32K2 V_L V_L CDR2 (SEQ ID NO: 15) | SASTLAS |
| 32H1-32K2 V_L V_L CDR3 (SEQ ID NO: 16) | QSYMYSSSSSFGST |
| 64H1-64K1 V_H (SEQ ID NO: 17) | METGLRWLLLVAVLKGVQCQSLEESGGRLVTPGTPMTLTCTASGFS LVKYYMTWVRQAPGKGLEYIGVIWSGGMTYYASWAKGRFTISRTS TTVDLKIISPTTEDTATYFCARERDYFDGYIGNDIWGQGTLVTVSSG QPKAPSVFPLAPCCGDTPSSTVTLGCLVKGYLPEPVTVTWNSGTLTN GVRTFPSVRQSSGLYSLSSVVSVTSSSQPVTCNVAHPATNTKVDKTV APSTCSKPTCPPPELLGGPSVFIFPPKPKDTLMISRTPEVTCVVVDVSQ DDPEVQFTWYINNEQVRTARPPLREQQFNSTIRVVSTLPITHQDWLR GKEFKCKVHNKALPAPIEKTISKARGQPLEPKVYTMGPPREELSSRS VSLTCMINGFYPSDISVEWEKNGKAEDNYKTTPAVLDSDGSYFLYN KLSVPTSEWQRGDVFTCSVMHEALHNHYTQKSISRSPGK* |
| 64H1-64K1 V_H CDR1 (SEQ ID NO: 18) | KYYMT |
| 64H1-64K1 V_H CDR2 (SEQ ID NO: 19) | VIWSGGMTYYASWAKG |
| 64H1-64K1 V_H CDR3 (SEQ ID NO: 20) | ERDYFDGYIGNDI |
| 64H1-64K1 V_L (SEQ ID NO: 21) | MDTRAPTQLLGLLLLWLPGATFAQVLTQTPSSVSAAVGGTVTINCQ SSQSVWSRHLSWFQQKPGQPPKLLIYKASTLASGVPSRFSGSGSGTQ FTLTISDVQCDDAATYYCLGGYTCIRDDCRAFGGGTEVVVKGDPVA PTVLIFPPAADQVATGTVTIVCVANKYFPDVTVTWEVDGTTQTTGIE NSKTPQNSADCTYNLSSTLTLTSTQYNSHKEYTCKVTQGTTSVVQSF NRGDC* |
| 64H1-64K1 V_L CDR1 (SEQ ID NO: 22) | QSSQSVWSRHLS |
| 64H1-64K1 V_L CDR2 (SEQ ID NO: 23) | KASTLAS |
| 64H1-64K1 V_L CDR3 (SEQ ID NO: 24) | LGGYTCIRDDCRA |

In certain embodiments, an antibody of the present disclosure further specifically binds to an analog of MTX. Analogs of interest include, but are not limited to, Pralatrexate and Phototrexate. According to some embodiments, an antibody of the present disclosure has reactivity of Pralatrexate of greater than 5%, greater than 10%, greater than 15%, greater than 20%, greater than 25%, greater than 30%, greater than 35%, greater than 40%, greater than 45%, or greater than 50%, of its reactivity for MTX.

Aspects of the present disclosure further include nucleic acids. In certain embodiments, a nucleic acid of the present disclosure encodes a variable heavy chain (V_H) polypeptide, a variable light chain (V_L) polypeptide, or both, of any of the antibodies of the present disclosure, including but not limited to a V_H and/or a V_L that includes the CDRs of any of the antibodies set forth in Table 1. Examples of nucleic acids having nucleotide sequences that encode example antibodies of the present disclosure are provided in Table 2 below.

TABLE 2

| | Nucleotide Sequences |
|---|---|
| 28H3-28K1 V$_H$ (SEQ ID NO: 25) | ATGGAGACCGGCCCCAGGTGGCTGCTGCTGGTGGCCGTGCTGAA<br>GGGCGTGCAGTGCCAGAGCCTGGAGGAGAGCGGCGGCGACCTG<br>GTGAAGCCCGGCGCCAGCCTGGCCCTGACCTGCAAGGCCAGCGG<br>CCTGGACTTCAGCAGGAGCGACCACTGGATCTGCTGGGTGAGGC<br>AGGCCCCCGGCAAGGGCCTGGAGAGCATCGGCTGCATCTACATC<br>GGCAGCGGCACCTTCGTGAGGAGCGGCACCACCTACTACGCCAG<br>CTGGGCCAAGGGCAGGTTCACCATCAGCAAGACCAGCAGCACCA<br>CCGTGACCCTGCAGATGACCAGCCTGACCGGCGCCGACACCGCC<br>ACCTACTTCTGCGCCAGGGGCTTCTACGCCACCGACGGCTACGGC<br>GGCCCCAGCTACCTGAACCTGTGGGGCCAGGGCACCCTGGTGAC<br>CGTGAGCAGCGGCCAGCCCAAGGCCCCCAGCGTGTTCCCCCTGG<br>CCCCCTGCTGCGGCGACACCCCCAGCAGCACCGTGACCCTGGGC<br>TGCCTGGTGAAGGGCTACCTGCCCGAGCCCGTGACCGTGACCTG<br>GAACAGCGGCACCCTGACCAACGGCGTGAGGACCTTCCCCAGCG<br>TGAGGCAGAGCAGCGGCCTGTACAGCCTGAGCAGCGTGGTGAGC<br>GTGACCAGCAGCAGCCAGCCCGTGACCTGCAACGTGGCCCACCC<br>CGCCACCAACACCAAGGTGGACAAGACCGTGGCCCCCAGCACCT<br>GCAGCAAGCCCACCTGCCCCCCCCCGAGCTGCTGGGCGGCCCC<br>AGCGTGTTCATCTTCCCCCCCAAGCCCAAGGACACCCTGATGATC<br>AGCAGGACCCCCGAGGTGACCTGCGTGGTGGTGGACGTGAGCCA<br>GGACGACCCCGAGGTGCAGTTCACCTGGTACATCAACAACGAGC<br>AGGTGAGGACCGCCAGGCCCCCCCTGAGGGAGCAGCAGTTCAAC<br>AGCACCATCAGGGTGGTGAGCACCCTGCCCATCACCCACCAGGA<br>CTGGCTGAGGGGCAAGGAGTTCAAGTGCAAGGTGCACAACAAGG<br>CCCTGCCCGCCCCCATCGAGAAGACCATCAGCAAGGCCAGGGGC<br>CAGCCCCTGGAGCCCAAGGTGTACACCATGGGCCCCCCCAGGGA<br>GGAGCTGAGCAGCAGGAGCGTGAGCCTGACCTGCATGATCAACG<br>GCTTCTACCCCAGCGACATCAGCGTGGAGTGGGAGAAGAACGGC<br>AAGGCCGAGGACAACTACAAGACCACCCCCGCCGTGCTGGACAG<br>CGACGGCAGCTACTTCCTGTACAACAAGCTGAGCGTGCCCACCA<br>GCGAGTGGCAGAGGGGCGACGTGTTCACCTGCAGCGTGATGCAC<br>GAGGCCCTGCACAACCACTACACCCAGAAGAGCATCAGCAGGAG<br>CCCCGGCAAGTGA |
| 28H3-28K1 V$_L$ (SEQ ID NO: 26) | ATGGACACCAGGGCCCCCACCCAGCTGCTGGGCCTGCTGCTGCT<br>GTGGCTGCCCGGCGCCAGGTGCGCCGACATCGTGATGACCCAGA<br>CCCCCGCCAGCGTGGAGGCCGCCGTGGGCGGCACCGTGACCATC<br>AAGTGCCAGGCCAGCGAGAGCATCAGCAGCTACTGCAGCTGGTT<br>CCAGCAGAAGCCCGGCCAGCCCCCCAAGCTGCTGATCTACAGGG<br>CCAGCACCCTGGAGAGCGGCGTGCCCAGCAGGTTCAAGGGCAGC<br>GGCAGCGGCACCCAGTTCACCCTGACCATCAGCGACCTGGAGTG<br>CGCCGACGCCGCCACCTACTACTGCCAGAGCTACGCCTACAGCA<br>GCCCCGACAGCTACGGCAGCACCTTCGGCGGCGGCACCGAGGTG<br>GTGGTGAAGGGCGACCCCGTGGCCCCCACCGTGCTGATCTTCCCC<br>CCCGCCGCCGACCAGGTGGCCACCGGCACCGTGACCATCGTGTG<br>CGTGGCCAACAAGTACTTCCCCGACGTGACCGTGACCTGGGAGG<br>TGGACGGCACCACCCAGACCACCGGCATCGAGAACAGCAAGACC<br>CCCCAGAACAGCGCCGACTGCACCTACAACCTGAGCAGCACCCT<br>GACCCTGACCAGCACCCAGTACAACAGCCACAAGGAGTACACCT<br>GCAAGGTGACCCAGGGCACCACCAGCGTGGTGCAGAGCTTCAAC<br>AGGGGCGACTGC |
| 32H1/32K2 V$_H$ (SEQ ID NO: 27) | ATGGAGACCGGCCTGAGGTGGCTGCTGCTGGTGGCCGTGCTGAA<br>GGGCGTGCAGTGCCAGAGCCTGGAGGAGAGCGGCGGCGACCTG<br>GTGAAGCCCGGCGCCAGCCTGACCCTGACCTGCACCGCCAGCGG<br>CCTGAGCTTCAGCAGCAGCGACCACTGGATCTGCTGGGTGAGGC<br>AGGCCCCCGGCAAGGGCCTGGAGAGCGTGGCTGCATCTACATC<br>GGCAGCGGCACCTTCGTGAGCAGCGGCACCACCTACTTCGCCAG<br>CTGGGCCAAGGGCAGGAGCATCATCAGCAAGACCAGCAGCACCA<br>CCGTGACCCTGCAGATGACCAGCCTGACCGCCGCCGACACCGCC<br>ACCTACTTCTGCGCCAGGGGCTTCTACTACACCGACGGCAGCGGC<br>GGCCCCAGCTACCTGAACCTGTGGGGCCAGGGCACCCTGGTGAC<br>CGTGAGCAGCGGCCAGCCCAAGGCCCCCAGCGTGTTCCCCCTGG<br>CCCCCTGCTGCGGCGACACCCCCAGCAGCACCGTGACCCTGGGC<br>TGCCTGGTGAAGGGCTACCTGCCCGAGCCCGTGACCGTGACCTG<br>GAACAGCGGCACCCTGACCAACGGCGTGAGGACCTTCCCCAGCG<br>TGAGGCAGAGCAGCGGCCTGTACAGCCTGAGCAGCGTGGTGAGC<br>GTGACCAGCAGCAGCCAGCCCGTGACCTGCAACGTGGCCCACCC<br>CGCCACCAACACCAAGGTGGACAAGACCGTGGCCCCCAGCACCT<br>GCAGCAAGCCCACCTGCCCCCCCCCGAGCTGCTGGGCGGCCCC<br>AGCGTGTTCATCTTCCCCCCCAAGCCCAAGGACACCCTGATGATC<br>AGCAGGACCCCCGAGGTGACCTGCGTGGTGGTGGACGTGAGCCA<br>GGACGACCCCGAGGTGCAGTTCACCTGGTACATCAACAACGAGC<br>AGGTGAGGACCGCCAGGCCCCCCCTGAGGGAGCAGCAGTTCAAC<br>AGCACCATCAGGGTGGTGAGCACCCTGCCCATCACCCACCAGGA<br>CTGGCTGAGGGGCAAGGAGTTCAAGTGCAAGGTGCACAACAAGG<br>CCCTGCCCGCCCCCATCGAGAAGACCATCAGCAAGGCCAGGGGC<br>CAGCCCCTGGAGCCCAAGGTGTACACCATGGGCCCCCCCAGGGA |

TABLE 2-continued

Nucleotide Sequences

| | |
|---|---|
| | GGAGCTGAGCAGCAGGAGCGTGAGCCTGACCTGCATGATCAACG<br>GCTTCTACCCCAGCGACATCAGCGTGGAGTGGGAGAAGAACGGC<br>AAGGCCGAGGACAACTACAAGACCACCCCCGCCGTGCTGGACAG<br>CGACGGCAGCTACTTCCTGTACAACAAGCTGAGCGTGCCCACCA<br>GCGAGTGGCAGAGGGGCGACGTGTTCACCTGCAGCGTGATGCAC<br>GAGGCCCTGCACAACCACTACACCCAGAAGAGCATCAGCAGGAG<br>CCCCGGCAAGTGA |
| 32H1-32K2 V<sub>L</sub><br>(SEQ ID NO: 28) | ATGGACACCAGGGCCCCCACCCAGCTGCTGGGCCTGCTGCTGCT<br>GTGGCTGCCCGGCGCCAGGTGCGCCGACATCGTGATGACCCAGA<br>CCCCCGCCAGCGTGGAGGCCGCCGTGGGCGGCACCGTGACCATC<br>AAGTGCCAGGCCAGCCAGACCATCTACAGCTACCTGAGCTGGTT<br>CCAGCAGAAGCCCGGCCAGCCCCCCAAGCTGCTGATCTACAGCG<br>CCAGCACCCTGGCCAGCGGCGTGAGCAGCAGGTTCAAGGGCAGC<br>AGGAGCGGCACCGAGAGCACCCTGACCATCAGCGACCTGGAGTG<br>CGCCGACGCCGCCACCTACTACTGCCAGAGCTACATGTACAGCA<br>GCAGCAGCAGCTTCGGCAGCACCTTCGGCGGCGGCACCGAGGTG<br>GTGGTGAAGGGCGACCCCGTGGCCCCCACCGTGCTGATCTTCCCC<br>CCCGCCGCCGACCAGGTGGCCACCGGCACCGTGACCATCGTGTG<br>CGTGGCCAACAAGTACTTCCCCGACGTGACCGTGACCTGGGAGG<br>TGGACGGCACCACCCAGACCACCGGCATCGAGAACAGCAAGACC<br>CCCCAGAACAGCGCCGACTGCACCTACAACCTGAGCAGCACCCT<br>GACCCTGACCAGCACCCAGTACAACAGCCACAAGGAGTACACCT<br>GCAAGGTGACCCAGGGCACCACCAGCGTGGTGCAGAGCTTCAAC<br>AGGGGCGACTGC |
| 64H1-64K1 V<sub>H</sub><br>(SEQ ID NO: 29) | ATGGAGACCGGCCTGAGGTGGCTGCTGCTGGTGGCCGTGCTGAA<br>GGGCGTGCAGTGCCAGAGCCTGGAGGAGAGCGGCGGCAGGCTG<br>GTGACCCCCGGCACCCCCATGACCCTGACCTGCACCGCCAGCGG<br>CTTCAGCCTGGTGAAGTACTACATGACCTGGGTGAGGCAGGCCC<br>CCGGCAAGGGCCTGGAGTACATCGGCGTGATCTGGAGCGGCGGC<br>ATGACCTACTACGCCAGCTGGGCCAAGGGCAGGTTCACCATCAG<br>CAGGACCAGCACCACCGTGGACCTGAAGATCATCAGCCCCCACCA<br>CCGAGGACACCGCCACCTACTTCTGCGCCAGGGAGAGGGACTAC<br>TTCGACGGCTACATCGGCAACGACATCTGGGGCCAGGGCACCCT<br>GGTGACCGTGAGCAGCGGCCAGCCCAAGGCCCCCAGCGTGTTCC<br>CCCTGGCCCCCTGCTGCGGCGACACCCCCAGCAGCACCGTGACC<br>CTGGGCTGCCTGGTGAAGGGCTACCTGCCCGAGCCCGTGACCGT<br>GACCTGGAACAGCGGCACCCTGACCAACGGCGTGAGGACCTTCC<br>CCAGCGTGAGGCAGAGCAGCGGCCTGTACAGCCTGAGCAGCGTG<br>GTGAGCGTGACCAGCAGCAGCCAGCCCGTGACCTGCAACGTGGC<br>CCACCCCGCCACCAACACCAAGGTGGACAAGACCGTGGCCCCCA<br>GCACCTGCAGCAAGCCCACCTGCCCCCCCCCGAGCTGCTGGGC<br>GGCCCCAGCGTGTTCATCTTCCCCCCCAAGCCCAAGGACACCCTG<br>ATGATCAGCAGGACCCCCGAGGTGACCTGCGTGGTGGTGGACGT<br>GAGCCAGGACGACCCCGAGGTGCAGTTCACCTGGTACATCAACA<br>ACGAGCAGGTGAGGACCGCCAGGCCCCCCCTGAGGGAGCAGCA<br>GTTCAACAGCACCATCAGGGTGGTGAGCACCCTGCCCATCGCCC<br>ACCAGGACTGGCTGAGGGGCAAGGAGTTCAAGTGCAAGGTGCAC<br>AACAAGGCCCTGCCCGCCCCCATCGAGAAGACCATCAGCAAGGC<br>CAGGGGGCCAGCCCCTGGAGCCCAAGGTGTACACCATGGGCCCCC<br>CCAGGGAGGAGCTGAGCAGCAGGAGCGTGAGCCTGACCTGCATG<br>ATCAACGGCTTCTACCCCAGCGACATCAGCGTGGAGTGGGAGAA<br>GAACGGCAAGGCCGAGGACAACTACAAGACCACCCCCGCCGTGC<br>TGGACAGCGACGGCAGCTACTTCCTGTACAACAAGCTGAGCGTG<br>CCCACCAGCGAGTGGCAGAGGGGCGACGTGTTCACCTGCAGCGT<br>GATGCACGAGGCCCTGCACAACCACTACACCCAGAAGAGCATCA<br>GCAGGAGCCCCGGCAAGTGA |
| 64H1-64K1 V<sub>L</sub><br>(SEQ ID NO: 30) | ATGGACACCAGGGCCCCCACCCAGCTGCTGGGCCTGCTGCTGCT<br>GTGGCTGCCCGGCGCCACCTTCGCCCAGGTGCTGACCCAGAGCC<br>CAGCAGCGTGAGCGCCGCCGTGGGCGGCACCGTGACCATCAACT<br>GCCAGAGCAGCCAGAGCGTGTGGAGCAGGCACCTGAGCTGGTTC<br>CAGCAGAAGCCCGGCCAGCCCCCCAAGCTGCTGATCTACAAGGC<br>CAGCACCCTGGCCAGCGGCGTGCCCAGCAGGTTCAGCGGCAGCG<br>GCAGCGGCACCCAGTTCACCCTGACCATCAGCGACGTGCAGTGC<br>GACGACGCCGCCACCTACTACTGCCTGGGCGGCTACACCTGCATC<br>AGGGACGACTGCAGGGCCTTCGGCGGCGGCACCGAGGTGGTGGT<br>GAAGGGCGACCCCGTGGCCCCCACCGTGCTGATCTTCCCCCCCGC<br>CGCCGACCAGGTGGCCACCGGCACCGTGACCATCGTGTGCGTGG<br>CCAACAAGTACTTCCCCGACGTGACCGTGACCTGGGAGGTGGAC<br>GGCACCACCCAGACCACCGGCATCGAGAACAGCAAGACCCCCCA<br>GAACAGCGCCGACTGCACCTACAACCTGAGCAGCACCCTGACCC<br>TGACCAGCACCCAGTACAACAGCCACAAGGAGTACACCTGCAAG<br>GTGACCCAGGGCACCACCAGCGTGGTGCAGAGCTTCAACAGGGGG<br>CGACTGC |

Also provided are expression vectors that include any of the nucleic acids of the present disclosure. The expression vectors find use, e.g., for expressing a $V_H$ and/or a $V_L$ of an antibody of the present disclosure in a host cell. The expression of natural or synthetic nucleic acids encoding a $V_H$ and/or a $V_L$ of an antibody of the present disclosure will typically be achieved by operably linking a nucleic acid encoding the $V_H$ and/or $V_L$ to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the $V_H$ and/or $V_L$. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook et al (1989). To obtain high levels of expression of a cloned nucleic acid it is common to construct expression plasmids which typically contain a strong promoter to direct transcription, a ribosome binding site for translational initiation, and a transcription/translation terminator.

Accordingly, aspects of the present disclosure further include cells, e.g., recombinant host cells. In certain embodiments, provided are cells that include any of the nucleic acids and/or expression vectors of the present disclosure. According to some embodiments, provided are cells that include a first nucleic acid encoding a variable heavy chain ($V_H$) polypeptide of an antibody of the present disclosure, and a second nucleic acid encoding a variable light chain ($V_L$) polypeptide of the antibody. In certain embodiments, provided are cells that include a first expression vector comprising the first nucleic acid, and a second expression vector comprising the second nucleic acid. Cells of the present disclosure may be produced by introducing one or more nucleic acids and/or expression vectors of the present disclosure into host cells via methods known in the art, e.g., electroporation, lipofection, microinjection, or the like.

Also provided are methods of making the antibodies of the present disclosure. In certain embodiments, such methods include culturing a cell (e.g., recombinant host cell) of the present disclosure under conditions suitable for the cell to express the antibody, wherein the antibody is produced. The suitable conditions for culturing the cell such that the antibody is expressed may vary. Such conditions may include culturing the cell in a suitable container (e.g., a cell culture plate or well thereof), in suitable medium (e.g., cell culture medium, such as DMEM, RPMI, MEM, IMDM, DMEM/F-12, or the like) at a suitable temperature (e.g., 32° C.-42° C., such as 37° C.) and pH (e.g., pH 7.0-7.7, such as pH 7.4) in an environment having a suitable percentage of $CO_2$, e.g., 3% to 10%, such as 5%).

Also provided are methods of preparing polyclonal antibodies that specifically bind any of the new immunogens derived from Formula 1. Antiserum containing antibodies is obtained by well-established techniques involving immunization of an animal, such as rabbits and sheep, with an appropriate immunogen derived from Formula 1 and obtaining antisera from the blood of the immunized animal after an appropriate waiting period. Reviews are provided by Parker, Radioimmunoassay of Biologically Active Compounds, Prentice-Hall (Englewood Cliffs, N.J., U.S., 1976), Butler, J. Immunol. Meth. 7: 1 24 (1975); Broughton and Strong, Clin. Chem. 22: 726 732 (1976); and Playfair, et al., Br. Med. Bull. 30: 24 31 (1974). The immunization procedures are well established in the art and are set forth in numerous treatises and publications including "The Immunoassay Handbook," 4$^{th}$ Edition, edited by David Wild (Nature Publishing Group, 2013) and the references cited therein. The degree of the antibody purification required depends on the desired application. For many purposes there is no requirement for purification.

Serum harvested may be tested for the presence of antibodies that specifically bind MTX analyte using a MTX protein conjugate or other MTX conjugates in either an ELISA format or homogeneous enzyme immunoassay format. This technique is generally applicable to produce polyclonal antibodies to MTX analyte as described herein and to assess their utility. The specific antibodies prepared are useful as reagents for immunoassays for the detection or determination (optionally including quantification) of MTX.

The following procedure may be employed to prepare monoclonal antibodies, in particular for monoclonal antibodies that specifically bind the immunogens of Formula 1. Monoclonal antibodies may be produced according to the standard techniques of Kohler and Milstein, Nature 265:495 497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3 46 (1981). Samples of an appropriate immunogen preparation are injected into an animal such as a rabbit or mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity. Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody may be harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kohler and Milstein, supra).

The following procedure may be employed to prepare recombinant monoclonal antibodies, in particular monoclonal antibodies that specifically bind the immunogens of Formula 1. Single B-cell screen, cloning and expression was performed. Peripheral blood mononuclear cells (PBMCs) were isolated from whole blood of rabbit and cultured the same day and plating single B-cells onto 40×96 well plates. The 40×96-well plates were incubated at 37° C./5% $CO_2$ for seven days in B cell culturing media and the supernatants were then screened by indirect ELISA against-BSA antigen to determine antigen-positive wells. Antigen-positive wells were preserved in RNA lysis buffer and stored at −80° C. mRNA was isolated from selected B cell well (MTX-SH- BSA antigen-positive wells) by Dynabeads mRNA DIRECT purification kit (Ambion, catalog #61012). cDNA was synthesized and 2 rounds of PCR performed to prepare the antibody variable region cDNA for cloning. Rabbit IgG heavy and kappa light chain variable region cDNAs were cloned into mammalian expression vectors with a rabbit heavy and a light chain constant region, respectively. Expression constructs were co-transfected into HEK 293 cells and cell culture supernatants assayed by indirect ELISA against DAMP-Y-S-BSA antigen. The antibodies were purified according to standard approaches for antibody purification from supernatants. In general, antibodies can be purified by known techniques such as chromatography, e.g., DEAE chromatography, aBx chromatography, and the like, filtration, and so forth. Antibodies may be screened using any of several techniques, for example using a homogeneous enzyme immunoassay format and considering such properties as, conjugate inhibition, curve size and cross-reactivity, and so forth.

DNA sequencing was performed for selected positive rabbit monoclonal antibodies. The rabbit IgG heavy chain sequence is approximately 1200 bp and can be sequenced from the 5' ends to obtain a reliable full-length variable sequence. The rabbit kappa light chain is approximately 700 bp and full-length variable sequence can be reliably obtained from sequencing in the 5' direction. All heavy chain and kappa chain variable region sequences were translated. The resulting amino acid sequences of the $V_H$ and $V_L$ of example antibodies are provided in Table 1 above, while the corresponding nucleotide sequences are in Table 2 above.

Compositions

The present disclosure also provides compositions. According to some embodiments, a composition of the present disclosure includes any of the compounds, antibodies, nucleic acids, expression vectors, and/or cells of the present disclosure.

In certain aspects, a composition of the present disclosure includes any of the compounds, antibodies, nucleic acids, expression vectors, and/or cells of the present disclosure present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, a protease inhibitor, glycerol, a chelating agent, and the like may be present in such compositions.

In certain embodiments, the compositions of the present disclosure find use as reagents in performing any of the immunoassays of the present disclosure, including any of the homogenous enzyme immunoassays described herein. For example, a composition that includes any of the compounds of Formula 1 of the present disclosure, any of the antibodies of the present disclosure, or both, may be employed to perform such immunoassays. According to some embodiments, the reagents are provided in lyophilized form, e.g., to increase stability, convenience, and/or the like. As just one example, a composition that includes any of the compounds of Formula 1 of the present disclosure, any of the antibodies of the present disclosure, or both, may be provided in the form of lyophilized reagent spheres as described in U.S. Pat. No. 5,413,732, the disclosure of which is incorporated herein by reference in its entirety for all purposes. Briefly, such spheres may be made, e.g., by forming a homogeneous solution of a reagent; measuring uniform drops of the solution (e.g., 2 to 50 μL); dispensing the uniform, measured drops into an unagitated cryogenic liquid (e.g., liquid nitrogen), whereby the drops are frozen; collecting the frozen drops from the cryogenic liquid; and lyophilizing the frozen drops, thereby forming a plurality of lyophilized reagent spheres.

Immunoassays

Aspects of the present disclosure further include methods of using any of the compounds of Formula 1 of the present disclosure and/or any of the antibodies of the present disclosure. In certain embodiments, such compounds and/or antibodies may be used for detecting (including determining an amount of) at least one MTX analyte in a medium, e.g., a medium that includes a biological sample of interest. For example, according to some embodiments, provided are methods for determining an amount of at least one MTX analyte in a medium, the methods including combining in a medium a sample suspected of containing at least one MTX analyte, and any of the antibodies of the present disclosure. Such methods further include determining the presence or absence of a complex comprising the MTX analyte and the antibody, wherein the presence of the complex indicates the presence of the MTX analyte in the sample. In certain embodiments, the medium further includes any of the compounds of Formula 1 of the present disclosure. For example, the medium may further include a MTX conjugate that has a MTX moiety and a detectable label (e.g., enzyme, such as G6PDH).

The sample suspected of containing at least one MTX analyte may be any sample of interest. In certain embodiments, the sample is whole blood, blood serum, blood plasma, urine, sputum, semen, saliva, ocular lens fluid, cerebral fluid, spinal fluid, amniotic fluid, tissue culture media, or the like, and including dilutions thereof.

The present disclosure provides immunoassay methods for assessing the presence or absence of a MTX analyte in a sample suspected of containing the analyte. Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competitive assays. The immunoassays may embody other types of assays that are neither sandwich nor competitive assays, as in certain assays involving immunoprecipitation. In certain embodiments, the immunoassay is a homogeneous immunoassay, where the assay reagents and sample are mixed together to form a homogeneous assay mixture.

In certain embodiments, the immunoassay is a homogeneous enzyme immunoassay system used for the analysis of a MTX analyte in a biological fluid sample. In some instances, the immunoassay is based on competition between the MTX analyte in the sample and labeled MTX and/or MTX for antibody binding sites. In some embodiments, the label is a protein, such as an enzyme. For example, the label may be an enzyme the activity of which may be measured spectrophotometrically. In one non-limiting example, an assay of the present disclosure employs MTX and/or acylated or alkylated DAMP labeled with the enzyme glucose-6-phosphate dehydrogenase (G6PDH) for antibody binding sites. In certain embodiments, enzyme activity decreases upon binding to the antibody, such that the concentration of the MTX analyte in the sample can be measured in terms of enzyme activity. In some cases, active enzyme converts nicotinamide adenine dinucleotide (NAD$^+$) to NADH, resulting in an absorbance change that is measured spectrophotometrically. In certain instances, endogenous serum G6PDH does not interfere with the immunoassay because the coenzyme NAD$^+$ functions only with the bacterial (*Leuconostoc mesenteroides*) enzyme employed in the assay.

In general, the immunoassays of the present disclosure for detecting the presence (or absence) of a MTX analyte in a sample can be conducted by adding, to a reaction mixture, (i) a sample suspected of containing a MTX analyte and (ii) an antibody that specifically binds to a MTX analyte to form a complex between the antibody and MTX analyte that may be present in the sample. The method also includes detecting the presence or absence of the complex. The presence (or absence) of the complex may be indicative of the presence (or absence) of MTX analyte in the sample. Moreover, the amount of complex formed can be assessed to determine the concentration of MTX analyte present in the sample (e.g., to provide an assessment of serum or tissue concentration of MTX analyte in a subject from whom the sample was obtained). The presence and/or amount of complex can be assessed directly (e.g., by detecting bound antibody in the complex) or indirectly (e.g., by assessing activity of an enzyme in a MTX enzyme conjugate, where when the MTX enzyme conjugate is not bound to antibody, a detectable signal is generated, indicating that the MTX analyte antibody in the reaction mixture has been bound by MTX analyte from the sample) (see, e.g., FIG. 14).

In general, the immunoassays of the present disclosure entail combining in a medium (e.g., assay medium or assay reaction mixture), the sample with a MTX analyte antibody under conditions that permit the formation of a stable complex between the analyte in the sample and the antibody.

Assays may be performed in solution or may use a solid (insoluble) support (e.g., polystyrene, nitrocellulose, particles or beads), using any standard methods (e.g., as described in Current Protocols in Immunology, Coligan et al., ed.; John Wiley & Sons, New York, 1992). Such methods include ELISAs (enzyme-linked immunosorbent assays), IRMAs (immunoradiometric assays), and RIAs (radioimmunoassays). In certain embodiments, the assay is performed in solution, e.g., the assay is performed without the assay reagents attached to or associated with a solid support.

Where the assay is performed in solution, the test sample (and, optionally a control sample) may be incubated with an anti-MTX analyte antibody for a time period sufficient to allow formation of analyte and affinity reagent complexes. As previously noted, the MTX analyte antibody may include a detectable label, e.g., radionuclide, fluorescer, or enzyme. The sample may then be treated to separate the MTX analyte antibody complexes from excess, unreacted MTX analyte antibody (e.g., by addition of a secondary antibody (e.g., anti-immunoglobulin antiserum)) followed by centrifugation to precipitate the secondary complexes, or by binding to an affinity surface such as a second, unlabeled antibody fixed to a solid substrate such as Sepharose® or a plastic well). Detection of MTX analyte antibody bound to a MTX analyte may be achieved in a variety of ways. If necessary, a substrate for the detectable label may be added to the sample.

Where the assay uses a solid support, the support can have a MTX analyte antibody (or conjugate) bound to a support surface. Binding of the assay reagent may facilitate the stable, wash-resistant binding of MTX analyte which may be present in the sample (or antibody that is not bound to MTX analyte from the sample, and is present in the reaction mixture, as in a competitive binding assay) to the solid support via specific binding to the antibody. The insoluble support may be any composition to which antibodies or suitable MTX conjugates can be bound, which can be separated from soluble material, and which is otherwise compatible with the overall method of detection of MTX analyte in a sample.

The surface of such supports may be solid or porous and of any convenient shape. Examples of suitable insoluble supports to which the MTX analyte antibody or conjugate is bound include beads, e.g., magnetic beads, fluorescent particles, membranes and microtiter plates. These can be composed of glass, plastic (e.g., polystyrene), polysaccharides, nylon or nitrocellulose.

Assay reagents can include the MTX analyte antibody as disclosed herein, as well as secondary antibodies, which may be optionally detectably labeled. After binding of an assay reagent to the support, the support may be treated with a blocking agent, which binds to the support in areas not occupied by the assay reagent. Suitable blocking agents include non-interfering proteins such as bovine serum albumin, casein, gelatin, and the like. Alternatively, detergents at non-interfering concentrations, such as Tween, NP40, TX100, and the like may be used. Such blocking treatment may reduce nonspecific binding.

Assays of the present disclosure include both qualitative and quantitative assays. Typical quantitative methods involve mixing an analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte can be used to establish the assay result. Unless otherwise stated, the act of "measuring" or "determining" in this disclosure encompasses both qualitative and quantitative determination.

Immunoassay reagents that find use alone or in combination in the assays described herein include, but are not limited to, a MTX analyte antibody, a MTX conjugate, and a MTX analyte (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives can be introduced to maintain hydrophobic or low-solubility compounds in solution, and stabilize components in the solution. Examples include bulking agents such as β-lactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

The MTX analog DAMP conjugates and/or the MTX analog analyte antibodies to be used as reagents in an assay can be insolubilized by attachment to a solid support. This can be, for example, a wall of a vessel containing the reagent, to a particulate, or to a large molecular weight carrier that can be kept in suspension but removable by physicochemical means, such as centrifugation or microfiltration. In some cases, the attachment is through one or more covalent bonds. The attachment need not be covalent, but is at least of sufficient strength and/or permanence to withstand a separation technique (including a wash) that may be part of the assay procedure. In some cases, the solid support may be functionalized to include a reactive group to facilitate attachment of the MTX conjugate and/or the MTX analyte antibody to the solid support. Nonlimiting examples of reactive groups that may be used include —COOH, —NH$_2$, —C(O)H, —SH, and the like. In some embodiments, the MTX analog conjugate and/or the MTX analog analyte antibody can be conjugated to a protein carrier and the protein carrier can be conjugated to the solid support, thus indirectly attaching the MTX conjugate and/or the MTX analyte antibody to the solid support. Certain particulate materials include, but are not limited to, agarose, polystyrene, cellulose, polyacrylamide, latex particles, magnetic particles, and fixed red cells. Examples of commercially available matrices include, but are not limited to, Sepharose* (Pharmacia), Poros® resins (Roche Molecular Biochemicals), Actigel Superflow™ resins (Sterogene Bioseparations Inc.), and Dynabeads™ (Dynal Inc.). In certain embodiments, the choice of the solid support may depend on one or more of stability, capacity, accessibility of the coupled antibody, flow rate (or the ability to disperse the resin in the reaction mixture), and ease of separation.

As noted above, immunoassays for detection of a MTX analyte can be of a variety of formats. In general, the immunoassays involve combining one or more immunoassay reagents (e.g., at least an anti-MTX analyte antibody) with a test sample (i.e., a sample suspected of containing a MTX analyte) in a medium (e.g., a reaction mixture or an assay mixture). "Reaction mixture" or "assay mixture" generally refers to the combination of a sample suspected of containing a MTX analyte and one or more immunoassay reagents as exemplified in the present disclosure to facilitate detection of the presence or absence of a MTX analyte in the sample, where the detection may be qualitative or quantitative. The reaction mixture is usually an aqueous solution, although the immunoassay reagent(s) may be in solution or immobilized on a support (e.g., a substrate, such as a bead). The reaction mixture can include other components compatible with the immunoassay, e.g., buffers, reagents, and the like.

Immunoassays usually are classified in one of several ways. For example, immunoassays can be classified according to the mode of detection used, i.e., enzyme immunoassays, radio immunoassays, fluorescence polarization immunoassays, chemiluminescence immunoassays, turbidimetric assays, etc. Another grouping method is according to the assay procedure used, i.e., competitive assay formats, sandwich-type assay formats as well as assays based on precipitation or agglutination principles. In certain instances, a further distinction is made depending on whether washing steps are included in the procedure (so-called heterogeneous assays) or whether reaction and detection are performed without a washing step (so-called homogeneous assays). Certain assays are described in more detail below.

Immunoassays may be described as heterogeneous or homogeneous. "Homogeneous immunoassay," as used herein, refers to an assay method where the complex is not separated from unreacted reaction components, but instead the presence of the complex is detected by a property which at least one of the reactants acquires or loses as a result of being incorporated into the complex. Homogeneous assays include systems involving fluorochrome and fluorochrome quenching pairs on different reagents; enzyme and enzyme inhibitor pairs on different reagents; chromophore and chromophore modifier pairs on different reagents; and latex agglutination assays.

A certain homogeneous assay is the quantitative homogeneous enzyme immunoassay in which a symmetric methylarginine is conjugated to an active enzyme. In some embodiments, the conjugation is arranged so that the binding of a MTX analyte antibody to the symmetric methylarginine conjugate affects enzymatic activity of the conjugate in a qualitative or quantitative fashion. If a sample containing MTX analyte is premixed with the antibody, the antibody may complex with the MTX analyte and thus be prevented from binding to the enzyme conjugate. In this way, the activity of the enzyme in the conjugate can be correlated with the amount of MTX analyte present in the sample.

G6PDH is a certain enzyme useful in such assays. In some embodiments, the G6PDH is a variant of a naturally occurring G6PDH in which one or more lysine residues are deleted or substituted, or one or more cysteine residues are introduced. For example, *Leuconostoc mesenteroides* G6PDH are dimeric enzymes that have the ability to catalyze the oxidation of D-glucose-6-phosphate to D-gluconic-delta-lactone-6-phosphate by utilizing either NAD$^+$ or NADP$^+$. This property of using NAD$^+$ differentiates these enzymes from human G6PDH, which utilizes only NADP$^+$ effectively, and allows *L. mesenteroides*-specific G6PDH activity to be measured in the presence of human G6PDH, as for example in human-derived samples. Two certain genera of bacteria from which to select G6PDH are *Leuconostoc* and *Zymomonas*. Within these genera *L. mesenteroides, L. citreum, L. lactis, L. dextranicum*, and *Z. mobilis* are of interest, where *L. mesenteroides, L. citreum*, and *L. lactis* are specific examples. Another example of a homogeneous assay system is the cloned enzyme donor immunoassay.

MTX derivatives DAMP-Y with thiol reactive groups can be prepared as described above, and may be allowed to react with a glucose-6-phosphate dehydrogenase (G6PDH) mutant enzyme to form the respective enzyme conjugates (see, e.g., FIG. 10). The mutant enzyme may be obtained by the procedure described in U.S. Pat. Nos. 6,090,567 and 6,033,890, the disclosures of which are incorporated herein by reference.

In some embodiments, the immunoassay further includes adding a DAMP-Y MTX analog conjugate that has a MTX moiety and a detectable label to the sample. The presence or absence of MTX analyte in the sample can be detected by detecting the detectable label. The detectable label may include an enzyme and the detecting may be performed by assaying activity of the enzyme. In certain embodiments, the enzyme is a dehydrogenase, such as G6PDH.

Luminescence oxygen channeling assay (LOCI) is a chemiluminescence homogeneous immunoassay whereby a biotinylated analyte competes with the analyte for antibody binding on the acceptor particles. The biotinylated analyte is bound to the donor particles through streptavidin present on the donor particles. In the presence of the analyte, the two particles come into close proximity through the biotin-analyte binding interactions. The excitation of the donor beads at 680 nm generates singlet oxygen molecules that trigger a series of chemical reactions in the LOCI acceptor beads resulting in a detectable peak of light emission at 615 nm (Ullman, E. F. et al. (1996) *Clin. Chem.* 42, 1518-1526). In the presence of the analyte the relative light units (RLUS) emitted is inversely proportional to the concentration of the analyte.

In a separation-based or "heterogeneous" assay, the detecting of a complex of a MTX analyte antibody and an analyte involves a process where the complex formed is physically separated from either unreacted analyte, unreacted antibody, or both.

In a heterogeneous immunoassay, a complex of an antibody and a MTX analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or labeled antibody to facilitate detection or quantitation of the complex. Suitable labels include radioisotopes such as $^{125}$I, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

Assays of the present disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with a derivative of the analyte for binding to another reagent, such as an antibody. An example of a competition assay using EMIT® is described in U.S. Pat. No. 3,817,837.

The compounds and methods of the presently disclosed embodiments also encompass the use of these materials in lateral flow chromatography technologies. Lateral flow chromatography involves a membrane strip which includes a detection device, such as a non-isotopic signal generating moiety, for MTX analyte. A sample from a patient may then be applied to the membrane strip. The sample may interact with the detection device, producing a result. The results can signify several things, including the absence of the MTX analyte in the sample, the presence of the MTX analyte in the sample, and/or the concentration of the MTX analyte in the sample.

Certain embodiments provide a method of qualitatively determining the presence or absence of a MTX analyte in a sample, through the use of lateral flow chromatography. In certain embodiments, the basic design of the qualitative lateral flow device is as follows: 1) The sample pad is where the sample is applied. The sample pad is treated with chemicals such as buffers or salts, which, when re-dissolved, optimize the chemistry of the sample for reaction with the conjugate, test, and control reagents; 2) Conjugate release pad is typically a polyester or glass fiber material that is treated with a conjugate reagent such as an antibody colloidal gold conjugate. A typical process for treating a conjugate pad is to use impregnation followed by drying. In use, the liquid sample added to the test will re-dissolve the conjugate so that it will flow into the membrane; 3) The membrane substrate is usually made of nitrocellulose or a similar material whereby antibody capture components are immobilized; 4) A wicking pad is used in tests where blood plasma must be separated from whole blood. An impregnation process is usually used to treat this pad with reagents intended to condition the sample and promote cell separation; 5) The absorbent pad acts as a reservoir for collecting fluids that have flowed through the device; and 6) The above layers and membrane system are laminated onto a plastic backing with adhesive material which serves as a structural member.

Certain embodiments provide a method of qualitatively determining the presence of a MTX analyte in a sample, through the use of lateral flow chromatography. In these embodiments, the membrane strip includes a sample pad, which is a conjugate release pad that has an antibody that is specific for the MTX analyte. This antibody may be conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. In some instances, the membrane strip further includes a capture line, in which the MTX analyte antigen or analyte conjugate is immobilized on the strip. In some embodiments, this immobilization is through covalent attachment to the membrane strip, optionally through a linking group. In other embodiments, the immobilization is through non-covalent attachment to the membrane strip. In still other embodiments, the immobile MTX analyte in the capture line is attached to a reactive partner, such as an immunogenic carrier like BSA.

Sample from a patient may be applied to the sample pad, where it can combine with the antibody in the conjugate release pad, thus forming a solution. This solution may then migrate chromatographically by capillary action across the membrane. When MTX analyte is present in the sample, a MTX analyte antibody complex may be formed, which migrates across the membrane by capillary action. When the solution reaches the capture line, the MTX analyte antibody complex may compete with the immobile MTX analyte for the limited binding sites of the antibody. When a sufficient concentration of MTX analyte is present in the sample, it may fill the limited antibody binding sites. In certain instances, this will prevent the formation of a colored antibody-immobile MTX analyte complex in the capture line. Therefore, absence of color in the capture line indicates the presence of MTX analyte in the sample.

In the absence of MTX analyte in the sample, a colored antibody-immobile MTX analyte complex may form once the solution reaches the capture line of the membrane strip. In some instances, the formation of this complex in the capture line is evidence of the absence of MTX analyte in the sample.

Certain embodiments provide a method of quantitatively determining the amount of a MTX analyte in a sample, through the use of lateral flow chromatography. This technology is further described in U.S. Pat. Nos. 4,391,904; 4,435,504; 4,959,324; 5,264,180; 5,340,539; and 5,416,000, the disclosures of which are incorporated herein by reference. In some embodiments, the antibody may be immobilized along the entire length of the membrane strip. In general, if the membrane strip is made from paper, the antibody may be covalently bound to the membrane strip. If the membrane strip is made from nitrocellulose, then the antibody can be non-covalently attached to the membrane strip through, for example, hydrophobic and electrostatic interactions. The membrane strip may include a conjugate release pad that includes the MTX analyte attached to a detector moiety. In certain embodiments, the detector moiety is an enzyme, such as horseradish peroxidase (HRP).

In certain embodiments, sample from a patient is applied to the membrane strip, where it can combine with the MTX analyte/detector molecule in the conjugate release pad, thus forming a solution. This solution may then be allowed to migrate chromatographically by capillary action across the membrane. When MTX analyte is present in the sample, both the sample MTX analyte and the MTX analyte/detector molecule compete for the limited number of binding sites of the antibody. When a sufficient concentration of MTX analyte is present in the sample, it may fill the limited antibody binding sites. In some instances, this forces the MTX analyte/detector molecule to continue to migrate in the membrane strip. The shorter the distance of migration of the MTX analyte/detector molecule in the membrane strip, the lower the concentration of MTX analyte in the sample, and vice versa. When the MTX analyte/detector molecule includes an enzyme, the length of migration of the MTX analyte/detector molecule can be detected by applying an enzyme substrate to the membrane strip. Detection of the product of the enzyme reaction may then be utilized to determine the concentration of the MTX analyte in the sample. In certain embodiments, the enzyme's color producing substrate such as a modified N,N-dimethylaniline is immobilized to the membrane strip and 3-methyl-2-benzothiazolinone hydrazone is passively applied to the membrane, thus alleviating the need for a separate reagent to visualize the color producing reaction.

Fluorescence polarization immunoassay (FPIA) technology is based upon competitive binding. FPIA technology is described in, for example, U.S. Pat. Nos. 4,593,089, 4,492,762, 4,668,640, and 4,751,190, the disclosures of which are incorporated herein by reference.

The FPIA technology can be used to identify the presence of MTX analyte and can be used in assays that quantify the amount of MTX analyte in a sample. In part, the rotational properties of molecules in solution allow for the degree of polarization to be directly proportional to the size of the molecule. Accordingly, polarization may increase as molecular size increases. That is, when linearly polarized light is used to excite a fluorescent-labeled or other luminescent-labeled MTX analyte thereof, which is small and rotates rapidly in solution, the emitted light may be significantly depolarized. When the fluorescent-labeled MTX analyte interacts with or is bound to an antibody, the rotation may be slowed and the emitted light may be highly polarized. In some cases, this is because the antibody significantly and measurably increases the size of the complex. Also, increasing the amount of unlabeled MTX analyte in the sample can result in decreased binding of the fluorescent-labeled MTX analyte by the MTX analyte antibody, and thereby decrease the polarization of light emitted from sample. The quantitative relationship between polarization and concentration of the unlabeled MTX analyte in the sample can be established by measuring the polarization values of calibrations with known concentrations of MTX analyte. Thus, FPIA can be used to identify the presence and concentration of MTX analyte in a sample. WO95/16026 provides a method for detecting MTX using FPIA and murine IgG.

Homogeneous microparticles immunoassay technology, which can be referred to as immunoturbidimetric assays, is based on the agglutination of particles and compounds in solution. When particles and/or chemical compounds agglutinate, particle sizes can increase and increase the turbidity of a solution. Accordingly, MTX analyte antibodies can be used with microparticles in order to assess the presence, and optionally the amount, of MTX analyte in a sample. Homogeneous microparticles immunoassay may be useful because the immunoassays can be performed on blood, blood hemolysate, serum, plasma, tissue, and/or other samples. Homogeneous microparticles immunoassay assays can be configured to be performed with MTX analyte and loaded onto a microparticle, or with a MTX analyte antibody loaded onto a microparticle. Homogeneous microparticles immunoassay or immunoturbidimetric assays find use for measuring agglutination of substances in a sample. Immunoturbidimetric assay technologies are described in, e.g., U.S. Pat. Nos. 5,571,728, 4,847,209, 6,514,770, and 6,248,597, the disclosures of which are incorporated herein by reference. Such assays involve light attenuation, nephelometric, or turbidimetric methods.

Cloned Enzyme Donor Immunoassays ("CEDIA®", ThermoFisher), as are based upon the competition of MTX analyte in the biological sample with a MTX conjugate containing an inactive genetically engineered enzyme-donor ("ED") fragment such as from β-D-galactoside galactohydrolase or β-galactosidase ("β-gal") from $E.\ coli$, for binding to an antibody capable of binding MTX analyte. Thiol containing ED can be conjugated to the bromoacetamides of the current invention to yield ED conjugates. If MTX analyte is present in the sample it may bind to the antibody, leaving the ED portion of the ED-derivative conjugate free to restore enzyme activity of β-D-galactoside galactohydrolase or b-gal in the reaction mixture so as to be capable of association with enzyme acceptor ("EA") fragments. The active enzyme, which includes the ED and EA, may then be capable of producing a quantifiable reaction product when exposed to an appropriate substrate. An example of a substrate is chlorophenol red-β-D-galactopyranoside ("CPRG"), which can be cleaved by the active enzyme into galactose and CPR, where CPR is measured by absorbency at about wavelength 570 nm. If MTX analyte is not present in the sample, the antibody may bind to the ED-derivative conjugate, thereby inhibiting association of the ED fragments with the EA fragments and inhibiting restoration of enzyme activity. The amount of reaction product and resultant absorbance change are proportional to the amount of MTX analyte in the sample. Alternatively a fluorescent substrate such as umbelliferrone galactoside can be used to give a fluorescent signal. Alternatively a chemiluminescent substrate such as dioxetane galactosides or luciferin galactoside substrates could be used for a luminescent signal.

A competitive assay using chemiluminescent microparticle immunoassay ("CMIA") technology can also be used to assess whether or not MTX analyte is present in a sample (Regis Bouquie et al., Am J. Clin Path 2016). Various types of CMIA technologies may be used for determining the presence and/or amount of an analyte in a sample. CMIA assays can include the use of MTX analyte antibodies, which are capable of binding to MTX analyte, which are coupled to particles, such as magnetic particles or particles suitable for separation by filtration, sedimentation, and/or other means. Additionally, a tracer, which can include a MTX or derivative linked to a suitable chemiluminescent moiety, can be used to compete with free MTX analyte in the patient's sample for the limited amount of MTX analyte antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RLUs). The amount of chemiluminescence is inversely related to the amount of free analyte in the patient's sample and concentration is determined by constructing a standard curve using known values of the analyte.

According to some embodiments, provided is a homogenous enzyme immunoassay for the analysis of MTX in biological fluids (e.g., whole blood, blood serum, blood plasma, urine, sputum, semen, saliva, ocular lens fluid, cerebral fluid, spinal fluid, amniotic fluid, tissue culture media, or the like, and including dilutions thereof). The assay is based on competition between MTX present in the biological fluid and a MTX analog DAMP labeled with an enzyme (e.g., glucose-6-phosphate dehydrogenase (G6PDH)) for antibody binding sites. Enzyme activity decreases upon binding to the antibody, so the MTX concentration in the biological fluid can be measured in terms of enzyme activity. For example, active G6PDH converts nicotinamide adenine dinucleotide (NAD$^+$) to NADH, resulting in an absorbance change that may be measured spectrophotometrically. A bacterial (*Leuconostoc mesenteroides*) enzyme may be employed in the assay so that endogenous serum G6PDH does not interfere because the coenzyme NAD$^+$ functions only with the bacterial enzyme.

In certain embodiments, in an immunoassay of the present disclosure, including in any of the homogenous enzyme immunoassays described herein, one or more reagents are provided in lyophilized form. As just one example, a composition that includes any of the compounds of Formula 1 of the present disclosure, any of the antibodies of the present disclosure, or both, may be provided in the form of lyophilized reagent spheres (or "beads") as described in U.S. Pat. No. 5,413,732, the disclosure of which is incorporated herein by reference in its entirety for all purposes. Briefly, such spheres may be made, e.g., by forming a homogeneous solution of a reagent; measuring uniform drops of the solution (e.g., 2 to 50 µL); dispensing the uniform, measured drops into an unagitated cryogenic liquid (e.g., liquid nitrogen), whereby the drops are frozen; collecting the frozen drops from the cryogenic liquid; and lyophilizing the frozen drops, thereby forming a plurality of lyophilized reagent spheres.

According to some embodiments, e.g., including embodiments in which one or more reagents are provided in lyophilized form, a centrifugal analyzer that includes a microfluidic rotor (or "disc") is employed in an immunoassay of the present disclosure. For example, an immunoassay of the present disclosure may employ an analyzer that includes a centrifugal rotor for separating plasma from whole blood that includes a plurality of internal chambers and passages for combining blood plasma or serum with one or more reagents (e.g., lyophilized spheres as described above) and distributing the plasma or serum to a plurality of individual test wells. The chambers and passages necessary for separating the whole blood into plasma are located radially outward from metering chambers that deliver precisely measured volumes of blood and/or diluent to a separation chamber. The separation chamber includes a radially-outward cell trap. Spinning of the rotor causes the cellular components of the whole blood to be sequestered in the cell trap. The separated plasma is then delivered to a plurality of test wells or cuvettes. The above separation and aliquoting steps typically occur as a result of centrifugal force generated by the spinning rotor. The lyophilized reagent spheres described above in combination with the rotors described above are particularly suitable for analyzing blood plasma or diluted blood plasma. They are also useful with a wide variety of other biological fluids, such as urine, sputum, semen, saliva, ocular lens fluid, cerebral fluid, spinal fluid, amniotic fluid, and tissue culture media, as well as food and industrial chemicals, and the like. Details regarding such centrifugal analyzers that include a microfluidic rotor may be found, e.g., in U.S. Pat. Nos. 5,061,381, 5,173,193; 5,122,284 and 5,186,844, the disclosures of which are incorporated herein in their entireties for all purposes.

In some embodiments, the immunoassay employs a centrifugal analyzer that includes a microfluidic rotor comprising siphons for delivering a premeasured volume of liquid (e.g., a biological sample such as whole blood, blood serum, or blood plasma) between a first and a second chamber in the rotor. The siphons may include an elbow that is radially inward of the radially most inward point of the fluid in the first chamber. As the rotor is spinning, the fluid does not flow past the elbow. Once the rotor stops, capillary forces "prime" the siphon by pulling fluid just around the elbow. When the rotor is restarted, centrifugal force draws the remaining fluid out of the metering chamber into the receiving chamber until the level of the fluid in the metering chamber is at the same radial distance as the outlet of the siphon. The siphons may be designed such that the inlet of the siphon on the first chamber is radially outward of the siphon outlet on the second chamber. The positioning of the inlets and outlets of the siphons provides certain advantages. For example, the inlet of the siphon may always be positioned radially outward of the final position of the meniscus of the fluid in the first chamber, after fluid has been transferred to the second chamber. Thus, inaccuracy in measurement associated with different shaped menisci in different fluids is minimized since the meniscus is minimized. In addition, as will be appreciated by one of skill in the art, all siphons are semi-stable because the train of fluid in a siphon is stable but easily broken if the rotor is perturbed. When the train of fluid is broken, under centrifugal force, the fluid contained in the siphon will flow to the radially most outward point. In previous siphons, this point is the siphon outlet. Thus, the potential exists for the delivery of unmetered volumes of fluid to the receiving chamber. In the siphons described herein, the radially most outward point in the siphon is the siphon inlet. In this design, the problem of delivering unmetered volumes of fluid is avoided because the fluid flows back into the first chamber when the train of fluid is broken. Further details regarding analyzers that include a centrifugal rotor comprising siphons for delivering premeasured volumes of liquid, which may be employed in any of the methods/immunoassays of the present disclosure, may be found in U.S. Pat. No. 7,998,411, the disclosure of which is incorporated herein by reference in its entirety for all purposes.

The MTX derivatives, conjugates, antibodies, immunogens, and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the MTX derivatives, conjugates, antibodies, and immunogens, such assays can also be modified. As such, various modifications of steps or acts for performing such immunoassays can be made within the scope of the embodiments described herein. Additional information related to assay format are described, among other places, in David Wild (The Immunoassay Handbook, 4th Edition Published Date: 31st January 2013, Elsevier Science).

Kits

Aspects of the present disclosure further include kits. In some embodiments, the kits find use in determining an amount of at least one MTX analyte in a sample. Such kits may include any of the compounds of Formula 1 of the present disclosure, any of the antibodies of the present disclosure, or both.

In certain embodiments, provided are kits for determining an amount of MTX analyte in a sample, such kits including any of the antibodies of the present disclosure, and instructions for using the antibody to determine an amount of at least one MTX analyte in a sample. According to some embodiments, the antibody specifically binds to MTX with less than 0.1% cross reactivity to 7-OH MTX. In certain embodiments, the kits that include an antibody of the present disclosure further include any of the compounds of Formula 1 of the present disclosure. In some embodiments, the compound is one where Z is a label, such as an enzyme, e.g., glucose-6-phosphate dehydrogenase (G6PDH).

Also provided are kits for determining an amount of at least one MTX analyte in a sample, the kits including any of the compounds of Formula 1 of the present disclosure, and instructions for using the compound to determine an amount of at least one MTX analyte in a sample. In certain aspects, the compound is one where Z is a label, such as an enzyme, e.g., glucose-6-phosphate dehydrogenase (G6PDH). Such kits may further include any of the antibodies of the present disclosure. According to some embodiments, the antibody specifically binds to MTX but with less than 0.1% cross reactivity to MTX metabolite 7-OH MTX and the kit may further include instructions for determining the amount of MTX in the biological sample.

According to some embodiments, the kits of the present disclosure are useful for conveniently performing an assay for the determination of a MTX analyte in a sample. The kit may include: (a) an antibody raised that specifically binds to MTX and a compound of Formula 1 described herein (e.g., a DAMP conjugate); and (b) instructions for determining the amount of the MTX analyte in the sample. In some embodiments, the kit also includes a conjugate of a compound of Formula 1, where the conjugate includes a label (e.g., a detectable label, such as G6PDH). In certain instances, the kit also includes ancillary reagents for determining the analyte. The antibody of the kit may be an antibody raised against a compound of Formula 1 described herein.

To enhance the versatility of the immunoassay, the kit reagents can be provided in packaged combination, in the same or separate containers, in liquid or lyophilized form so that the ratio of the reagents provides for substantial optimization of the method and assay. In certain embodiments, the kits include an antibody of the present disclosure, a compound of the present disclosure, or both, provided as lyophilized reagent spheres as described in U.S. Pat. No. 5,413,732, the disclosure of which is incorporated herein by reference in its entirety for all purposes. The reagents provided in the kits may each be in separate containers or various reagents can be combined in one or more containers, e.g., depending on the cross-reactivity and stability of the reagents. In some embodiments, the compound of Formula 1 described herein (e.g., a MTX conjugate) is present in lyophilized form. In some embodiments, the antibody is present in lyophilized form. For example, the compound of Formula 1 can be present in a first lyophilized composition (which may further include one or more excipients, buffers, stabilizers, etc.), and the antibody can be present in a second lyophilized composition (which may further include an enzyme substrate and one or more excipients, buffers, stabilizers, etc.). The first lyophilized composition and the second lyophilized composition may be provided in a single kit, such as for example in a packaging or container for single use.

The kit can further include other separately packaged reagents for conducting an assay such as ancillary reagents such as an ancillary enzyme substrate, and so forth. The relative amounts of the various reagents in the kits can be varied widely to provide for concentrations of the reagents that substantially optimize the reactions that need to occur when performing a method/immunoassay (e.g., homogenous enzyme immunoassay) and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The description of certain exemplary embodiments of kits uses the language "and/or," which means that the kit may or may not contain each item mentioned. This language is used for the sake of brevity. In general, an immunoassay kit will include at least one antibody for an immunogen of an analyte, e.g., MTX, and at least one enzyme conjugate (e.g., label conjugate) that corresponds to that analyte, e.g., an enzyme conjugate of a derivative of MTX.

In certain embodiments, a kit is provided for an assay for the analyte MTX and/or metabolites of MTX. The kit may include, in packaged combination: (i) an antibody raised against a compound of Formula 1; and (ii) a conjugate of a derivative of the analyte. Another embodiment of the presently disclosure is a kit for an assay for the analyte MTX and/or metabolites of MTX that includes, in packaged combination: (i) an antibody raised against a derivative of the analyte; and (ii) a conjugate of a hapten of the analyte, where the hapten is a compound of Formula 1.

The compounds, methods and kits of the present disclosure find use in routine monitoring of by immunoassays. In certain embodiments, these immunoassays provide simple automated tests adapted to standard laboratory equipment with a quick turn-around time. As described herein, in order to provide such immunoassays, antibodies to MTX are produced. The derivatives and immunogens are designed to impart, through the corresponding antibodies, specific reactivity to MTX and less than 0.1% cross reactivity to 7-OH MTX as well as detectability of MTX to 0.03 micromole/liter.

The instructions included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate or scanned from a QR code for directions to download or provide instructions for use.

Notwithstanding the appended claims, the present disclosure is also defined by the following clauses:

Clause 1. A compound of Formula 1:

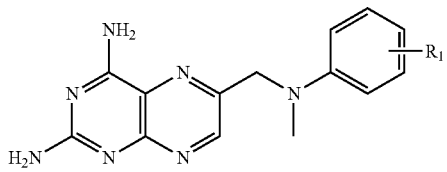

wherein:
R$^1$ is —Y—Z;
Y is a linking group; and
Z is selected from the group consisting of hydrogen, OH, SH, S-acyl, O-alkyl, halogen, NH$_2$, epoxy, maleimidyl, haloacetamide, carboxyl, activated carboxyl, N3 and alkenean immunogenic carrier, a protein, a label, and a solid support, and salts thereof.

Clause 2. The compound of Clause 1, wherein the linking group comprises 1 to 15 carbon atoms and/or 0 to 6 heteroatoms.

Clause 3. The compound of Clause 1 or Clause 2, wherein the linking group is selected from the group consisting of —(CH$_2$)$_n$C(O)—, —C(O)(CH$_2$)$_n$—, —C(O)(CH$_2$)$_n$NHC(O)—, —C(O)(CH$_2$)$_n$NHC(O)(CH$_2$)$_n$—, —(CH$_2$)$_n$SCH$_2$C(O)—, —(CH$_2$)$_n$C(O)NH(CH$_2$)$_n$—, —(CH$_2$)$_n$NHC(O)—, —(CH$_2$)$_n$NHC(O)(CH$_2$)$_n$—, —(CH$_2$)$_n$NHC(O)(CH$_2$)$_n$O(CH$_2$)$_n$NHC(O)(CH$_2$)$_n$—, —(CH$_2$)$_n$NHC(O)(CH$_2$)$_n$NHC(O)(CH$_2$)$_n$—, —NH(CH$_2$)$_n$C(O)—, —(CH$_2$)$_n$—, —C(O)NH(CH$_2$CH$_2$O)$_m$(CH$_2$)$_n$NHC(O)(CH$_2$)$_n$—, and —(CH$_2$)$_n$(heterocyclyl)S(CH$_2$)$_n$C(O)—, each m is independently an integer from 1 to 10, and each n is independently an integer from 1 to 10, and salts thereof.

Clause 4. The compound of any one of Clauses 1 to 3, wherein Z is a protein.

Clause 5. The compound of Clause 4, wherein the protein is an immunogenic carrier selected from the group consisting of a hemocyanin, a globulin, and an albumin.

Clause 6. The compound of Clause 5, wherein the immunogenic carrier is bovine serum albumin (BSA) or keyhole limpet hemocyanin (KLH).

Clause 7. The compound of Clause 1, wherein Z is an immunogenic carrier and the immunogenic carrier is a polysaccharide.

Clause 8. The compound of any one of Clauses 1 to 3, wherein Z is a label.

Clause 9. The compound of Clause 8, wherein the label is an enzyme.

Clause 10. The compound of Clause 9, wherein the enzyme is selected from the group consisting of an alkaline phosphatase, a β-galactosidase and a horseradish peroxidase.

Clause 11. The compound of Clause 9, wherein the enzyme is glucose-6-phosphate dehydrogenase (G6PDH).

Clause 12. The compound of any one of Clauses 1 to 11, wherein the linking group comprises an acyl or alkyl group attached to the phenyl group.

Clause 13. The compound of any one of Clauses 1 to 11, wherein the linking group comprises an alkyl or substituted alkyl group attached to the phenyl group.

Clause 14. An antibody that specifically binds to the compound of Formula 1 of any one of Clauses 1 to 13.

Clause 15. The antibody of Clause 14, wherein the antibody competes for binding to the compound with an antibody comprising:
a variable heavy chain (V$_H$) polypeptide comprising
a V$_H$ CDR1 comprising the amino acid sequence (SEQ ID NO: 2),
a V$_H$ CDR2 comprising the amino acid sequence (SEQ ID NO: 3), and
a V$_H$ CDR3 comprising the amino acid sequence (SEQ ID NO: 4); and
a variable light chain (V$_L$) polypeptide comprising
a V$_L$ CDR1 comprising the amino acid sequence (SEQ ID NO: 6),
a V$_L$ CDR2 comprising the amino acid sequence (SEQ ID NO: 7), and
a V$_L$ CDR3 comprising the amino acid sequence (SEQ ID NO: 8).

Clause 16. The antibody of Clause 15, wherein the antibody comprises a variable heavy chain (V$_H$) polypeptide comprising an amino acid sequence having 70% or greater identity to the amino acid sequence set forth in SEQ ID NO: 1.

Clause 17. The antibody of Clause 14, wherein the antibody comprises:
a variable heavy chain (V$_H$) polypeptide comprising
a V$_H$ CDR1 comprising the amino acid sequence (SEQ ID NO: 10),
a V$_H$ CDR2 comprising the amino acid sequence (SEQ ID NO: 11), and
a V$_H$ CDR3 comprising the amino acid sequence (SEQ ID NO: 12); and
a variable light chain (V$_L$) polypeptide comprising
a V$_L$ CDR1 comprising the amino acid sequence (SEQ ID NO: 14),
a V$_L$ CDR2 comprising the amino acid sequence (SEQ ID NO: 15), and
a V$_L$ CDR3 comprising the amino acid sequence (SEQ ID NO: 16).

Clause 18. The antibody of Clause 17, wherein the antibody comprises:
a variable heavy chain (V$_H$) polypeptide comprising an amino acid sequence having 70% or greater identity to the amino acid sequence set forth in SEQ ID NO: 9; and
a variable light chain (V$_L$) polypeptide comprising an amino acid sequence having 70% or greater identity to the amino acid sequence set forth in SEQ ID NO: 13.

Clause 19. The antibody of Clause 14, wherein the antibody competes for binding to the compound with an antibody comprising:
a variable heavy chain (V$_H$) polypeptide comprising
a V$_H$ CDR1 comprising the amino acid sequence (SEQ ID NO: 18),
a V$_H$ CDR2 comprising the amino acid sequence (SEQ ID NO: 19), and
a V$_H$ CDR3 comprising the amino acid sequence (SEQ ID NO: 20); and
a variable light chain (V$_L$) polypeptide comprising
a V$_L$ CDR1 comprising the amino acid sequence (SEQ ID NO: 22), a V<sub>L</sub> CDR2 comprising the amino acid sequence (SEQ ID NO: 23), and
a V<sub>L</sub> CDR3 comprising the amino acid sequence (SEQ ID NO: 24).

Clause 20. The antibody of Clause 19 wherein the antibody comprises:
a variable heavy chain (V<sub>H</sub>) polypeptide comprising an amino acid sequence having 70% or greater identity to the amino acid sequence set forth in SEQ ID NO: 17; and
a variable light chain (V<sub>L</sub>) polypeptide comprising an amino acid sequence having 70% or greater identity to the amino acid sequence set forth in SEQ ID NO: 21.

Clause 21. The antibody of any one of Clauses 14 to 20 wherein the antibody is selected from the group consisting of: an IgG, Fv, single chain antibody, scFv, Fab, F(ab')$_2$, and Fab'.

Clause 22. The antibody of any one of Clauses 14 to 21, wherein the antibody is an IgG.

Clause 23. The antibody of Clause 22, wherein the antibody is an IgG$_1$.

Clause 24. The antibody of any one of Clauses 14 to 21, wherein the antibody is a Fab.

Clause 25. The antibody of any one of Clauses 14 to 21, wherein the antibody is a single chain antibody.

Clause 26. The antibody of Clause 25, wherein the antibody is an scFv.

Clause 27. The antibody of any one of Clauses 14 to 26, wherein the antibody is a monoclonal antibody.

Clause 28. The antibody of Clause 14, wherein the antibody is a polyclonal antibody.

Clause 29. The antibody of Clause 28, wherein the antibody is a rabbit polyclonal antibody.

Clause 30. The antibody of any one of Clauses 14 to 29, wherein the antibody further specifically has 0.1% cross reactivity with 7-hydroxy methotrexate.

Clause 31. A nucleic acid encoding a variable heavy chain (V<sub>H</sub>) polypeptide, a variable light chain (V<sub>L</sub>) polypeptide, or both, of an antibody of any one of Clauses 14 to 30.

Clause 32. An expression vector comprising the nucleic acid of Clause 31.

Clause 33. A cell comprising the nucleic acid of Clause 31 or the expression vector of Clause 32.

Clause 34. A cell comprising:
a first nucleic acid encoding a variable heavy chain (V<sub>H</sub>) polypeptide of the antibody of any one of Clauses 14 to 30, and
a second nucleic acid encoding a variable light chain (V<sub>L</sub>) polypeptide of the antibody of any one of Clauses 14 to 30.

Clause 35. The cell of Clause 34, comprising:
a first expression vector comprising the first nucleic acid; and
a second expression vector comprising the second nucleic acid.

Clause 36. A method of making an antibody, comprising culturing the cell of any one of Clauses 33 to 35 under conditions suitable for the cell to express the antibody, wherein the antibody is produced.

Clause 37. A composition comprising:
the compound of Formula 1 of any one of Clauses 1 to 13; or
the antibody of any one of Clauses 14 to 30; or
the nucleic acid of Clause 31; or
the expression vector of Clause 31; or
the cell of any one of Clauses 33 to 34; or
any combination thereof.

Clause 38. The composition of Clause 37, wherein the composition is present in a liquid medium.

Clause 39. The composition of Clause 38, wherein the composition is present in a lyophilized form.

Clause 40. A method for determining an amount of a methotrexate analyte in a medium, the method comprising:
contacting in a medium
a sample suspected of containing at least one methotrexate analyte, and
the antibody of any one of Clauses 14 to 30; and
determining the presence or absence of a complex comprising the methotrexate analyte and the antibody,
wherein the presence of the complex indicates the presence of the methotrexate analyte in the sample.

Clause 41. The method according to Clause 40, wherein the medium further comprises the compound of Formula 1 of any one of Clauses 1 to 13.

Clause 42. The method according to Clause 41, wherein Z is a label.

Clause 43. The method according to Clause 42, wherein the label is an enzyme.

Clause 44. The method according to Clause 43, wherein the enzyme is selected from the group consisting of: an alkaline phosphatase, a β-galactosidase, and a horseradish peroxidase.

Clause 45. The method according to Clause 44 wherein the enzyme is glucose-6-phosphate dehydrogenase (G6PDH).

Clause 46. The method according to any one of Clauses 40 to 45, wherein the determining comprises detecting the presence of an enzymatic reaction product of the compound.

Clause 47. A kit for determining an amount of at least one methotrexate analyte in a sample, the kit comprising:
the antibody of any one of Clauses 14 to 30; and
instructions for using the antibody to determine an amount of methotrexate analyte in a sample.

Clause 48. The kit of Clause 47, wherein the antibody specifically has a cross reactivity of less than 0.1% to 7 hydroxy methotrexate.

Clause 49. The kit of Clause 47, further comprising instructions for determining an amount of the methotrexate with cross reactivity of less than 0.1% to folic acid, folinic acid, dihydrofolic acid and tetrahydrofolic acid Clause 50. The kit of Clause 47, wherein the antibody is present in a lyophilized form.

Clause 51. The kit of any one of Clauses 47-50, further comprising a compound of Formula 1 of any one of Clauses 1 to 13.

Clause 52. The kit of Clause 51, wherein Z is a label.

Clause 53. The kit of Clause 52, wherein the label is an enzyme.

Clause 54. The kit of Clause 53, wherein the enzyme is selected from the group consisting of: an alkaline phosphatase, a β-galactosidase, and a horseradish peroxidase.

Clause 55. The kit of Clause 54, wherein the enzyme is glucose-6-phosphate dehydrogenase (G6PDH).

Clause 56. The kit of any one of Clauses 52 to 55, wherein the compound is present in a lyophilized form.

Clause 57. A kit for determining an amount of methotrexate analyte in a sample, the kit comprising:
the compound of Formula 1 of any one of Clauses 1 to 13; and
instructions for using the compound to determine an amount of at least one methotrexate analyte in a sample.

Clause 58. The kit of Clause 57, wherein Z is a label.

Clause 59. The kit of Clause 58, wherein the label is an enzyme.

Clause 60. The kit of Clause 59, wherein the enzyme is selected from the group consisting of an alkaline phosphatase, a β-galactosidase, and a horseradish peroxidase.

Clause 61. The kit of Clause 60, wherein the enzyme is glucose-6-phosphate dehydrogenase (G6PDH).

Clause 62. The kit of any one of Clauses 57 to 61, wherein the compound is present in lyophilized form.

Clause 63. The kit of any one of Clauses 57 to 62, further comprising the antibody of any one of Clauses 14 to 30.

Clause 64. The kit of Clause 63, wherein the antibody specifically has a cross reactivity of 0.1% with 7 hydroxy methotrexate Clause 65. The kit of any one of Clauses 57 to 64, wherein the antibody is present in lyophilized form.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

In relation to the compounds and conjugates and immunogens, the following abbreviations are used: DCM is dichloromethane; DMF is N,N-dimethylformamide; EDTA is ethylenediaminetetraaceticacid; KLH is keyhole limpet hemocyanin; SATA is N-succinimidyl S-acetylthioacetate; TFA is trifluoroacetic acid; EDCI is 1-ethyl-3(3-dimethylaminopropyl)carbodiimidehydrochloride; NHS is N-hydroxysuccinimide; DTT is dithioerythritol; G6PDH is Glucose-6-Phosphate Dehydrogenase; EtOAc is ethyl acetate; BSA is bovine serum albumin; MeCN is Acetonitrile; t-Boc is tert-butyloxycarbonyl protecting group; TLC is thin layer chromatography; MeOH is methanol; AcOH is acetic acid; PBST is phosphate buffered saline with Tween-20; TMB is 3,3',5,5'-tetramethylbenzidine; PBMC is peripheral blood mononuclear cell.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978; R. C. Larock Comprehensive Organic Transformations, Second Edition, Wiley-VCH 1999).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969. Analytical techniques such as LC-MS is Liquid chromatography with mass spectrometry detection, 1H-NMR means proton nuclear magnetic resonance with shifts denoted in ppm downfield of tetramethyl silane (TMS).

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1—Synthesis of DAMP-1 Hapten

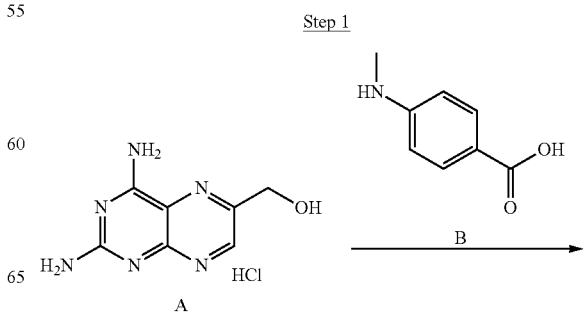

-continued

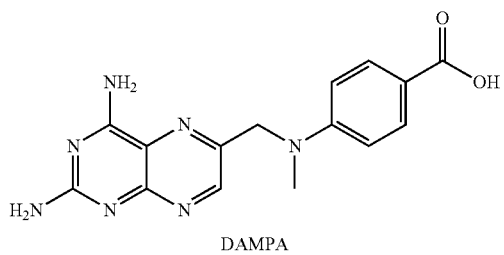

DAMPA

To a solution of Compound A, (2,4-diaminopteridin-6-yl) methanol hydrochloride, (5.0 g, 21.87 mmol) in dry DMAC (85 mL) was added Ph₃PBr (27.7 g, 65.61 mmol) at RT for 4 h, to this mixture was added DIEA (12.7 g, 98.42 mmol) and Compound B (4.5 g, 29.52 mmol) at ambient temperature and reaction stirred overnight. The resulting mixture was poured into 0.33M aq NaOH and the precipitate was filtered. The filtrate was adjusted to pH=5.5 with 10% acetic acid and the resulting precipitate was collected through filtration, washed with water and diethyl ether, then dried at 60° C. overnight to obtain DAMPA as an orange solid (4.9 g, 69.0%). LCMS: Rt=1.398 min; m/z calculated for [M+H]⁺ 326.1, found 326.1.

Step 2

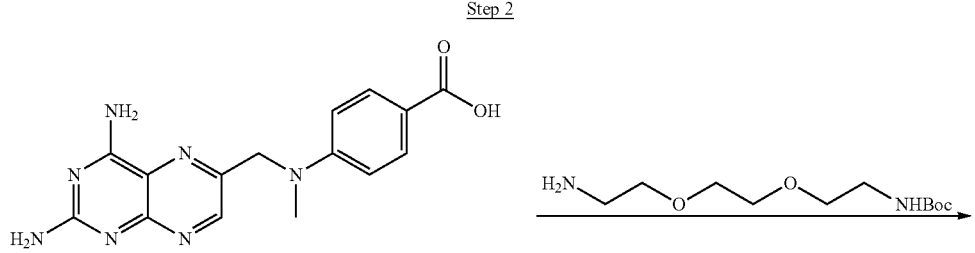

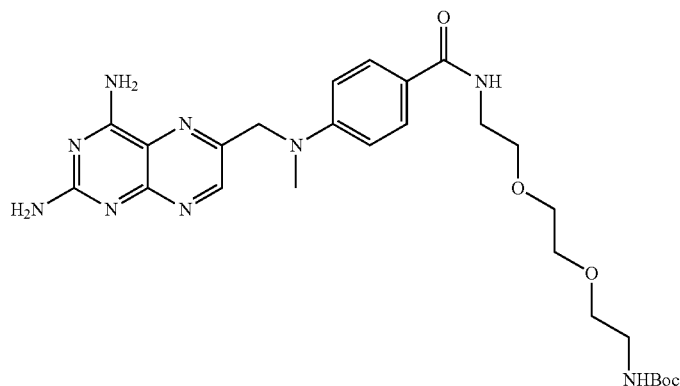

To a solution of 4-(((2,4-diaminopteridin-6-yl)methyl)(methyl)amino)benzoic acid, DAMPA, (1.65 g, 5.072 mmol) in dry DMSO (15 mL) was added TSTU (4.6 g, 15.22 mmol) and DIEA (2.0 g, 15.22 mmol) at RT for 2 h, the mixture was added tert-butyl (2-(2-(2-aminoethoxy)ethoxy)ethyl)carbamate (2.5 g, 10.14 mmol) in dry DMSO (10 mL) at RT for overnight. The mixture was added water extracted with EtOAc. The combined organic layers were dried over $Na_2SO_4$ and concentrated in vacuo. The residue was purified by column chromatography ($CH_2Cl_2$/MeOH=80/1 to 15/1, v/v) to afford an orange crude solid. The crude product was recrystallized to get an orange solid (383 mg, 13.7%).

TLC: $R_f$=0.30 (silica gel, $CH_2Cl_2$/MeOH=15/1, v/v)
LCMS: $R_t$=2.732 min; m/z calculated for $[M+H]^+$ 556.3, found 556.3.
HPLC: $R_t$=9.016 min; 95%@214; 98%@254 nm Step 3

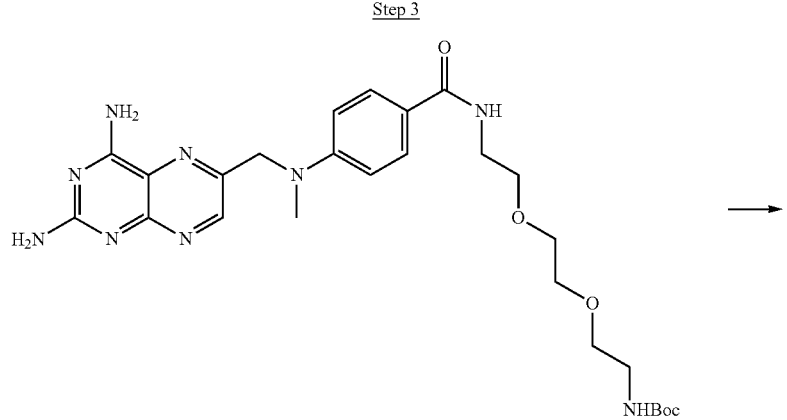

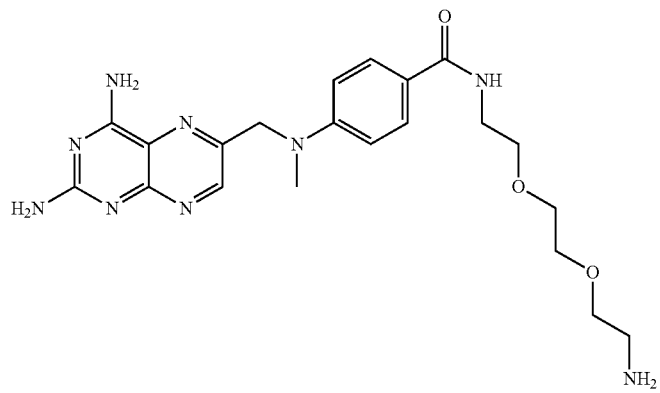

To a solution of tert-butyl (2-(2-(2-(4-(((2,4-diaminopteridin-6-yl)methyl)(methyl)amino)benzamido)ethoxy)ethoxy)ethyl)carbamate (383 mg, 0.6893 mmol) was added HCl/dioxane (15 mL) at RT for overnight, the mixture was concentrated in vacuo and then added $H_2O$ (30 ml) and NaOH (1.2 g, 30.0 mmol) at RT for 2 h. The resulting mixture was filtered and the filter was lyophilized to get an orange solid (252 mg, 80.3%).

LCMS: $R_t$=3.205 min; m/z calculated for $[M+H]^+$ 456.2, found 456.3.
HPLC: $R_t$=8.305 min; 98%@214; 98%@254 nm.

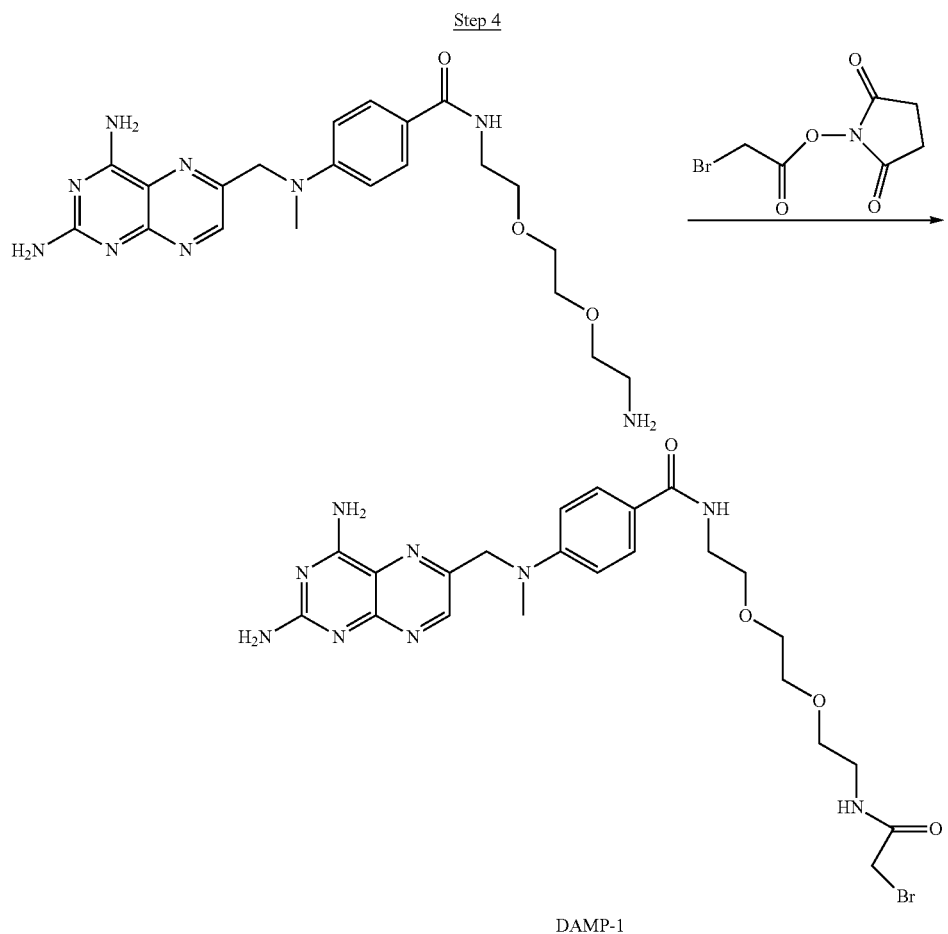

DAMP-1

Example 2—Synthesis of DAMP-2 Hapten

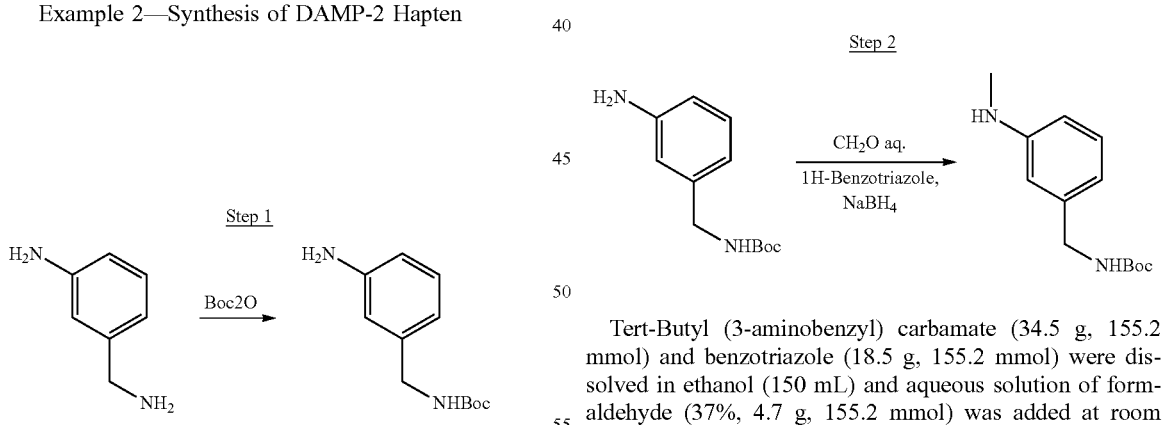

To a solution of 3-(aminomethyl)aniline (40.0 g, 327.60 mmol) in THF (660 mL) was added Boc$_2$O (38.7 g, 327.60 mmol) at 0° C. for 1 h. The reaction mixture was concentrated and to get a yellow solid (35.0 g, 48.0%).

LCMS: R$_f$=2.553 min; m/z calculated for [M+H]$^+$ 223.1. Found M+H$^+$=223.1

Tert-Butyl (3-aminobenzyl) carbamate (34.5 g, 155.2 mmol) and benzotriazole (18.5 g, 155.2 mmol) were dissolved in ethanol (150 mL) and aqueous solution of formaldehyde (37%, 4.7 g, 155.2 mmol) was added at room temperature. The mixture was stirred overnight and the solvent was evaporated. The residue was dissolved in THF (146 mL) and sodium borohydride (8.8 g, 282.8 mmol) was added at room temperature. The mixture was stirred for 4 hrs. Saturated aqueous sodium hydrogen carbonate and ethyl acetate were added and the mixture was subjected to extraction. The organic layer was dried (Na$_2$SO$_4$) and concentrated under reduced pressure. The residue was purified by silica gel chromatography to give the title compound (17.0 g, yield 45%).

LCMS: R$_f$=2.774 min; m/z calculated for [M+H]$^+$ 237.1, Found 237.1

Step 3

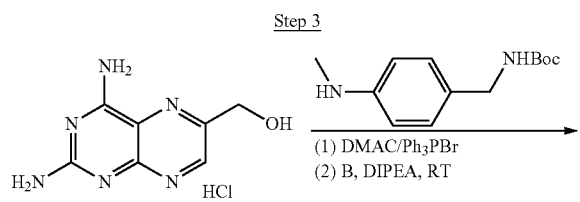

(1) DMAC/Ph₃PBr
(2) B, DIPEA, RT

Step 4

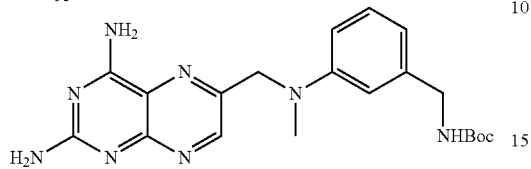

HCl/dioxane
─────────
NaOH H2O

To a solution of (2,4-diaminopteridin-6-yl)methanol hydrochloride (6.0 g, 26.03 mmol) in dry DMAC (75 mL) was added Ph₃PBr (39.6 g, 78.12 mmol) at RT for overnight, the mixture was added DIEA (20.21 g, 98.42 mmol) and B (11.05 g, 39.06 mmol) at RT for overnight. The resulting mixture was poured into 0.33M aq NaOH and the precipitate was filtered. The filtrate was adjusted to pH=5.5 with 10% acetic acid and the resulting precipitate was collected through filtration, washed with water and diethyl ether, then dried at 60° C. overnight to obtain a as an orange solid (4.8 g, 41.0%). LCMS: $R_t$=3.083 min; m/z calculated for [M+H]⁺411.3, found 411.3.

HPLC: $R_t$=9.249 min; 79% @214 nm; 82%@254 nm

To a solution of tert-butyl 6-(((3-(aminomethyl)phenyl)(methyl)amino)methyl)pteridine-2,4-diamine (2.1 g, 5.1 mmol) was added HCl/dioxane (50 mL) at RT for overnight, the mixture was concentrated in vacuo and then added H₂O (100 ml) and NaOH (4 g) at RT for 2 h. The resulting mixture was filtered and the filter was lyophilized to get yellow solid (1.5 g mg, 94.3%).

LCMS: $R_t$=0.909 min; m/z calculated for [M+H]⁺ 312.2, found. 312.2.

HPLC: $R_t$=2.996 min; 100%@214; 100%@254 nm

Step 5

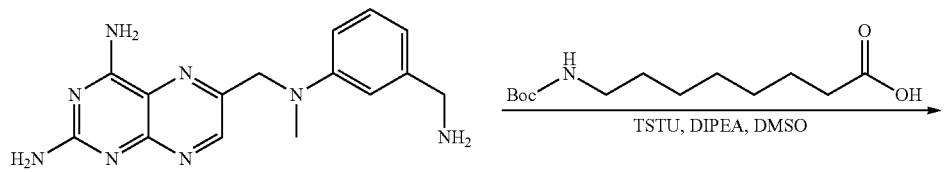

TSTU, DIPEA, DMSO

To a solution of 8-((tert-butoxycarbonyl)amino)octanoic acid (828 mg, 1.6 mmol) in dry DMSO (10 mL) was added TSTU (722 mg, 2.4 mmol) and DIEA (619 mg, 4.8 mmol) at RT for 10 min, the mixture was added 6-(((3-(aminomethyl)phenyl)(methyl)amino)methyl)pteridine-2,4-diamine (500 mg, 1.6 mmol) at RT for 15 min. The mixture was added water 100 ml at rt for 5 min. The resulting mixture was filtered and the filter was lyophilized to get yellow solid (500 mg, 56%).

LCMS: $R_t$=3.103 min; m/z calculated for [M+H]$^+$ 552.4, found. 552.4.

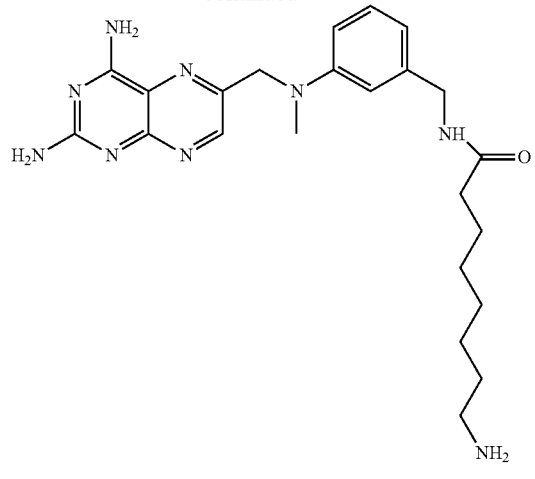

-continued

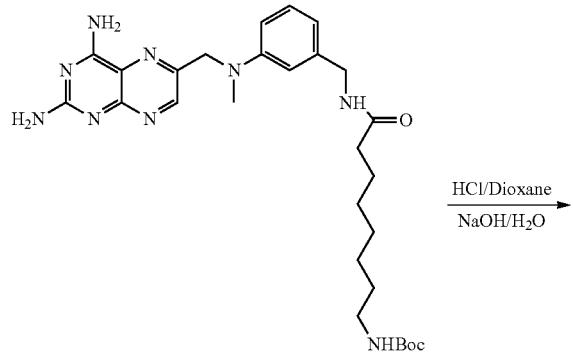

To a solution of tert-butyl (8-((3-(((2,4-diaminopteridin-6-yl)methyl)(methyl)amino)benzyl)amino)-8-oxooctyl)carbamate (500 mg, 0.9 mmol) was added HCl/dioxane (20 mL) at RT for overnight, the mixture was concentrated in vacuo and then added H$_2$O (100 ml) and NaOH (4 g) at RT for 2 h. The resulting mixture was filtered and the filter was lyophilized to get yellow solid (280 mg, 68%).

LCMS: $R_t$=3.492 min; m/z calculated for [M+H]$^+$ 452.3, found. 452.3.

HPLC: $R_t$=6.640 min; 100%@214; 100%@254 nm

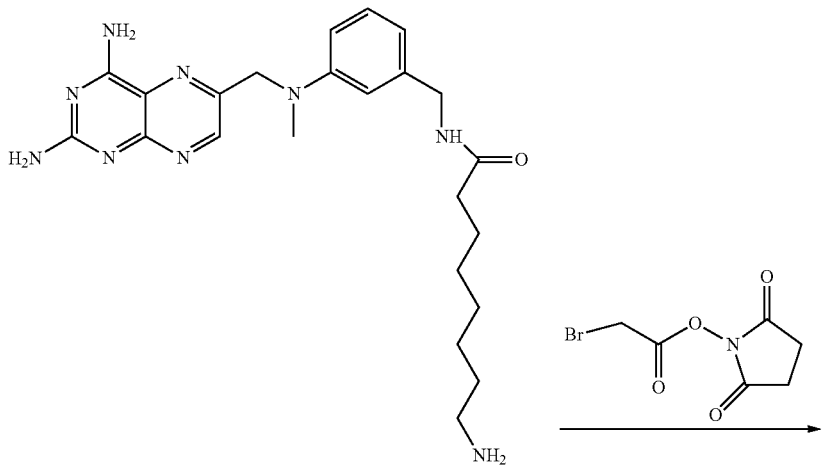

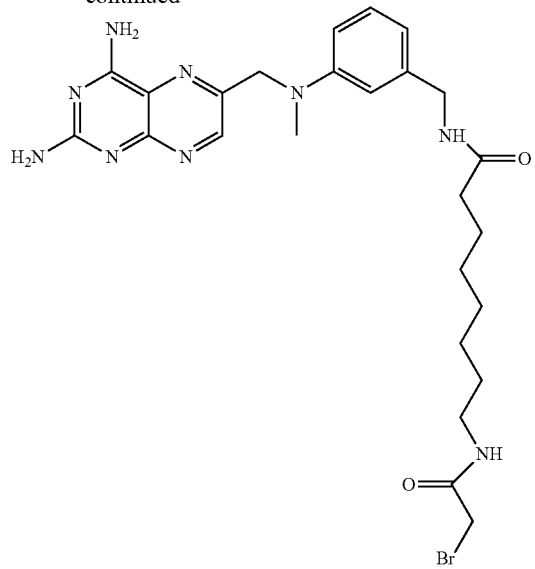

To a solution of the amino compound prepared in step 6 above (745 mg, 1.61 mmol) in DMF (5 mL) at 0° C. was added 2,5-dioxopyrrolidin-1-yl 2-bromoacetate (454 mg, 1.93 mmol). The resulting solution was stirred at RT for 3 hours. Then, the reaction solution was purified by Biotage Isolera One (C18 column, eluting with 10% to 90% MeCN/ $H_2O$, containing 0.1% TFA) to afford the title compound DAMP-2 (360 mg, 62% yield) as a brown solid.

MS calculated m/z 572.5, found M+H$^+$573.5

Example 3—Synthesis of DAMP-3 Hapten

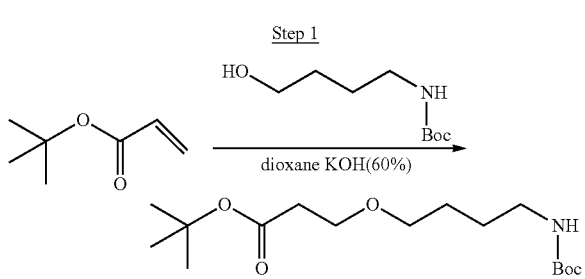

To a solution of tert-butyl acrylate (10.1 0.8 mol) and tert-butyl (4-hydroxybutyl) carbamate (10 g 0.05 mol) in dioxane was added 60% KOH solution (2 mL) the reaction mixture stirred overnight at 25° C. The reaction was monitored by TLC, and more KOH solution was added until most of the starting tert-butyl (4-hydroxybutyl) carbamate was consumed. The reaction mixture was then mixed with DCM, and washed 3 times with deionized water and once with brine. The organic layer was recovered, dried over $Na_2SO_4$ and the solvent removed via rotary evaporation. The resulting oil was purified on a silica column using petroleum ether/ethyl acetate (10:1) to get the Boc protected amino alcohol as a white oil (7 g, 43%).

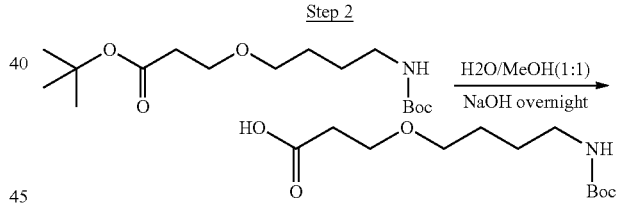

To a solution of tert-butyl 3-(4-((tert-butoxycarbonyl) amino)butoxy)propanoate (5 g, 15 mmol) in MeOH/$H_2O$ (15 ml/15 ml) was added NaOH (1.3 g. 31 mmol) at rt for overnight. The reaction mixture was concentrated and used next step 3 (below).

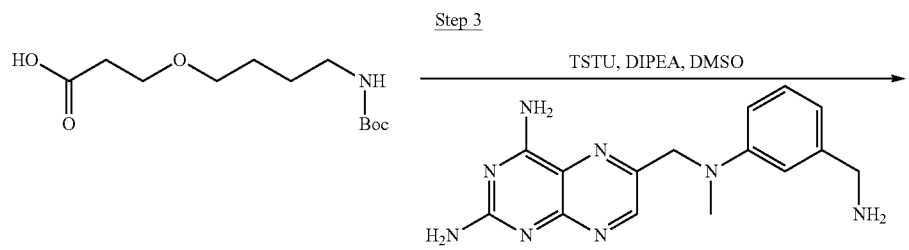

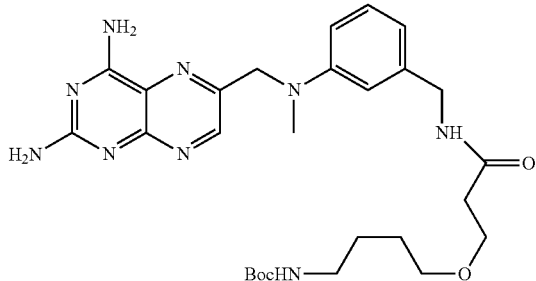

To a solution of 3-(4-((tert-butoxycarbonyl)amino)butoxy)propanoic acid (3.4 g, 13.2 mmol) in dry DMSO (10 mL) was added TSTU (993 mg, 3.3 mmol) and DIEA (851 mg, 6.6 mmol) at RT for 10 min, the mixture was added 6-(((3-(aminomethyl)phenyl)(methyl)amino)methyl)pteridine-2,4-diamine (700 mg, 2.2 mmol) at RT for 15 min. The mixture was added water 100 ml at rt for 5 min. The resulting mixture was filtered and the filter was lyophilized to get a yellow solid (700 mg, 58%).

LCMS: $R_t$=2.901 min; m/z calculated for [M+H]$^+$ 554.4, found. 554.4.

Step 4

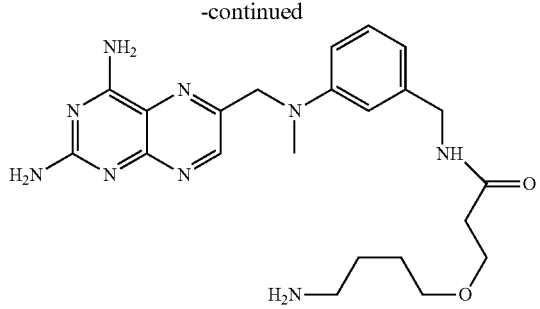

HCl/Dioxane
NaOH/H$_2$O

To a solution of tert-butyl (4-(3-((3-(((2,4-diaminopteridin-6-yl)methyl)(methyl)amino)benzyl)amino)-3-oxopropoxy)butyl)carbamate (500 mg, 0.9 mmol) was added HCl/dioxane (20 mL) at RT for overnight, the mixture was concentrated in vacuo and then added H$_2$O (100 ml) and NaOH (4 g) at RT for 2 h. The resulting mixture was filtered and the filter was lyophilized to get yellow solid (310 mg, 77%).

LCMS: $R_t$=0.892 min; m/z calculated for [M+H]$^+$ 454.3, found. 454.3.

HPLC: $R_t$=5.135 min; 100%@214; 100%@254 nm

Step 5

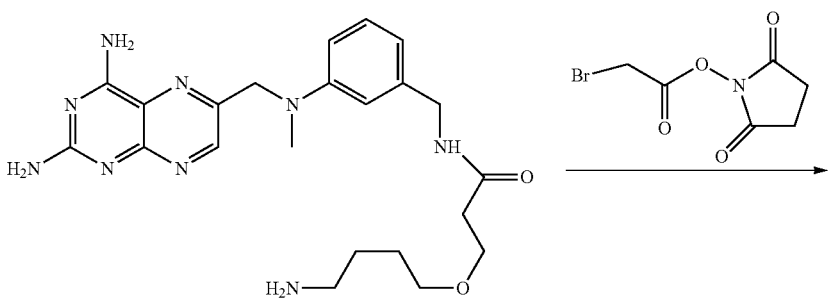

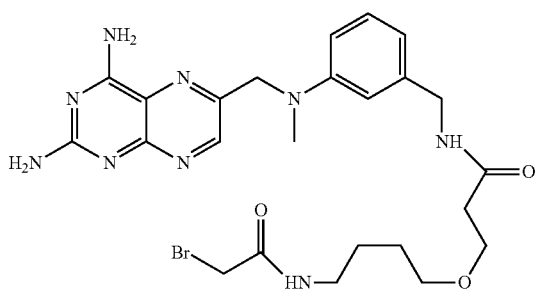

To a solution of the deprotected 3-(4-aminobutoxy)-N-(3-(((2,4-diaminopteridin-6-yl)methyl)(methyl)amino)benzyl)propenamide (454 mg, 1.00 mmol) in DMF (5 mL) at 0° C. was added 2,5-dioxopyrrolidin-1-yl 2-bromoacetate (580 mg, 1.28 mmol). The resulting solution was stirred at RT for 5 hours. Then, the reaction solution was purified by Biotage Isolera One (C18 column, eluting with 10% to 90% MeCN/H$_2$O, containing 0.1% TFA) to afford the title compound DAMP-3 (260 mg, 45%) of DAMP-3 as a yellow solid.

LS-MS purified, MS calculated m/z 574.5, found M+H+ 575.5 Example 4—Synthesis of DAMP-4 Hapten Step 1

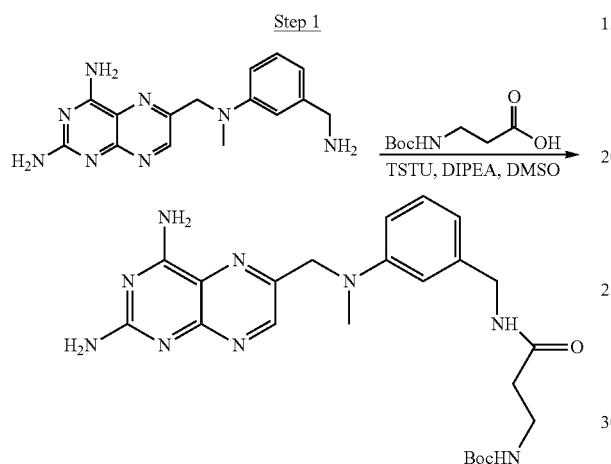

To a solution of 3-((tert-butoxycarbonyl)amino)propanoic acid (604 mg, 3.2 mmol) in dry DMSO (10 mL) was added TSTU (722 mg, 2.4 mmol) and DIEA (619 mg, 4.8 mmol) at RT for 10 min, the mixture was added 6-(((3-(aminomethyl)phenyl)(methyl)amino)methyl)pteridine-2,4-diamine (500 mg, 1.6 mmol) at RT for 15 min. The mixture was added water 100 ml at rt for 5 min. The resulting mixture was filtered and the filter was lyophilized to get yellow solid (470 mg, 71%).

LCMS: R$_t$=2.732 min; m/z calculated for [M+H]$^+$ 482.3, found. 482.3.

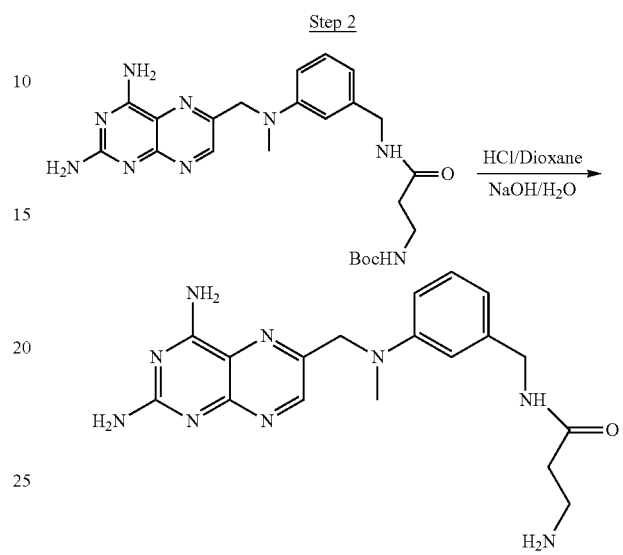

To a solution of tert-butyl (3-((3-(((2,4-diaminopteridin-6-yl)methyl)(methyl)amino)benzyl)amino)-3-oxopropyl)carbamate (470 mg, 0.9 mmol) was added HCl/dioxane (20 mL) at RT for overnight, the mixture was concentrated in vacuo and then added H$_2$O (100 ml) and NaOH (4 g) at RT for 2 h. The resulting mixture was filtered and the filter was lyophilized to get yellow solid (270 mg, 70%).

LCMS: R$_t$=0.892 min; m/z calculated for [M+H]$^+$ 382.2, found. 382.2.
HPLC: R$_t$=3.968 min; 100%@214; 100%@254
1H NMR: LQ-962-022, 400 MHz DMSO

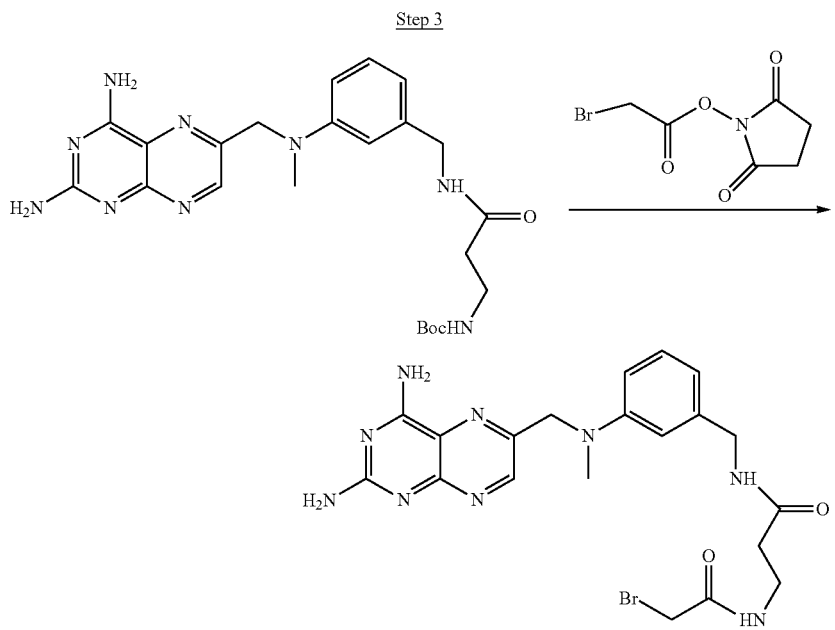

To a solution of 3-((3-(((2,4-diaminopteridin-6-yl)methyl)(methyl)amino)benzyl)amino)-3-oxopropyl)amine (500 mg, 1.61 mmol) in DMF (5 mL) at 0° C. was added 2,5-dioxopyrrolidin-1-yl 2-bromoacetate (454 mg, 1.93 mmol). The resulting solution was stirred at RT for 3 hours. Then, the reaction solution was purified by Biotage Isolera One (C18 column, eluting with 10% to 90% MeCN/H$_2$O, containing 0.1% TFA) to afford the title compound DAMP-4 (258 mg, 24% yield) as a brown solid.

LCMS: R$_t$=0.963 min; m/z calculated for [M+H]+, found. 431.0, 433.

HPLC: R$_t$=10.253 min; 90%@214; 91%@254 nm

Example 5—Synthesis of DAMP-5 Hapten

Step 1

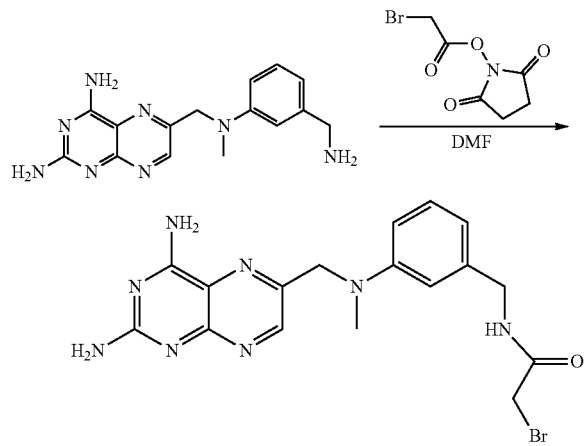

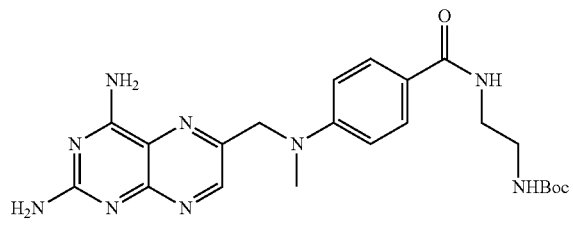

To a solution of 4-(((2,4-diaminopteridin-6-yl)methyl)(methyl)amino)benzoic acid, DAMPA, (1.65 g, 5.072 mmol) in dry DMSO (15 mL) was added TSTU (4.6 g, 15.22 mmol) and DIEA (2.0 g, 15.22 mmol) at RT for 2 h, the mixture was added tert-butyl 2-(2-aminoethyl)carbamate (1.7 g, 10.14 mmol) in dry DMSO (10 mL) at RT for overnight. The mixture was added water extracted with EtOAc. The combined organic layers were dried over Na$_2$SO$_4$ and concentrated in vacuo. The residue was purified by column chromatography (CH$_2$Cl$_2$/MeOH=80/1 to 15/1, v/v) to afford an orange crude solid. The crude product was recrystallized to get an orange solid (383 mg, 13.7%).

TLC: R$_f$=0.30 (silica gel, CH$_2$Cl$_2$/MeOH=15/1, v/v)

Step 2

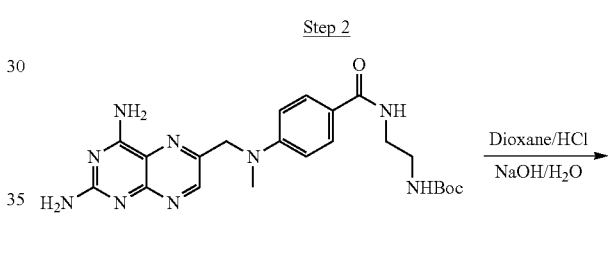

To a solution of 6-(((3-(aminomethyl)phenyl)(methyl)amino)methyl)pteridine-2,4-diamine (500 mg, 1.61 mmol) in DMF (5 mL) at 0° C. was added 2,5-dioxopyrrolidin-1-yl 2-bromoacetate (454 mg, 1.93 mmol). The resulting solution was stirred at RT for 3 hours. Then, the reaction solution was purified by Biotage Isolera One (C18 column, eluting with 10% to 90% MeCN/H$_2$O, containing 0.1% TFA) to afford the title compound (258 mg, 24% yield) as a brown solid.

LCMS: R$_t$=0.963 min; m/z calculated for [M+H]$^+$ 431.298, found. 431.0, 433.

HPLC: R$_t$=10.253 min; 90%@214; 91%@254 nm

Example 6—Synthesis of DAMP-6 Hapten

Step 1

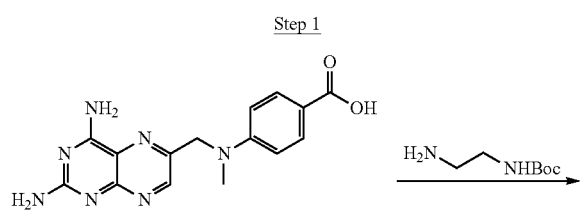

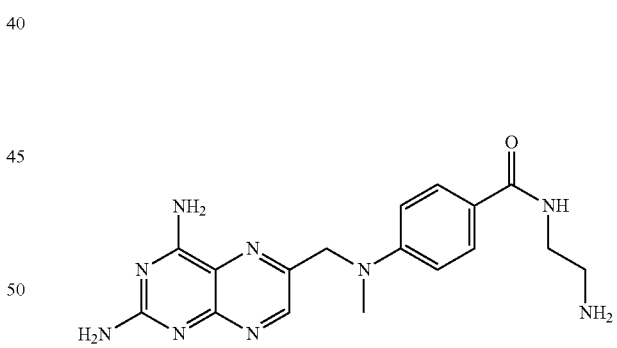

To a solution of tert-butyl (4-((2,4-diaminopteridin-6-yl)methyl)(methyl)amino)benzoyl)amino)-aminoethyl)carbamate (470 mg, 1.0 mmol) was added HCl/dioxane (20 mL) at RT for overnight, the mixture was concentrated in vacuo and then added H$_2$O (100 ml) and NaOH (4 g) at RT for 2 h. The resulting mixture was filtered and the filter was lyophilized to get yellow solid (270 mg, 70%).

LCMS: R$_t$=2.42 min; m/z calculated for [M+H] $^+$368.4, found. 368.4.

HPLC: R$_t$=3.968 min; 100%@214; 100%@254 nm

Step 3

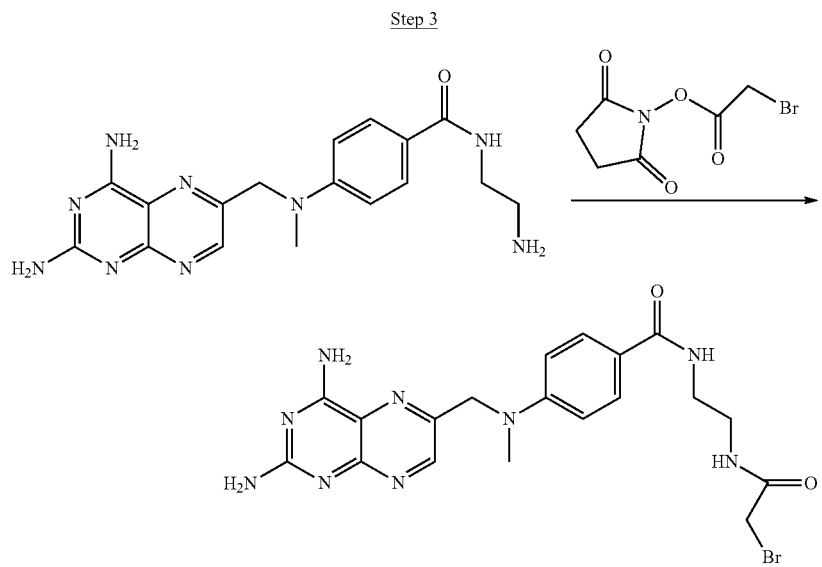

To a solution of 3-((3-(((2,4-diaminopteridin-6-yl)methyl)(methyl)amino)benzoyl)amino)-ethylamine (500 mg, 1.36 mmol) in DMF (5 mL) at 0° C. was added 2,5-dioxopyrrolidin-1-yl 2-bromoacetate (384 mg, 1.63 mmol). The resulting solution was stirred at RT for 3 hours. Then, the reaction solution was purified by Biotage Isolera One (C18 column, eluting with 10% to 90% MeCN/H$_2$O, containing 0.1% TFA) to afford the title compound (318 mg, 48% yield) as a brown solid.

LC-MS RT 5.83 min, MS calc M+H 489.3, Found 489.3

Example 7

Preparation DAMP-Y-S-BSA Conjugate

The lysine groups in BSA were thiolated by reaction with SATA at pH 9.0 in carbonate buffer. Hydrolysis by hydroxylamine gave the thiolated BSA-SH which was reacted with the DAMPA-Y bromoacetamides to give the DAMP-Y-S-BSA conjugates. The conjugates were purified by dialysis using a 10 kD Slide-A-Lyzer™ MWCO into 2×2 L of phosphate buffer at pH 7.4.

Figure 12:
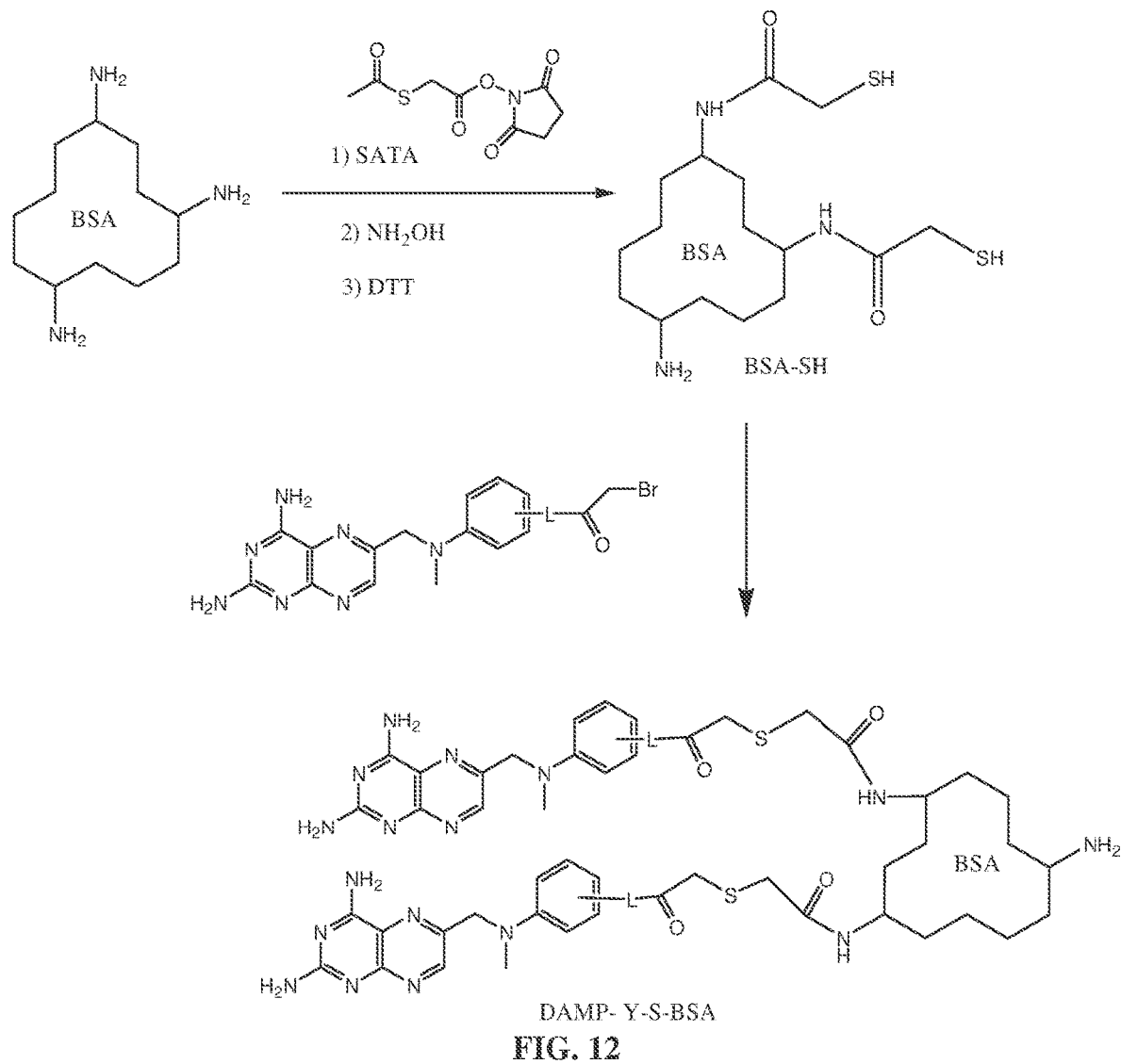
FIG. 12 shows the synthesis scheme for the DAMP-Y-S-BSA immunogen, according to embodiments of the present disclosure.
Figure 13:
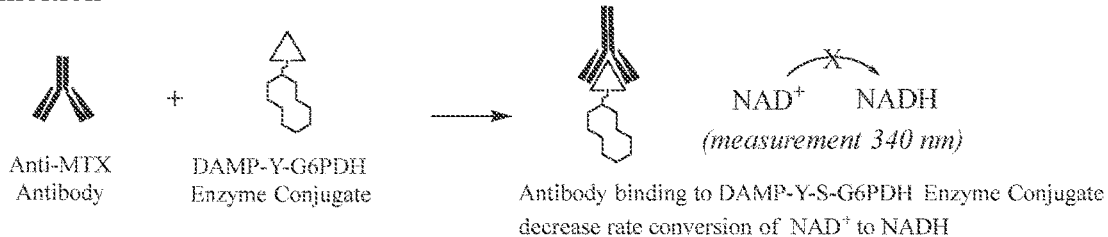
FIG. 13 shows the principle of the homogeneous enzyme immunoassay and the antibody screening technique, according to embodiments of the present disclosure.
Figure 13:
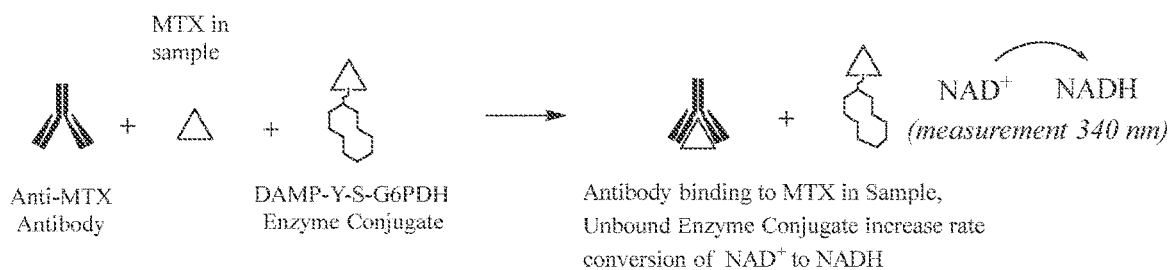

The DAMP-Y-S-BSA conjugate was used to screen B-cells and monoclonal antibodies by indirect ELISA to screen for antibodies from rabbit bleeds. (FIG. 12.)

Example 8

Preparation of DAMP—KLH Immunogens

Figure 11:
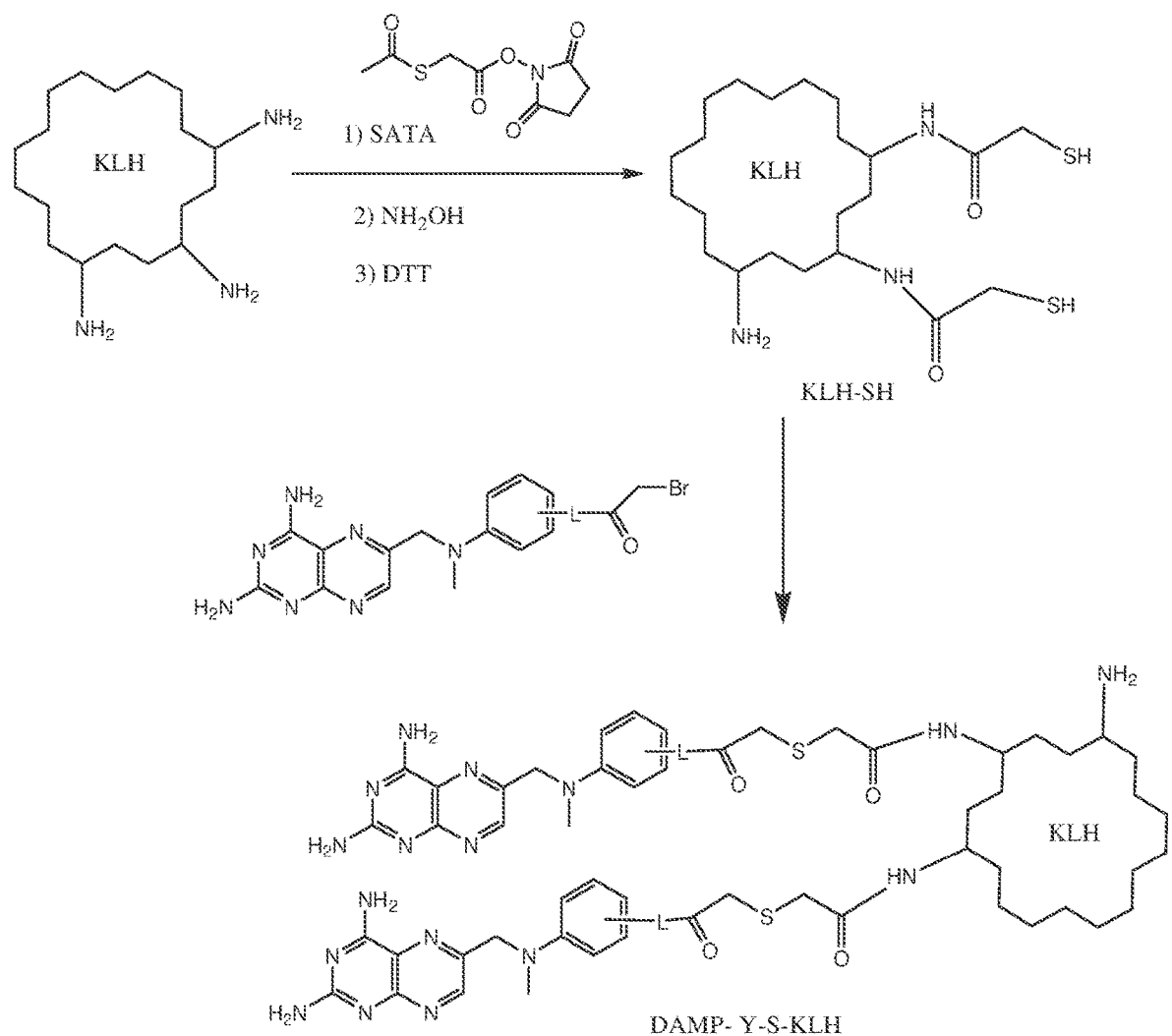
FIG. 11 shows the synthesis scheme for the DAMP-Y-S-KLH immunogen, according to embodiments of the present disclosure.

Hapten DAMP-Y (1 through 6 of the compounds shown above) was conjugated to KLH where thiol groups were chemically introduced to KLH. N-Succinimidyl-S-acetylthioacetate was reacted with the primary amines of KLH, which added protected sulfhydryls. Deprotection of protected sulfhydryls with hydroxyl amine produced the desired thiolated SH-KLH (FIG. 11). Conjugation of the DAMP bromoacetamide haptens with SH-KLH resulted in immunogen DAMP-Y-S-KLH (FIG. 11).
A) Preparation of SH-KLH Lyophilized KLH (20 mg) was reconstituted with deionized water and pH adjusted to 8.6 with 1.0 M carbonate-bicarbonate buffer. A solution of N-Succinimidyl S-acetylthioacetate was prepared (4.67 mg was dissolved in 92 µL of DMF to a concentration of 220 mM) and slowly added to the KLH solution over 4 hrs. The reaction mixture was stirred at room temperature while N-Succinimidyl S-acetylthioacetate was being added, then stirred in the cold-room (4° C.) for an additional 16 hours.

Deacylation to generate a sulfhydryl for use in cross-linking was accomplished by adding 200 µL of a deacetylation solution (0.7 M hydroxylamine solution in 12.5 mM NaH$_2$PO$_4$—Na$_2$HPO$_4$ buffer, pH 7). Contents were mixed and reaction incubated for 2 hours at room temperature resulting in the product SH-KLH (see FIG. 11). EDTA was added at the end of this reaction to a concentration of 1 mM.
b) Preparation of DAMP-Y-S-KLH Immunogen Dithiothreitol solution was added to the above SH-KLH solution for a total concentration of 1 mM to minimize disulfide bond formation. The pH was adjusted to 7.2 with 1 M carbonate-bicarbonate buffer. To the SH-KLH solution, 146 µl of the hapten DAMP-L-bromoacetamide dissolved in DMF (9.6 mg dissolved in 0.2 mL DMF) was added slowly over 4 to 5 hrs. The reaction was continued overnight at 4° C. The mixture was purified by dialysis using a 10,000 MWCO Slide-A-Lyzer* Dialysis Cassette (Pierce) in 2×2 liter NaH$_2$PO$_4$—Na$_2$HPO$_4$ buffer 12.5 mM, pH 7.0, at 2-8° C. This procedure yielded immunogen DAMP-Y-S-KLH.

Example 9

Preparation of DAMP-SH-G6PDH Conjugates

DAMP bromoacetamide haptens prepared as described in Examples 1-6 is designed for proteins containing cysteine groups such as mutant G6PDH (see U.S. Pat. Nos. 6,455, 288, 6,090,567, 6,033,890) or introduction of thiol-groups to G6PDH similarly as described in Example 8 by chemical reactions.

DAMP hapten (0.02 mmol) was dissolved in DMF (0.21 mL). The solution was stirred at room-temperature for 30 minutes. This DAMP solution was used as described below.

Dithiothreitol solution was added to mutant G6PDH at a concentration of 2 mM to reduce cysteine thiol groups connected in disulfide bonds to sulfhydryl groups. The resulting enzyme solution (0.9 mg, 1.5 mL) was adjusted to pH 7.2 with 1 M carbonate bi-carbonate buffer and mixed with approximately 340 fold molar excess (0.07 mL) of DAMP Bromoacetamide hapten. The reaction mixture was allowed to stir gently at 4° C. for 16 hours. Excess DAMP Bromoacetamide hapten was separated from the enzyme-hapten conjugate by passing the reaction mixture over a column of Sephadex G-50 in 12.5 mM $NaH_2PO_4$—$Na_2HPO_4$ buffer, pH 7.0. The column fractions containing the enzyme-hapten conjugate are pooled by measuring absorption at 280 nm to give conjugate DAMP-Y-S-G6PDH (see FIG. 10).

Example 10

Preparation of Polyclonal Antibodies to MTX

Twenty-four female white New Zealand rabbits were immunized by injecting subcutaneously 200 µg/rabbit of DAMP-Y-S-KLH immunogen, as prepared in Example 8, emulsified in Complete Freund's adjuvant. The rabbits were boosted every four weeks after the initial injection with 100 µg/rabbit of the same immunogen emulsified in Incomplete Freund's Adjuvant. One hundred and thirty-four days after the initial immunization, bleeds containing polyclonal antibodies from each rabbit were obtained from the central ear artery. The anti-serum from these bleeds containing DAMP-Y-S-KLH antibodies were evaluated in a homogeneous assay format by measuring maximum antibody inhibition of enzyme conjugate DAMP-Y-S-G6PDH and modulation in the presence of MTX.

Figure 3:
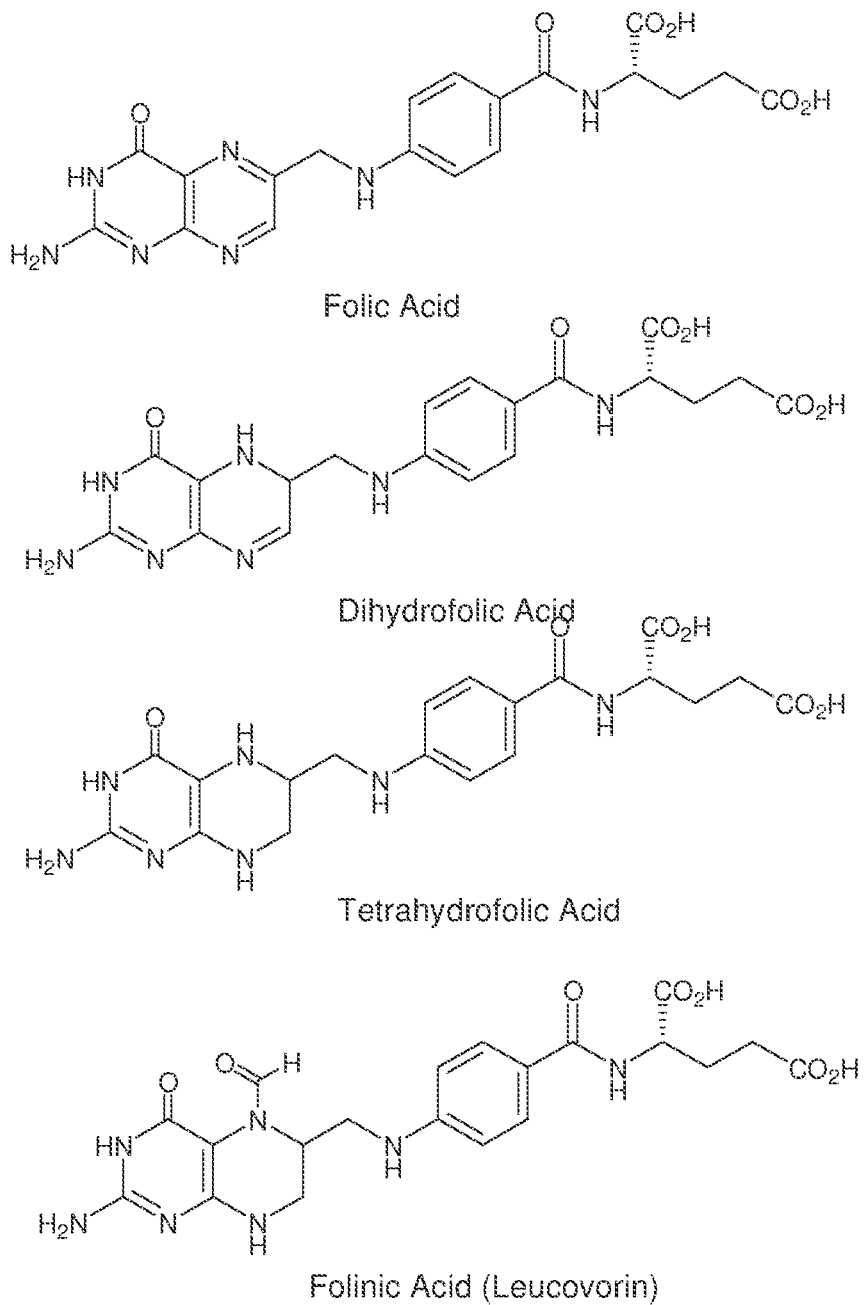
FIG. 3 shows chemical structures of structural analogs of MTX.
Figure 4:
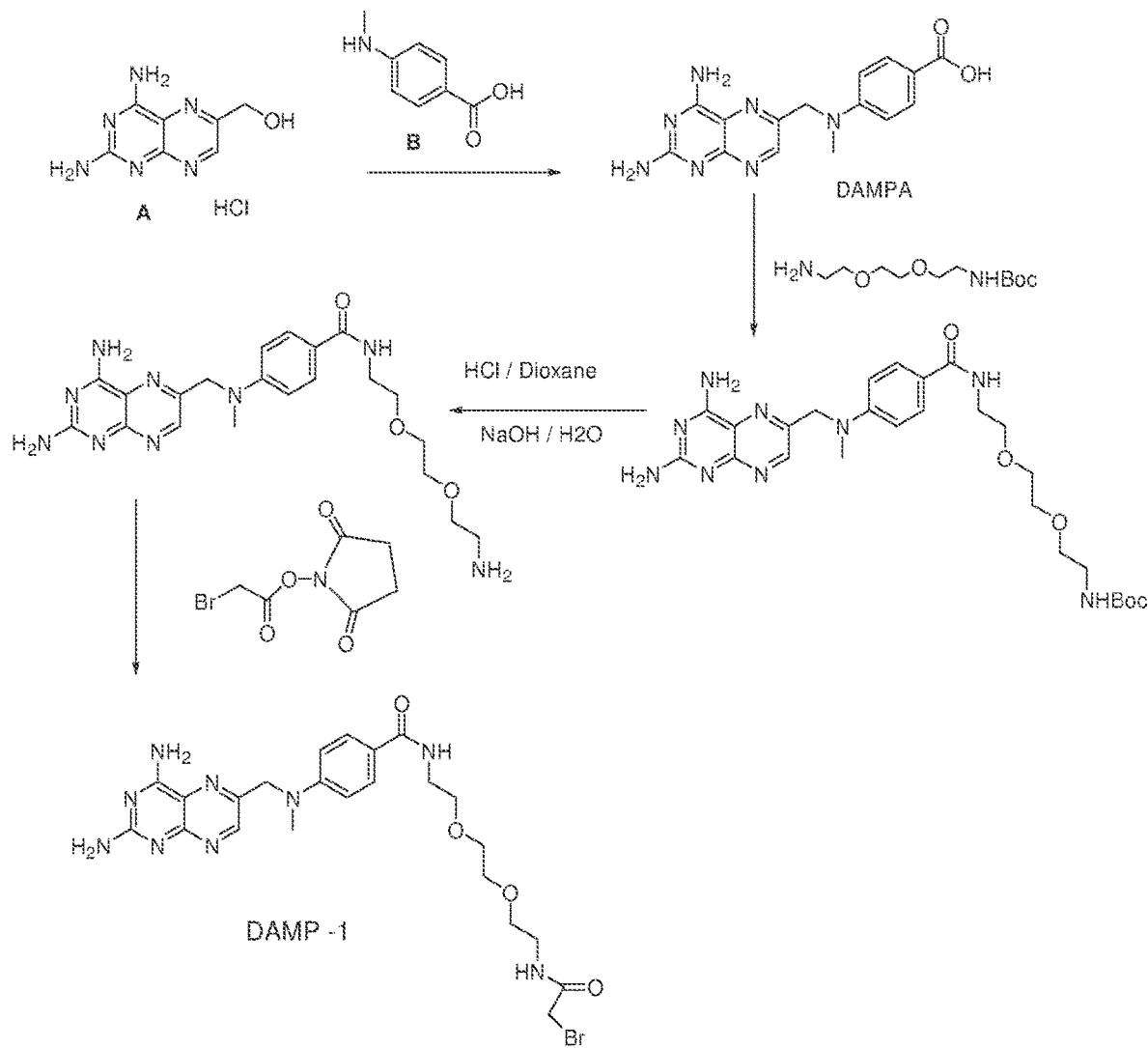
FIG. 4 shows the synthesis scheme for the DAMP-1 hapten, according to embodiments of the present disclosure.
Figure 5:
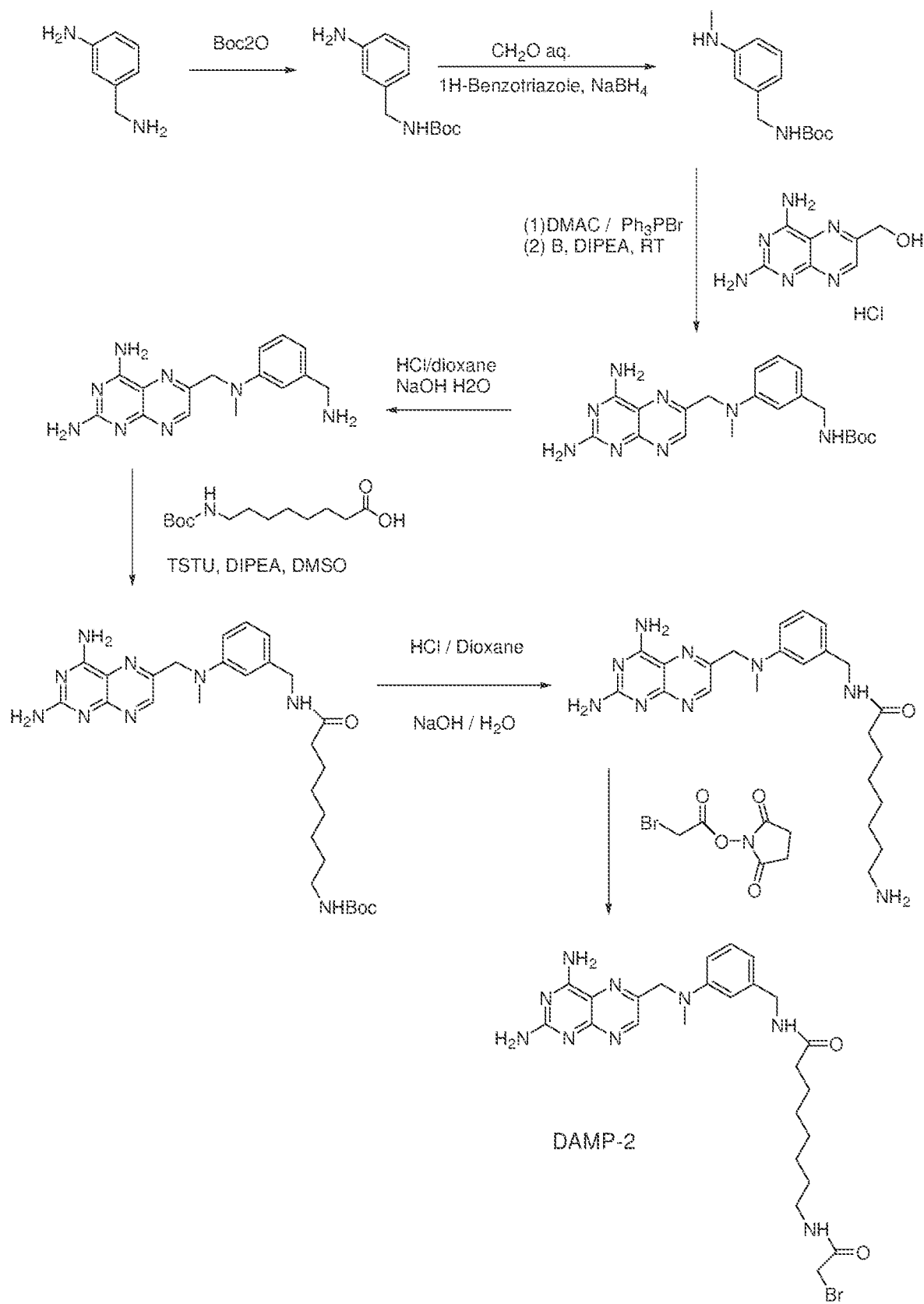
FIG. 5 shows the synthesis scheme for the DAMP-2, a MTX analog hapten, according to embodiments of the present disclosure.
Figure 6:
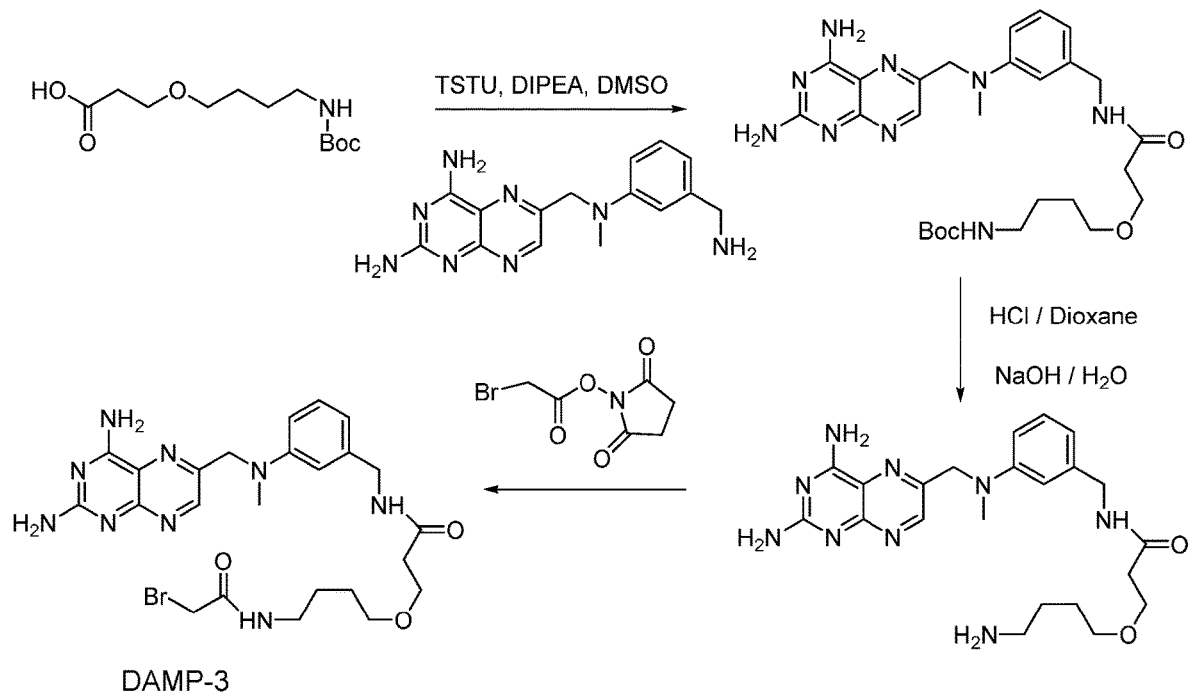
FIG. 6 shows the synthesis scheme for the DAMP-3 hapten, according to embodiments of the present disclosure.
Figure 7:
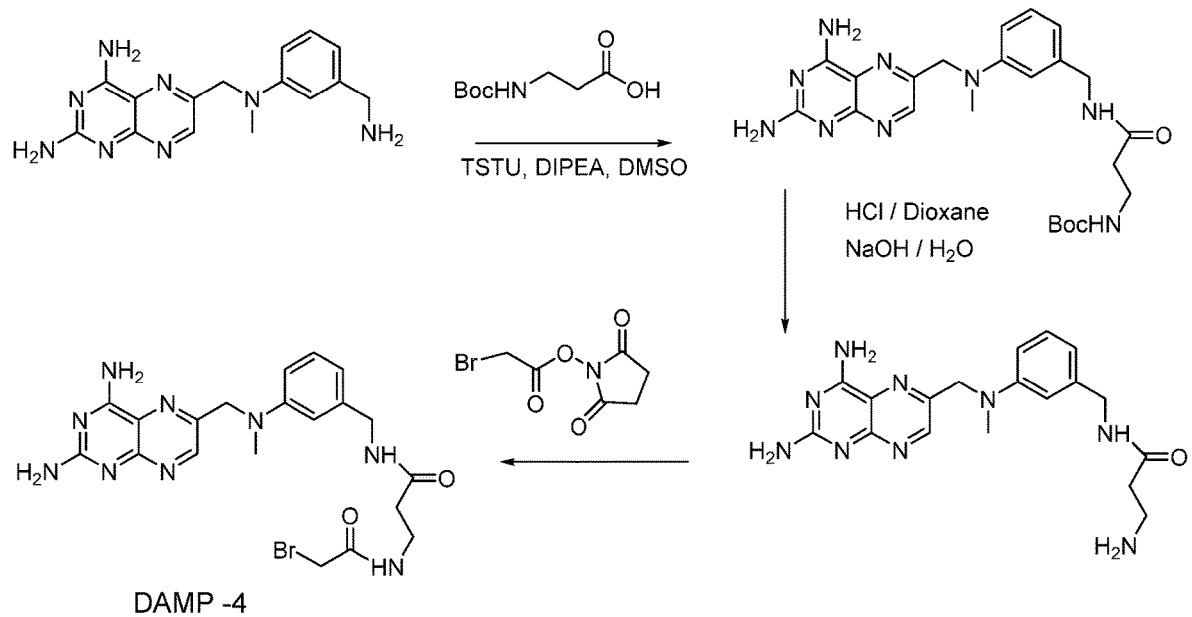
FIG. 7 shows the synthesis scheme for the DAMP-4 hapten, according to embodiments of the present disclosure.
Figure 8:
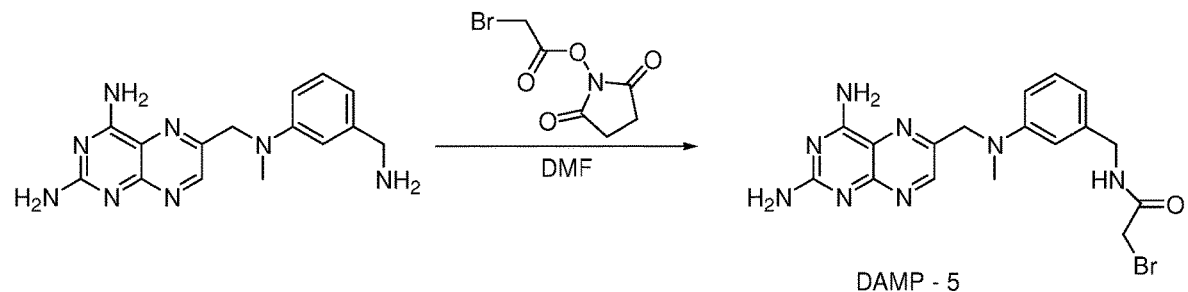
FIG. 8 shows the synthesis scheme for the DAMP-5 hapten, according to embodiments of the present disclosure.
Figure 9:
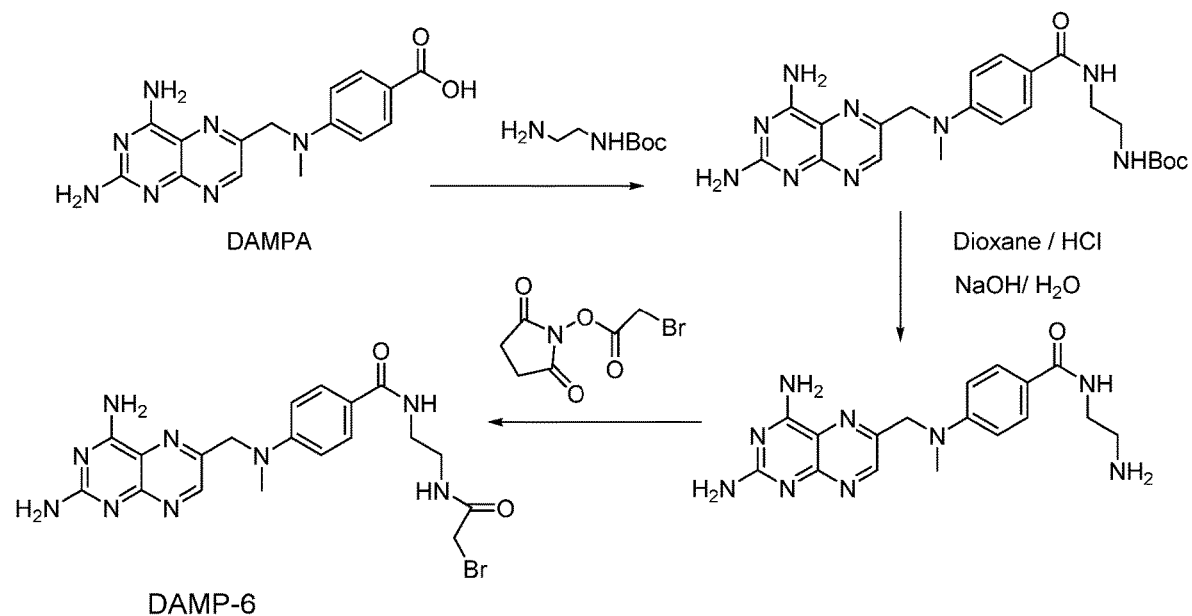
FIG. 9 shows the synthesis scheme for the DAMP-6 a MTX analog hapten, according to embodiments of the present disclosure.

From these experiments rabbits 21342 and 26494 were selected to isolate PBMC's as a source of B-cells for cloning from rabbits immunized with DAMP-Y-S-KLH immunogen. Screening 24 rabbit polyclonal antisera immunized with DAMP-Y-SH-KLH was performed to select the clones that gave the maximum separation (delta mA/min) in an MTX assay with minimal cross reactivity to 7-OH MTX, trimethoprim and triamterene and the folic acid analogs shown in FIG. 3.

Example 11

Preparation Rabbit Monoclonal Antibody

Rabbit recombinant monoclonal antibodies were prepared using single B-cell screening strategy for efficiently sampling the natural antibody repertoire of immunized rabbits. This technique is generally applicable to produce monoclonal antibodies to MTX as described herein.

Rabbit Peripheral blood mononuclear cells (PBMC's) from immunized animals #21342 and #26494 were used as a source of B-cells. PBMC's were isolated from approximately 40 mL whole blood from each rabbit using standard density gradient centrifugation procedure. The PBMC's were diluted in PBS and theoretically dispensing single cell per well into forty 96-well plates the same day and cultured.

Resulting supernatants from each well were tested by indirect ELISA against DAMP-Y-S-BSA antigen Forty 96-well microtiter plates were coated with 0.1 µg/well DAMP-Y-S-BSA in 0.1 M carbonate buffer, pH 9.5 and stored over night at 4° C. The plates were emptied and then blocked with 3% skimmed milk powder in PBST with shaking for 1 hr at RT. After flicking off the blocking solution the plates were rinsed with PBST. Twenty-five µL of PBST were added to each well followed by adding 25 µL of cell supernatant to all the wells and incubated for 1 hr at 37° C. in an incubator. Plates were washed 5× with PBST with a total wash time of 30 min. Afterwards, 100 µL/well secondary antibody 1:10,000 (v/v) goat anti-rabbit IgGFc-HRP conjugate in PBST was added and plates were incubated for 1 hour at 37° C. under constant shaking. Plates were washed 5 times with PBST, total wash time of 30 min. TMB substrate was added at 50 uL/well, plates. After a five minute incubation in the dark for color to develop, the reaction was stopped by the addition of 50 µL of 1 N HCl. Color was read via a microplate reader at 450 nm, and data was transferred to a computer for analysis. Supernatants that bound the DAMP-Y-SH-BSA conjugate (produced color in the wells) were considered positives. A total of 32 cells were selected for cloning and expression.

For each ELISA well with an antigen-specific antibody, mRNA was isolated from the corresponding PBMC culture well and divided to separately synthesize cDNA from the variable regions of the rabbit genes, IgH and IgK. After two rounds of PCR to amplify, the cDNA was seamlessly ligated into separate mammalian expression vectors with a constant IgG region of the heavy chain or the constant IgK region of the light chain, respectively. Ligation mixtures were transformed into E. coli to select correct expression constructs and cultured to isolate plasmid. The expression constructs were co-transfected into HEK293 cells. Transfected cells were cultured 2 days to secrete the recombinant antibody. The antigen binding property of the recombinantly expressed antibodies were assessed by indirect ELISA against DAMP-Y-S-BSA antigen as described above. The clones selected were further used for evaluation in the homogeneous enzyme immunoassay format as described on Examples 12 and 15. DNA sequencing was performed for selected rabbit monoclonal antibodies and translated with a standard code to provide protein sequence data for all heavy chain and kappa chain variable region sequences. The Table below summarizes the phases resulting in monoclonal antibodies.

TABLE 4a

| Immunization Phase | | | Enrichment & Selection Phase | | Cloning & Expression Phase | |
|---|---|---|---|---|---|---|
| No. rabbits immunized | Immunogen | Rabbit ID no. selected for cloning | No. B cells positive by indirect ELISA against DAMP-Y-S-BSA-antigen | | No. of cells cloned and expressed | ID of clones selected for testing and sequencing |
| 24 | KLH-S-Y DAMP 5 | #21342 | 190 58 | | 23 29 | 28H3-K1 32 H1-K2 64 H1-K1 |

Example 12

Reagents and Assays

MTX antibodies and enzyme conjugates may be advantageously used in accordance with the present disclosure in a homogeneous assay format to detect a MTX analyte in samples. Antibodies may be evaluated by known methods, such as, conjugate inhibition, conjugate modulation, calibration, cross-reactivity and spike-recovery. For these purposes, cloned antibodies (28H3-K1, 32H1-K2, 64H1-K1) is added into the antibody diluent to prepare the antibody reagent. The antibody reagent includes antibody as prepared above, buffer, salts, stabilizers, preservatives, NAD$^+$, and glucose-6-phosphate. Enzyme conjugate DAMP-Y-S-G6PDH is added into the conjugate diluent to prepare the enzyme conjugate reagent. The enzyme conjugate reagent includes the conjugate, buffer, stabilizers, salts, and preservatives.

A clinical chemistry analyzer useful to evaluate antibodies and enzyme conjugates in a homogeneous enzyme immunoassay format is the Beckman Coulter AU480 (Beckman Coulter, Brea, CA). The Beckman AU480 is an automated biochemistry spectrophotometer analyzer used by medical laboratories to process biological fluid specimens, such as urine, cerebrospinal fluid, oral fluids, plasma and serum. The analyzer is capable of maintaining a constant temperature, pipetting samples, mixing reagents, measuring light absorbance and timing the reaction accurately.

A homogeneous enzyme immunoassay is conducted using a liquid, ready-to-use, two reagent assay as described above. Typically, 2-15 µL MTX analyte-containing sample is incubated with 75-150 µL antibody reagent followed by the addition of the 50-100 µL enzyme conjugate reagent.

The assay is a homogeneous enzyme immunoassay technique used for the analysis of MTX in biological fluids. The assay is based on competition between MTX in the specimen and -MTX or MTX analog (DAMP derivatives of the current invention) labeled with the enzyme glucose-6-phosphate dehydrogenase (G6PDH) for antibody binding sites. Enzyme activity decreases upon binding to the antibody, so the drug concentration in the sample can be measured in terms of enzyme activity. Active enzyme converts nicotinamide adenine dinucleotide (NAD$^+$) to NADH, resulting in an absorbance change that is measured spectrophotometrically at 340 nm. Endogenous serum G6PDH does not interfere because the coenzyme NAD$^+$ functions only with the bacterial (*Leuconostoc mesenteroides*) enzyme employed in the assay. The change in the absorbance at 340 nm can be measured spectrophotometrically and is proportional to the enzyme conjugate activity which in turn is related to analyte concentration (see FIG. 14).

Example 13

Antibodies and Calibration Using MTX Analyte

MTX analyte antibodies and enzyme conjugate (DAMP-Y-S-G6PDH) were used in a homogeneous assay format to generate calibration curves using MTX standards as described in Example 12. Antibody reagents were prepared as described in Example 8 through 11 using DAMP-Y-KLH generated rabbit antibodies and cloned antibodies through B-cell. Enzyme conjugate DAMP-Y-S-G6PDH was used to prepare the conjugate reagent. A 6-point calibration curve was generated on the Beckman AU480 clinical chemistry analyzer as described in Examples 12. These experiments demonstrated that polyclonal antibodies rabbit #21342, rabbit #26494, rabbit #27420 and cloned monoclonal antibodies have antibody binding reaction to MTX demonstrating a dose-response relationship.

Approximately 30 mL of heparinized whole blood from Rabbits #25149 (MT-1) and #25779 (MT-2) were collected, and the peripheral blood mononuclear cells (PBMC's) were isolated from the whole blood and cultured. In vitro culture (40×96 wells per rabbit) of the B-cells and a screening of the supernatants by indirect ELISA against MTX-BSA antigen were performed. Rabbit #25149 had 240 antigen-positive B cell candidates and rabbit #25779 had 27 antigen-positive B cell candidates. Thirty (30) antigen-positive B cells from rabbit #25149 and 6 antigen-positive B cells from rabbit #25779 were selected for cloning, expression, and further screening. In brief, mRNA was isolated from 36 selected B cells, cDNA was synthesized, and 2 rounds of PCR were performed to prepare the antibody variable region cDNA for cloning. Rabbit IgG heavy and kappa light chain variable region cDNA's were each cloned into mammalian expression vectors with a rabbit heavy chain and light chain constant region, respectively. Expression constructs were co-transfected into HEK 293 cells, and cell culture supernatants were assayed by indirect ELISA against MTX-BSA antigen. Thirty six (36) B-cells were successfully cloned and expressed in HEK 293 culture media. From the 36 B-cells successfully expressed, 10 clones were selected to proceed to the 20 mL stage (Table 4) to produce larger quantities of rabbit recombinant antibody for further characterization.

TABLE 4b

Ten clones selected to produce larger quantity of rabbit recombinant antibody

| Clone ID | Approx. Conc. (µg/mL) | Volume (mL) |
| --- | --- | --- |
| (MT-1) 19H1/19K1 | 2 | 20 |
| (MT-1) 28H3/28K1 | 1 | 20 |
| (MT-1) 32H1/32K2 | 0.5 | 20 |
| (MT-1) 42H2/42K3 | 2 | 20 |
| (MT-1) 44H1/44K1 | 2 | 20 |
| (MT-1) 55H1/55K1 | 1 | 20 |
| (MT-2) 57H3/57K3 | 2 | 20 |
| (MT-2) 59H3/59K1 | 2 | 20 |
| (MT-2) 61H1/61K1 | 0.5 | 20 |
| (MT-2) 64H1/64K1 | 2 | 20 |

The top clones (281H3/28K1, 321H1/32K2 and 64H1/64K1) were selected based on performance for larger scale production and purification (Table 5). These clones were then used for further studies. To make the initial antibody reagent, both clones were diluted to 100 µg/mL with antibody diluent. Then a 1:4 ratio mixture of Clone 3211/32K2 to Clone 64H1/64K1 was made and spiked into antibody diluent.

TABLE 5

Clones selected for yield of larger scale expression/purification.

| Clone (HC) | Clone (KLC) | Batch number | Conc. (mg/ml) | Amount (mg) |
| --- | --- | --- | --- | --- |
| 32H1 | 32K2 | 4221 | 6.34 | 371.5 |
| 64H1 | 64K1 | 4222 | 6.64 | 394.3 |

Example 14

Antibodies and Calibration Using MTX

Figure 14:
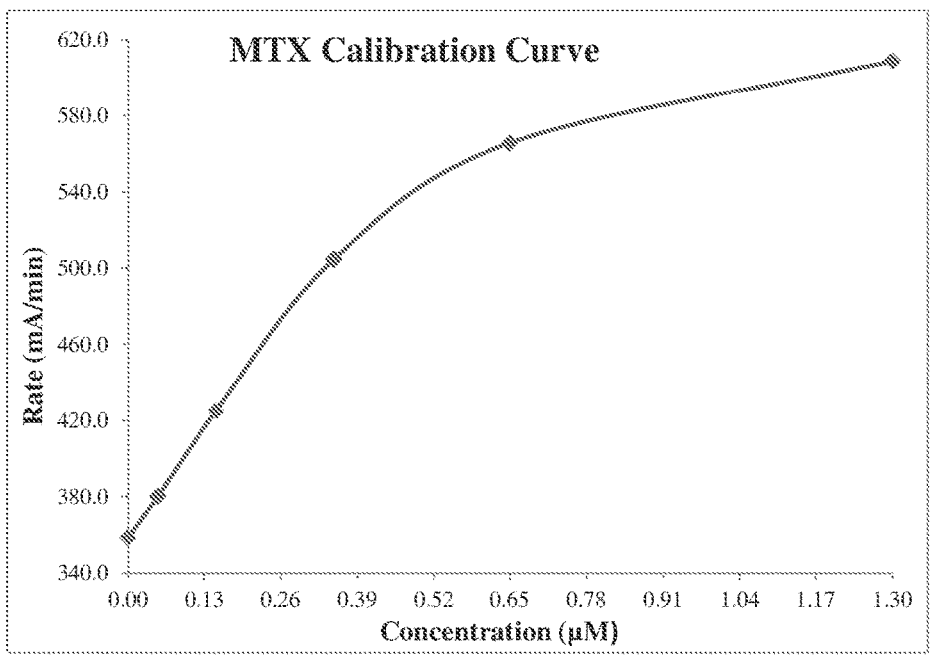
FIG. 14 shows a graph of a MTX calibration curve using monoclonal antibody 64H1-K1 according to embodiments of the present disclosure.

MTX analyte antibodies and enzyme conjugate (DAMP-Y-S-G6PDH) were used in a homogeneous assay format to generate calibration curves using standards prepared using MTX as described in Example 7. Antibodies from clones 64H1-K1 were used to prepare reagents and used in homogeneous assay format to detect MTX. The MTX was quantified from a calibration curve generated from standards prepared using MTX (FIG. 14). Enzyme conjugate DAMP-S-G6PDH was used to prepare the conjugate reagent. A 6-point calibration curve was generated on the Beckman AU480 clinical chemistry analyzer as described in Example 8. Typical calibration curves are shown in the table below and dose-response curves shown in FIG. 14. Spike-recovery experiments were performed as described and results are shown in Table 9.

Calibration Curve

The MTX Assay calibration range is from 0.00 to 1.30 µM. Calibration curves were generated on the Beckman AU680 by assaying each calibrator level in quadruplicate. The Beckman AU680 analyzer performs the nonlinear data analysis automatically using multi-parameter curve-fit math model. Typical calibrator separations are shown for the MTX Assay in Table 6. A calibration curve graph for feasibility lot reagents is shown in FIG. 2 and percent modulation was calculated as approximately 88.8% based on a max rate of 640.3 mA/min. The calculation for feasibility lot percent modulation is shown below:

Max Rate=640.3 mA/min.
Negative Calibrator Rate=358.5 mA/min.
High Calibrator Rate (1.30 µM)=608.7 mA/min.
Total Curve ΔmA=High Cal. Rate−Negative Cal. Rate (608.7 mA/min−358.5 mA/min)=250.2 mA/min % Modulation=ΔmA Total Curve÷(Max Rate−Neg. Cal. Rate)×100=% 250.2 mA/min÷(640.3 mA/min−358.5 mA/min)×100=88.8%

TABLE 6

Calibration Curve Separations for MTX Assay

| Calibrator Conc. (µM) | MTX (mA/min) |
| --- | --- |
| 0.00 | 358.5 |
| 0.05 | 380.0 |
| 0.15 | 424.8 |
| 0.35 | 504.6 |
| 0.65 | 565.6 |
| 1.30 | 608.7 |
| 0.00-0.05 | 21.5 |
| 0.05-0.15 | 44.9 |
| 0.15-0.35 | 79.7 |
| 0.35-0.65 | 61.0 |
| 0.65-1.30 | 43.1 |
| 0.00-1.30 | 250.2 |

TABLE 7a

| | 64H1/64K1 | | | | | |
| | 82.5 µL/g | | 90.0 µL/g | | 100.0 µL/g | |
| Cals (µM) | Absorbance | Average Rate (mA/min) | Absorbance | Average Rate (mA/min) | Absorbance | Average Rate (mA/min) |
| --- | --- | --- | --- | --- | --- | --- |
| 0.00 | 0.3378 | 338.10 | 0.3355 | 336.40 | 0.3401 | 340.60 |
| | 0.3384 | | 0.3373 | | 0.3411 | |
| 0.05 | 0.3772 | 377.35 | 0.3711 | 371.70 | 0.3698 | 368.85 |
| | 0.3775 | | 0.3723 | | 0.3679 | |
| 0.15 | 0.4548 | 454.05 | 0.4421 | 441.65 | 0.4318 | 431.90 |
| | 0.4533 | | 0.4412 | | 0.4320 | |
| 0.25 | 0.5152 | 515.80 | 0.5003 | 501.30 | 0.4786 | 479.10 |
| | 0.5164 | | 0.5023 | | 0.4796 | |
| 0.50 | 0.5708 | 571.65 | 0.5624 | 562.10 | 0.5529 | 552.00 |
| | 0.5725 | | 0.5618 | | 0.5511 | |
| 1.20 | 0.5943 | 594.20 | 0.5925 | 592.90 | 0.5913 | 590.70 |
| | 0.5941 | | 0.5933 | | 0.5901 | |
| Separation (ΔmA/min.) | | | | | | |
| 0.00 to 0.05 | | 39.3 | | 35.3 | | 28.3 |
| 0.05 to 0.15 | | 76.7 | | 69.9 | | 63.1 |
| 0.15 to 0.25 | | 61.8 | | 59.7 | | 47.2 |
| 0.25 to 0.50 | | 55.8 | | 60.8 | | 72.9 |
| 0.50 to 1.20 | | 22.6 | | 30.8 | | 38.7 |
| 0.00 to 1.20 | | 256.1 | | 256.5 | | 250.1 |

TABLE 7b

| | Clones | | | | | |
| | 19H1/19K1 200.0 µL/g | | 28H3/28K1 200.0 µL/g | | 32H1/32K2 200.0 µL/g | |
| Cals (µM) | Absorbance | Average Rate (mA/min) | Absorbance | Average Rate (mA/min) | Absorbance | Average Rate (mA/min) |
| --- | --- | --- | --- | --- | --- | --- |
| 0.00 | 0.3833 | | 0.4534 | | 0.4007 | |
| | 0.3829 | 383.10 | 0.4555 | 454.45 | 0.3982 | 399.45 |
| 0.05 | 0.3973 | | 0.4989 | | 0.5023 | |
| | 0.3948 | 396.05 | 0.4964 | 497.65 | 0.5035 | 502.90 |
| 0.15 | 0.4231 | | 0.5737 | | 0.6091 | |
| | 0.4244 | 423.75 | 0.5742 | 573.95 | 0.6080 | 608.55 |
| 0.25 | 0.4513 | 452.25 | 0.6088 | 610.00 | 0.6105 | 609.70 |
| | 0.4532 | | 0.6112 | | 0.6089 | |

TABLE 7b-continued

| | Clones | | | | | |
|---|---|---|---|---|---|---|
| | 19H1/19K1 200.0 µL/g | | 28H3/28K1 200.0 µL/g | | 32H1/32K2 200.0 µL/g | |
| Cals (µM) | Absorbance | Average Rate (mA/min) | Absorbance | Average Rate (mA/min) | Absorbance | Average Rate (mA/min) |
| 0.50 | 0.5542 | | 0.6112 | 610.20 | 0.6084 | |
| | 0.5516 | 552.90 | 0.6092 | | 0.6093 | 608.85 |
| 1.20 | 0.5986 | | 0.6095 | | 0.6108 | |
| | 0.6003 | 599.45 | 0.6144 | 611.95 | 0.6075 | 609.15 |
| Separation (ΔmA/min.) | | | | | | |
| 0.00 to 0.05 | | 13.0 | | 43.2 | | 103.5 |
| 0.05 to 0.15 | | 27.7 | | 76.3 | | 105.7 |
| 0.15 to 0.25 | | 28.5 | | 36.1 | | 1.2 |
| 0.25 to 0.50 | | 100.7 | | 0.2 | | −0.9 |
| 0.50 to 1.20 | | 46.6 | | 1.8 | | 0.3 |
| 0.00 to 1.20 | | 216.4 | | 157.5 | | 209.7 |

TABLE 7c

| | Clones | | | | | |
|---|---|---|---|---|---|---|
| | 42H2/42K3 200.0 µL/g | | 44H1/44K1 200.0 µL/g | | 55H1/55K1 200.0 µL/g | |
| Cals (µM) | Absorbance | Average Rate (mA/min) | Absorbance | Average Rate (mA/min) | Absorbance | Average Rate (mA/min) |
| 0.00 | 0.4566 | 456.70 | 0.5545 | 555.15 | 0.4929 | 494.15 |
| | 0.4568 | | 0.5558 | | 0.4954 | |
| 0.05 | 0.4916 | | 0.5748 | | 0.5458 | |
| | 0.4901 | 490.85 | 0.5759 | 575.35 | 0.5414 | 543.60 |
| 0.15 | 0.5524 | | 0.5839 | | 0.5948 | |
| | 0.5540 | 553.20 | 0.5882 | 586.05 | 0.5959 | 595.35 |
| 0.25 | 0.6071 | 604.65 | 0.5877 | 588.05 | 0.6065 | 607.50 |
| | 0.6022 | | 0.5884 | | 0.6085 | |
| 0.50 | 0.6151 | | 0.5887 | | 0.6097 | |
| | 0.6142 | 614.65 | 0.5905 | 589.60 | 0.6056 | 607.65 |
| 1.20 | 0.6139 | 614.10 | 0.5883 | 590.75 | 0.6107 | 611.25 |
| | 0.6143 | | 0.5932 | | 0.6118 | |
| Separation (ΔmA/min.) | | | | | | |
| 0.00 to 0.05 | | 34.2 | | 20.2 | | 49.5 |
| 0.05 to 0.15 | | 62.4 | | 10.7 | | 51.8 |
| 0.15 to 0.25 | | 51.4 | | 2.0 | | 12.2 |
| 0.25 to 0.50 | | 10.0 | | 1.6 | | 0.1 |
| 0.50 to 1.20 | | −0.5 | | 1.1 | | 3.6 |
| 0.00 to 1.20 | | 157.4 | | 35.6 | | 117.1 |

Example 15

Spike-Recovery

Known amounts of MTX analyte stock solution (mM) were added (spike) into synthetic matrix to achieve concentrations of 0, 0.06, 0.10, 0.30, 0.60, and 1.20 mmol/L These samples were quantified in triplicate by the homogeneous enzyme immunoassay to confirm concentration (recovery) of the spiked samples on the Beckman AU480 as described in Example 8. The samples were quantified using a separately prepared set of standards by generating a 6-point calibration curve. Calibration curve was generated using standards prepared using the same analyte as the analyte being quantified in the sample being tested. The Enzyme Conjugate Reagent contained conjugate DAMP-Y-S-G6PDH and the Antibody Reagents were from clones 28H3-K1, or 32H1-K2 or 64H1-K1. The MTX analyte concentration recovered in the spike-recovery experiments were compared to the known concentration.

Figure 15:
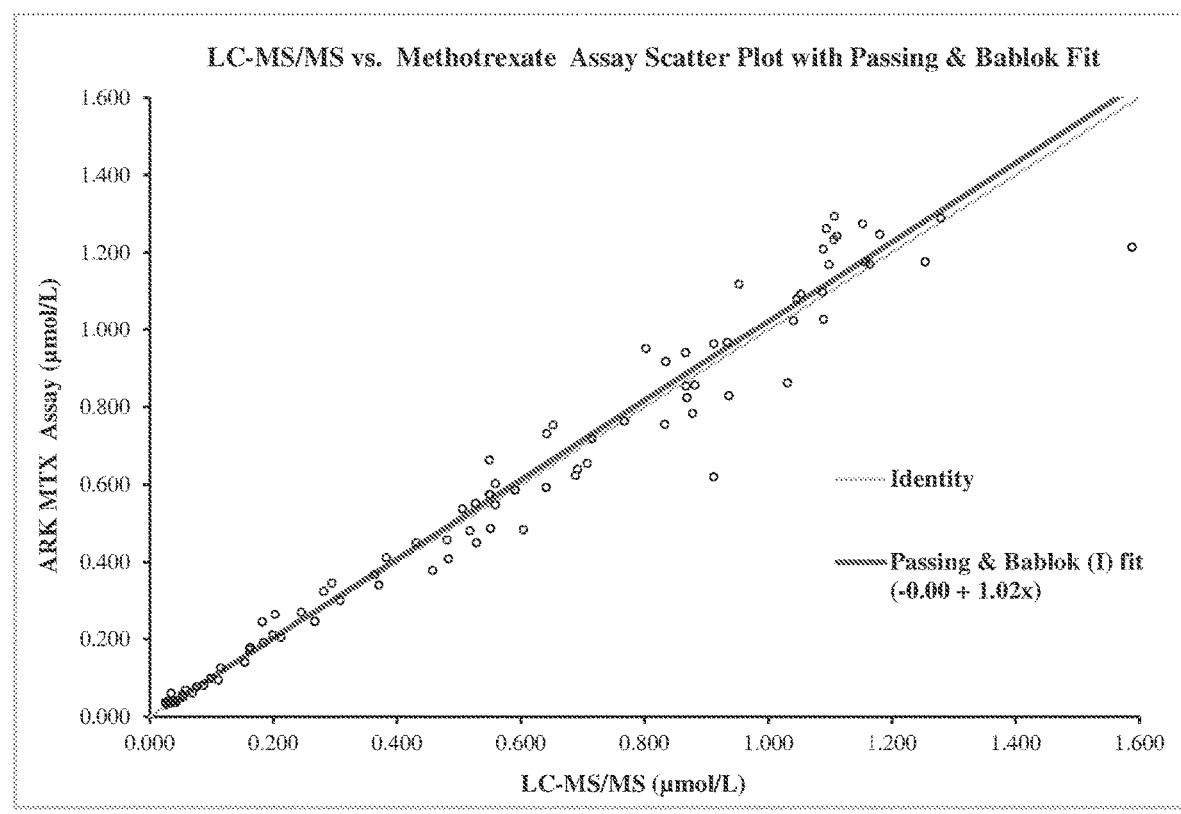
FIG. 15 shows Scatter Plot with Passing & Bablok Fit for LC-MS/MS vs. MTX Assay of the present disclosure.

In another experiment, the same samples as above were quantified in triplicate by the homogeneous enzyme immunoassay and by LC-MS-MS in duplicate. Deuterated MTX an internal standard was used for the LC-MS-MS method. The homogeneous enzyme immunoassay was prepared using clone 32H1-K2 or 64H1-K1 in the antibody reagent and enzyme conjugate DAMP-Y S-G6PDH in the enzyme conjugate reagent. Results show that the homogeneous enzyme immunoassay quantifies MTX levels in agreement with LC-MS-MS (FIG. 15).

In another experiment, known amounts of MTX were analyzed in the homogeneous enzyme immunoassay to confirm concentration (recovery) of the spiked samples on the Beckman AU480 as described in Example 12. Calibration curve was generated using standards prepared using the same analyte as the analyte being quantified in the sample being tested. The Enzyme Conjugate Reagent contained conjugate DAMP-Y-S-G6PDH and the Antibody Reagents were prepared containing antibody clone 32H1-K2 and/or 64H1-K1. The MTX-analyte concentration recovered in the spike-recovery experiments were compared to the known concentration, results in Table 9.

Example 16

Table 8a, 8b, and 8c—Precision Study Results

A calibration curve was generated and 10 replicates of each QC sample were assayed. This procedure was repeated to yield 20 replicates for each control level. The root mean square (RMS SD) was calculated for each control level. As shown in table 8, the % CV for the MTX Assay ranged from 1.48% to 2.85% at all QC levels tested.

TABLE 8a

Preliminary Precision

| QC Samples | Mean (µmol/L) | RMS SD | % CV | N |
|---|---|---|---|---|
| Low 0.070 µmol/L | 0.069 | 0.002 | 2.85 | 20 |
| Mid 0.400 µmol/L | 0.411 | 0.006 | 1.48 | 20 |
| High 0.800 µmol/L | 0.809 | 0.019 | 2.29 | 20 |
| 5 µmol/L | 4.717 | 0.074 | 1.57 | 20 |
| 50 µmol/L | 48.050 | 0.724 | 1.51 | 20 |
| 500 µmol/L | 467.300 | 7.573 | 1.62 | 20 |

Precision Evaluation (Total Precision or Within-Laboratory Precision) was performed according to the CLSI guidelines. The study involved two runs per day; four replicates of each level per run for twenty (20) non-consecutive days. One (1) calibration curve was performed during this 20-day interval. All QC control levels and corresponding pooled human serum control samples were tested in each run. The pooled serum samples were used to demonstrate equivalent precision in both the synthetic calibrator/control matrix and human serum.

Tables 8b and 8c summarize the precision of all the controls and patient serum pools during the 20 days and the CV's for the total precision ranged from 1.40% to 3.00%.

TABLE 8b

Calibration Range Controls Precision Evaluation (20 Days)

| Sample | N | Mean (µmol/L) | Within Run SD | Within Run CV (%) | Between Day SD | Between Day CV (%) | Total SD | Total CV (%) |
|---|---|---|---|---|---|---|---|---|
| Control Low | 160 | 0.069 | 0.002 | 2.84 | 0.001 | 1.23 | 0.002 | 3.00 |
| Control Mid | 160 | 0.411 | 0.006 | 1.40 | 0.002 | 0.43 | 0.006 | 1.40 |
| Control High | 160 | 0.811 | 0.014 | 1.79 | 0.008 | 0.97 | 0.017 | 2.05 |
| Serum Low | 160 | 0.070 | 0.002 | 2.50 | 0.001 | 1.49 | 0.002 | 2.88 |
| Serum Mid | 160 | 0.404 | 0.008 | 1.86 | 0.003 | 0.65 | 0.008 | 1.92 |
| Serum High | 160 | 0.846 | 0.016 | 1.93 | 0.008 | 0.95 | 0.017 | 2.06 |

TABLE 8c

High Range Controls Precision Evaluation (20 Days)

| Sample | N | Mean (µmol/L) | Within Run SD | Within Run CV (%) | Between Day SD | Between Day CV (%) | Total SD | Total CV (%) |
|---|---|---|---|---|---|---|---|---|
| Control 5 | 160 | 4.868 | 0.070 | 1.44 | 0.036 | 0.74 | 0.077 | 1.58 |
| Control 50 | 160 | 49.660 | 1.108 | 2.23 | 0.397 | 0.80 | 1.141 | 2.30 |
| Control 500 | 160 | 493.769 | 8.012 | 1.62 | 2.483 | 0.50 | 8.012 | 1.62 |
| Serum 5 | 160 | 5.247 | 0.076 | 1.45 | 0.028 | 0.54 | 0.078 | 1.49 |
| Serum 50 | 160 | 51.614 | 0.723 | 1.40 | 0.285 | 0.55 | 0.777 | 1.51 |
| Serum 500 | 160 | 507.988 | 7.632 | 1.50 | 4.240 | 0.83 | 8.538 | 1.68 |

Analytical Recovery

Test samples were prepared by spiking MTX into negative pooled human serum giving concentrations of 0.060, 0.100, 0.300, 0.600, 1.000, and 1.200 µmol/L. Table 9 shows the results for each level. The percent recovery ranged from 104.4% to 107.9%.

TABLE 9

Analytical/Spiked Recovery

| Conc. Tested (µmol/L) | Mean (µmol/L) | SD | % CV | % Recovery | N |
|---|---|---|---|---|---|
| 0.060 | 0.063 | 0.002 | 3.14 | 104.4 | 6 |
| 0.100 | 0.105 | 0.002 | 1.74 | 105.2 | 6 |
| 0.300 | 0.322 | 0.005 | 1.48 | 107.2 | 6 |
| 0.600 | 0.628 | 0.007 | 1.12 | 104.7 | 6 |
| 1.000 | 1.079 | 0.047 | 4.33 | 107.9 | 6 |
| 1.200 | 1.293 | 0.053 | 4.06 | 107.8 | 6 |

Mean percent recovery: 106.2

Limit of Quantitation

Limit of Quantitation (LoQ) was performed according to Data Collection Guideline from CLSI.

The LoQ of the MTX Assay is defined as the lowest concentration for which acceptable inter-assay precision and recovery is observed.

A set of samples were prepared by spiking MTX into negative serum pool to give a theoretical concentration of 0.020, 0.030, 0.040, and 0.050 µmol/L. Eight replicates of the test samples were assayed twice from the same curve on Day 1, eight replicates were assayed twice from the same recalibrated curve on Day 2, and eight replicates were assayed once from a recalibrated curve on Day 3 to give a total yield of 40 replicates. Table 10 summarizes the results. At 0.030 µmol/L, precision was 4.87% CV, standard deviation was 0.002, and recovery was 113.6%, which met the criteria of LoQ.

Limit of Blank and Limit of Detection

The Limit of Blank (LoB) and Limit of Detection (LoD) were evaluated by testing 60 replicates of the BLANK (normal pooled human serum) and 60 replicates of a positive level (approximately 0.020 µmol/L MTX in serum) that exceeds the LoB. Three runs were done. In each run, 20 replicates of BLANK and 20 replicates of a low concentration MTX sample were analyzed.

The LoD is the actual concentration at which an observed test result is very likely to exceed the LoB and may therefore be declared as "detected."

TABLE 10

Limit of Quantitation

| Nominal Concentration (μmol/L) | N | Grand Mean (μmol/L) | RMS SD | CV | 95% Confidence Interval Lower (−2SD) | 95% Confidence Interval Upper (+2SD) |
|---|---|---|---|---|---|---|
| 0.000 | 60 | 0.000 | 0.001 | NA | −0.002 | 0.003 |
| 0.020 | 60 | 0.024 | 0.002 | 9.77 | 0.019 | 0.028 |
| 0.020 | 40 | 0.025 | 0.002 | 6.99 | 0.021 | 0.028 |
| 0.030 | 40 | 0.034 | 0.002 | 4.87 | 0.031 | 0.037 |
| 0.040 | 40 | 0.043 | 0.002 | 4.01 | 0.039 | 0.046 |
| 0.050 | 40 | 0.052 | 0.002 | 4.00 | 0.048 | 0.056 |

The following characteristics were determined according to CLSI EP17-A2 for the MTX Assay. The LoQ was determined to be 0.030 Mmol/L. LoB was calculated using the non-parametric method. The blank values were sorted in ascending order, and the 57 and 58' values were averaged to give an LoB value of 0.000 mol/L. The equation below was used to determine LoD.

LoD LoB+1.652 (SDs)

TABLE 11

Limit of Quantitation Summary
The following criteria were determined according
to CLSI EP17-A2 for the MTX Assay.

| Criterion | MTX (μmol/L) |
|---|---|
| Limit of Blank (LoB); N = 60 | 0.000 |
| 57$^{th}$ value = 0.000 μmol/L, 58$^{th}$ value = 0.000 μmol/L | |
| Limit of Detection (LoD); N = 60 | 0.004 |
| LoB + 1.652 SD, where SD = 0.002 | |
| Lower Limit of Quantitation (LLoQ); N = 40 | 0.030 |
| LLOQ − 2 SD > LOD | |
| with acceptable recovery | |

Specificity

Specificity testing study involved preparing samples with 0.050 μmol/L and 0.500 μmol/L of MTX plus the cross-reactant into negative serum pool. Solvent controls were also prepared and tested.

Table 12a shows % Interference for compounds tested in the presence of MTX, and Table.

TABLE 12a

Specificity in Presence of MTX

| Compound | Conc. Tested (μmol/L) | % Interference (0.050 μmol/L MTX) | % Interference (0.500 μmol/L MTX) |
|---|---|---|---|
| Adriamycin | 1000 | −3.92 | −0.03 |
| Cyclophosphamide | 2200 | 0.00 | −1.24 |
| Cytosine | 1000 | −0.66 | −0.78 |
| Dihydrofolic Acid | 1000 | 8.60 | 1.15 |
| Tetrahydrofolic Acid | 1000 | 6.79 | −0.64 |
| DL-6-Methyl-5,6,7,8-Tetrahydropterine | 1000 | −0.71 | −1.03 |
| Folic Acid | 1000 | 2.50 | 5.05 |
| Folinic Acid | 1000 | −0.65 | 0.15 |
| 5-Fluorouracil | 3000 | −0.33 | 0.90 |
| 6-Mercaptopurine | 1000 | 2.31 | −1.99 |
| 5-Methyltetrahydrofolic Acid | 1000 | 0.00 | −0.25 |
| Prednisolone | 1000 | −2.50 | 1.35 |
| Pyrimethamine | 1000 | −2.14 | −3.02 |
| Sulfamethoxazole | 1600 | 0.36 | −0.29 |
| Vinblastine | 1000 | −3.57 | −0.45 |
| Vincristine | 1000 | −0.42 | −0.24 |

TABLE 12a-continued

Specificity in Presence of MTX

| Compound | Conc. Tested (μmol/L) | % Interference (0.050 μmol/L MTX) | % Interference (0.500 μmol/L MTX) |
|---|---|---|---|
| 7OH-MTX | 50 | 8.72 | 0.58 |
| Trimethoprim | 150 | 0.97 | −0.95 |
| Triamterene | 25 | −0.65 | 0.79 |

TABLE 12b

Specificity in Absence of MTX

| Compound | Conc. Tested (μmol/L) | No MTX Mean (μmol/L) | % Cross-reactivity |
|---|---|---|---|
| Trimethoprim | 150 | 0.000 | 0.00 |
| Triamterene | 25 | 0.009 | 0.03 |

Cross-reactivity with DAMPA was also tested DAMPA stock solution was spiked into negative serum pool without the presence of MTX. Table 12c summarizes the results.

TABLE 12c

Specificity-DAMPA

| DAMPA | Apparent Conc. (μmol/L) | % Cross-reactivity |
|---|---|---|
| 0.04 μmol/L | 0.023 | 57.50 |
| 0.10 μmol/L | 0.052 | 51.50 |
| 0.50 μmol/L | 0.215 | 42.93 |
| 0.80 μmol/L | 0.187 | 23.42 |
| 1.00 μmol/L | 0.188 | 18.80 |

Endogenous Interference Substances

Endogenous interference substances were performed according to Data Collection Guideline of CLSI Pooled human serum was used as the control.

TABLE 13

Endogenous Interference

| Endogenous Substance | Minimum Specification of Concentration to Test | Concentration Tested | ± μmol/L from Control (0.050 μmol/L MTX) | % Interference (0.500 μmol/L MTX) |
|---|---|---|---|---|
| Human Albumin | 12 g/dL | 12 g/dL | 0.002 | −1.04 |
| Conj.-Bilirubin | 70 mg/dL | 72 mg/dL | 0.001 | 1.96 |
| Unconj.-Bilirubin | 70 mg/dL | 72 mg/dL | 0.003 | 0.23 |
| Cholesterol | 500 mg/dL | 500 mg/dL | 0.005 | 3.49 |
| Human IgG | 12 g/dL | 12 g/dL | 0.003 | 2.42 |
| Hemoglobin | 1000 mg/dL | 1000 mg/dL | −0.006 | −2.72 |
| Rheumatoid Factor | 1000 IU/mL | 1080 IU/mL | 0.001 | 3.52 |
| Triglycerides | 1000 mg/dL | 700 mg/dL | −0.005 | −7.15 |
| Uric Acid | 30 mg/dL | 30 mg/dL | 0.000 | 1.60 |

The preceding merely illustrates the principles of the embodiments of the present disclosure. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the embodiments and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

We claim:

1. A compound of Formula 1:

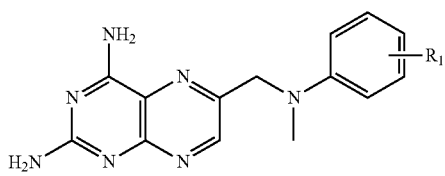

wherein $R^1$ is attached at the para or meta position;

wherein:

$R^1$ is —C(O)NH(CH$_2$CH$_2$O)$_2$(CH$_2$)$_2$NHC(O)CH$_2$—Z or —C(O)NH(CH$_2$)$_2$NHC(O)CH$_2$—Z, when $R^1$ is attached at the para position; or $R^1$ is —CH$_2$NHC(O)(CH$_2$)$_7$NHC(O)CH$_2$—Z; —CH$_2$NHC(O)(CH$_2$)$_2$NHC(O)CH$_2$—Z; —CH$_2$NHC(O)(CH$_2$)$_2$O(CH$_2$)$_4$NHC(O)CH$_2$—Z; or —CH$_2$NHC(O)CH$_2$—Z, when $R^1$ is attached at the meta position;

and

Z is selected from the group consisting of hydrogen, SH, S-acyl, halogen, NH$_2$, epoxy, maleimidyl, haloacetamide, activated carboxyl, azide, alkene, an immunogenic carrier, a protein, a label enzyme, a solid support and salts thereof.

2. The compound of claim 1, wherein Z is the immunogenic carrier.

3. The compound of claim 2, wherein the immunogenic carrier selected from the group consisting of a hemocyanin, a globulin, and an albumin.

4. The compound of claim 2, wherein the immunogenic carrier is bovine serum albumin (BSA) or keyhole limpet hemocyanin (KLH).

5. The compound of claim 2, wherein the immunogenic carrier is a polysaccharide.

6. The compound of claim 1, wherein Z is the label enzyme.

7. The compound of claim 6, wherein the label enzyme is selected from the group consisting of an alkaline phosphatase, a β-galactosidase and a horseradish peroxidase.

8. The compound of claim 6, wherein the label enzyme is glucose-6-phosphate dehydrogenase (G6PDH).

9. The compound of claim 1, wherein Z is the protein.

* * * * *